(12) United States Patent
Zeng et al.

(10) Patent No.: US 12,029,798 B2
(45) Date of Patent: Jul. 9, 2024

(54) PRE-TARGETING STRATEGIES FOR MOLECULAR IMAGING AND/OR RADIOIMMUNOTHERAPY

(71) Applicant: UNIVERSITY OF PITTSBURGH—OF THE COMMONWEALTH SYSTEM OF HIGHER EDUCATION, Pittsburgh, PA (US)

(72) Inventors: Dexing Zeng, Portland, OR (US); Lingyi Sun, Pittsburgh, PA (US); Yongkang Gai, Pittsburgh, PA (US)

(73) Assignee: UNIVERSITY OF PITTSBURGH—OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 55 days.

(21) Appl. No.: 16/179,785

(22) Filed: Nov. 2, 2018

(65) Prior Publication Data
US 2019/0134239 A1 May 9, 2019

Related U.S. Application Data

(63) Continuation of application No. PCT/US2017/030652, filed on May 2, 2017.

(60) Provisional application No. 62/373,036, filed on Aug. 10, 2016, provisional application No. 62/346,783, filed on Jun. 7, 2016, provisional application No. 62/330,622, filed on May 2, 2016.

(51) Int. Cl.
| | |
|---|---|
| *A61K 51/08* | (2006.01) |
| *A61K 9/51* | (2006.01) |
| *A61K 47/68* | (2017.01) |
| *A61K 51/10* | (2006.01) |
| *C07D 255/02* | (2006.01) |
| *C07D 257/02* | (2006.01) |
| *C07K 7/06* | (2006.01) |
| *C07K 7/64* | (2006.01) |
| *C07K 16/30* | (2006.01) |
| *G01N 33/50* | (2006.01) |
| *G01N 33/60* | (2006.01) |

(52) U.S. Cl.
CPC ............ *A61K 51/082* (2013.01); *A61K 9/51* (2013.01); *A61K 47/6893* (2017.08); *A61K 51/1027* (2013.01); *C07D 255/02* (2013.01); *C07D 257/02* (2013.01); *C07K 7/06* (2013.01); *C07K 7/64* (2013.01); *C07K 16/30* (2013.01); *G01N 33/5008* (2013.01); *G01N 33/60* (2013.01); *C07K 2319/00* (2013.01)

(58) Field of Classification Search
CPC ........... A61K 2123/00; A61K 2121/00; A61K 51/00; A61K 51/08; A61K 51/082; A61K 9/00; A61K 9/51; A61K 47/00; A61K 47/6893; A61K 51/1027; C07D 257/02; C07D 255/02; C07K 7/64; C07K 7/06; C07K 16/30; C07K 2319/00; G01N 33/60; G01N 33/5008
USPC .......... 424/1.11, 1.49, 1.65, 1.69, 1.81, 1.89, 424/9.1, 9.2, 9.3, 9.4, 9.5, 9.6; 530/300; 514/1, 1.1
See application file for complete search history.

(56) References Cited

U.S. PATENT DOCUMENTS

| | | | |
|---|---|---|---|
| 6,656,448 B1 * | 12/2003 | Carpenter, Jr. | ........ A61K 49/00 424/1.11 |
| 7,666,979 B2 | 2/2010 | Fan et al. | |
| 7,807,619 B2 * | 10/2010 | Bertozzi | ............... C07C 49/457 514/532 |
| 2005/0059101 A1 | 3/2005 | Ringold | |
| 2005/0130167 A1 | 6/2005 | Bao et al. | |
| 2009/0202435 A1 | 8/2009 | Port | |
| 2010/0196271 A1 | 8/2010 | Conti et al. | |
| 2011/0280801 A1 | 11/2011 | McBride et al. | |
| 2013/0122516 A1 | 5/2013 | Hong et al. | |
| 2015/0125904 A1 | 5/2015 | Ting et al. | |
| 2015/0132219 A1 | 5/2015 | Rigshospitalet | |

FOREIGN PATENT DOCUMENTS

| | | |
|---|---|---|
| WO | WO 2009/135015 A2 | 11/2009 |
| WO | WO 2011/045394 A1 | 4/2011 |

OTHER PUBLICATIONS

The National Inventors Hall of Fame, pp. 1-6. (Year: 2021).*
Goda et al, Biosensors and Bioelectronics, vol. 73, pp. 174-180 (Year: 2015).*
U.S. Appl. No. 16/179,817, filed Nov. 2, 2018.
Ali et al., "Simultaneous targeting of the epidermal growth factor receptor and cyclooxygenase-2 pathways for pancreatic cancer therapy," Molecular Cancer Therapeutics 4(12):1943-1951 (2005).
Ariyama et al., "Imaging of Small Pancreatic Ductal Adenocarcinoma," Pancreas 16(3):396-401 (1998).
Brooks, "Role of Integrins in Angiogenesis," European Journal of Cancer 32A(14):2423-2429 (1996).
Brooks et al., "Requirement of Vascular Integrin αvβ3 for Angiogenesis," Science 264:569-571 (1994).
Carroll et al., "Bioorthogonal chemistry for pre-targeted molecular imaging-progress and prospects," Organic & Biomolecular Chemistry 11:5772-5781 (2013).

(Continued)

*Primary Examiner* — D. L. Jones
(74) *Attorney, Agent, or Firm* — Baker Botts L.L.P.

(57) ABSTRACT

The present invention provides a method of targeted molecular imaging and/or targeted drug delivery, wherein two components or probes each interacts with one or more biomarkers on a cell and separately interact with each other to form a stable bond, such as a stable covalent bond. In certain non-limiting embodiments, at least one of the probes is photo-triggered to allow for bonding with at least one second probe. In certain non-limiting embodiments, the cell is a tumor or cancer cell. The present invention also relates to compounds, probes, and kits for use in targeted molecular imaging and/or targeted drug delivery.

12 Claims, 23 Drawing Sheets

(56) References Cited

OTHER PUBLICATIONS

Figure 1:
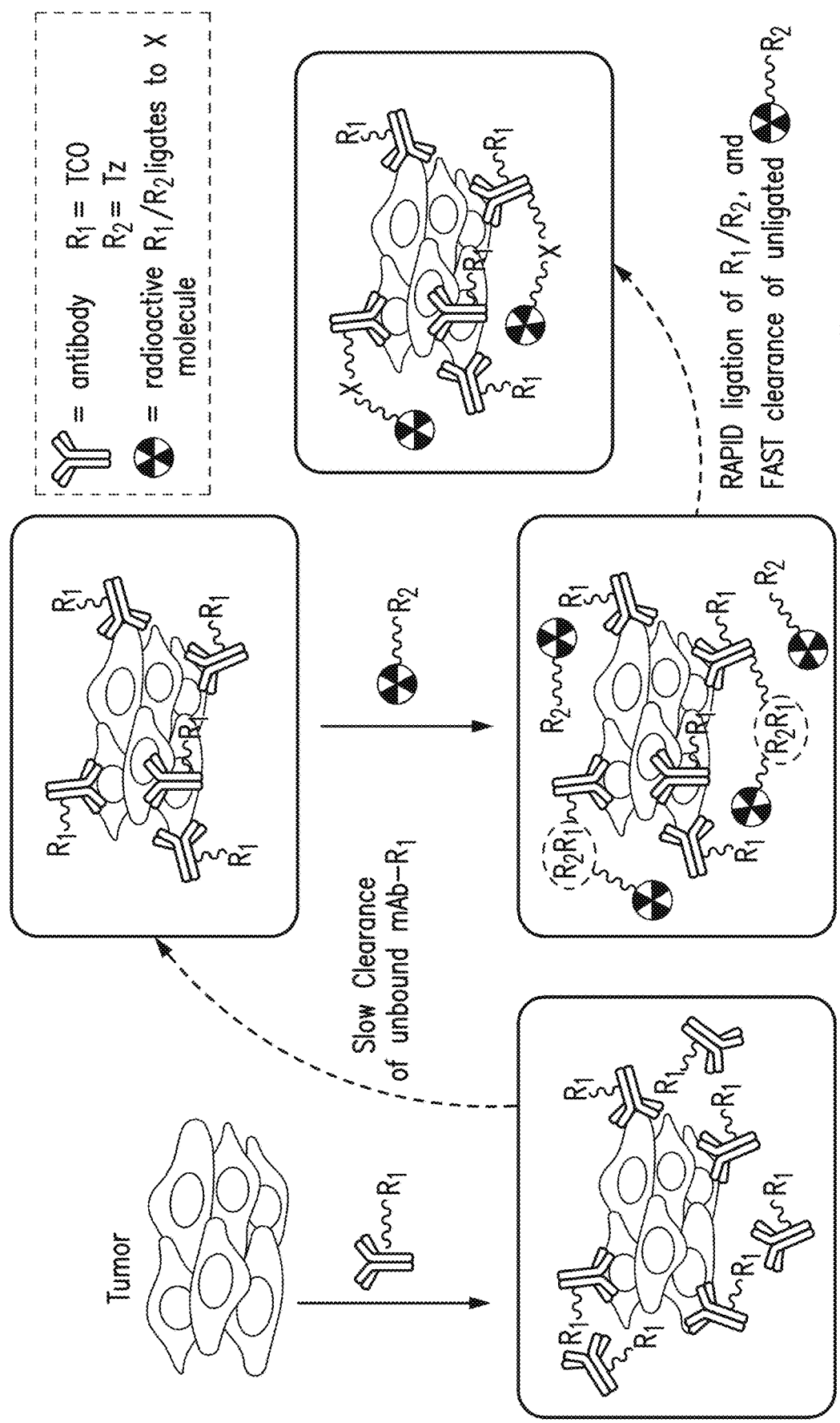

Cascinu et al., "Cetuximab plus gemcitabine and cisplatin compared with gemcitabine and cisplatin alone in patients with advanced pancreatic cancer: a randomised, multicentre, phase II trial," Lancet Oncol 9:39-44 (2008).
Castanon et al., "Epidermal Growth Factor Receptor Targeting in Non-Small Cell Lung Cancer: Revisiting Different Strategies Against the Same Target," Current Drug Targets 15:1273-1283 (2014).
Chang et al., "Development and Characterization of (89)Zr-Labeled Panitumumab for Immuno-Positron Emission Tomographic Imaging of the Epidermal Growth Factor Receptor," Molecular Imaging 12:17-27 (2013).
Chen et al., "Clinical Application of Radiolabeled RGD Peptides for PET Imaging of Integrin $\alpha v \beta 3$," Theranostics 6:78-92 (2016).
Ciardiello et al., "EGFR Antagonists in Cancer Treatment," N Engl. J Med 358:1160-1174 (2008).
Cohen et al., "Inert coupling of IRDye800CW to monoclonal antibodies for clinical, Optical imaging of tumor targets," EJNMMI Research 1:31 (2011), 13 pages, (2011).
Deri et al., "PET Imaging with 89Zr: From Radiochemistry to the Clinic," Nucl Med Biol 40:3-14 (2013).
Desgrosellier et al., "Integrins in cancer: biological implications and therapeutic opportunities," Nature Reviews Cancer 10:9-22 (2010).
Egawa et al., "Clinicopathological Aspects of Small Pancreatic Cancer," Pancreas 28:235-240 (2004).
Evans et al., "A bioorthogonal (68)Ga-labelling strategy for rapid in vivo imaging," Chemical Communications 50:9557-9560 (2014).
Gai et al., "Novel TACN chelator: a scaffold designed for dual-receptor targeted PET imaging," Journal of Nuclear Medicine 56(3):1053 (2015).
Ghadirian et al., "Epidemiology of pancreatic cancer: an overview," Cancer Detection and Prevention 27:87-93 (2003).
Girgis et al., "CA19-9 as a Potential Target for Radiolabeled Antibody-Based Positron Emission Tomography of Pancreas Cancer," International Journal of Molecular Imaging Article ID 834515, 9 pages (2011).
Goggins, "Identifying Molecular Markers for the Early Detection of Pancreatic Neoplasia," Seminars in Oncology 34:303-310 (2007).
Goldenberg et al., "Radioimmunodetection in Cancer Identification," Journal of Nuclear Medicine 33:803-814 (1992).
Goldenberg, "Cancer Imaging with CEA antibodies: historical and current perspectives," The International Journal of Biological Markers 7(3):183-188 (1992).
Goldenberg et al., "Pretargeted Molecular Imaging and Radioimmunotherapy," Theranostics 2(5):523-540 (2012).
Goldenberg et al., "Use of RadioLabeled Antibodies to Carcinoembryonic Antigen for the Detection and Localization of Diverse Cancers by External Photoscanning," The New England Journal of Medicine 298(25):1384-1388 (1978).
Goodwin et al., "Pre-Targeted Immunoscintigraphy of Murine Tumors with Indium-111-Labeled Bifunctional Haptens," Journal of Nuclear Medicine 29:226-234 (1988).
Goodwin et al., "Monoclonal antibody hapten radiopharmaceutical delivery," Nuclear Medicine Communications 7:569-580 (1986).
Haubner et al., "Noninvasive Visualization of the Activated $\alpha v \beta 3$ Integrin in Cancer Patients by Positron Emission Tomography and [18F]Galacto-RGD," PLoS Medicine 2(3):e70 (2005).
Hosotani et al., "Expression of Integrin aVB3 in Pancreatic Carcinoma: Relation to MMP-2 Activation and Lymph Node Metastasis," Pancreas 25(2):e30-e35 (2002).
Hutchinson, "Imaging: PET is prognostic of survival in pancreatic cancer patients," Nat Rev Clin Oncol 7:551 (2010).
Hynes et al., "ERBB Receptors and Cancer: The Complexity of Targeted Inhibitors," Nature Reviews, Cancer 5:341-354 (2005).
International Search Report dated Sep. 25, 2017 in International Application No. PCT/US17/30652.
International Search Report dated Sep. 25, 2017 in International Application No. PCT/US17/30662.

Kelly et al., "Targeted Nanoparticles for Imaging Incipient Pancreatic Ductal Adenocarcinoma," PLoS Medicine 5(4):e85 (2008).
Knight et al., "Bioorthogonal chemistry: implications for pretargeted nuclear (PET/SPECT) imaging and therapy," American Journal of Nuclear Medicine and Molecular Imaging 4(2):96-113 (2014).
Kubas et al., "Multivalent cyclic RGD ligands: influence of linker lengths on receptor binding," Nucl Med Biol 37:885-891 (2010).
Lamberts et al., "Antibody Positron Emission Tomography Imaging in Anticancer Drug Development," Journal of Clinical Oncology 33:1491-1504 (2015).
Larson et al., "PET Scanning of Iodine-124-3F9 as an Approach to Tumor Dosimetry during Treatment Planning for Radioimmunotherapy in a Child with Neuroblastoma," Journal of Nuclear Medicine 33:2020-2023 (1992).
Li et al., "(64)Cu-Labeled Tetrameric and Octameric RGD Peptides for Small-Animal PET of Tumor $\alpha(v)\beta(3)$ Integrin Expression," Journal of Nuclear Medicine 48:1162-1171 (2007).
Lurje et al., "EGFR Signaling and Drug Discovery," Oncology 77:400-410 (2009).
McNitt et al., "Photochemical generation of oxa-dibenzocyclooctyne (ODIBO) for metal-free click ligations," Org. Biomol. Chem. 10:8200-8202 (2012).
Mendelsohn et al., "Epidermal Growth Factor Receptor Targeting in Cancer," Seminars in Oncology 33:369-385 (2006).
Menke-van der Houven van Oordt et al., "(89)Zr-cetuximab PET imaging in patients with advanced colorectal cancer," Oncotarget 6(30):30384-30393 (2015).
Meyer et al., "(18)F-Based Pretargeted PET Imaging Based on Bioorthogonal Diels-Alder Click Chemistry," Bioconjugate Chemistry 27:298-301 (2016).
Michaud, "Epidemiology of Pancreatic Cancer," Minerva Chir 59(2):99-111 (2004).
Mizejewski, "Role of Integrins in Cancer: Survey of Expression Patterns," Proceedings of the Society for Experimental Biology and Medicine 222:124-138 (1999).
Neoptolemos et al., "A Randomized Trial of Chemoradiotherapy and Chemotherapy after Resection of Pancreatic Cancer," N Engl. J Med 350:1200-1210 (2004).
Persson et al., "First-in-human uPAR PET: Imaging of Cancer Aggressiveness," Theranostics 5(12):1303-1316 (2015).
Pfeifer et al., "Clinical PET of Neuroendocrine Tumors Using (64)Cu-Dotatate: First-in-Humans Study," Journal of Nuclear Medicine 53:1207-1215 (2012).
Li et al., "Receptor-binding, biodistribution, and metabolism studies of 64Cu—DOTA-cetuximab, a PET-imaging agent for epidermal growth-factor receptor-positive tumors," Cancer Biotherapy & Radiopharmaceuticals 23:158-171 (2008).
Reardan et al., "Antibodies against metal chelates," Nature 316:265-268 (1985).
Robinson et al., "Quantitative Immuno-Positron Emission Tomography Imaging of HER2-Positive Tumor Xenografts with an Iodine-124 Labeled Anti-HER2 Diabody," Cancer Research 65(4):1471-1478 (2005).
Rossin et al., "Highly Reactive *trans*-Cyclooctene Tags with Improved Stability for Diels-Alder Chemistry in Living Systems," Bioconjugate Chemistry 24:1210-1217 (2013).
Rossin et al., "In Vivo Chemistry for Pretargeted Tumor Imaging in Live Mice," Angew. Chem 122:3447-3450 (2010).
Rossin et al., "Diels-Alder Reaction for Tumor Pretargeting: In Vivo Chemistry Can Boost Tumor Radiation Dose Compared with Directly Labeled Antibody," Journal of Nuclear Medicine 54:1-7 (2013).
Rossin et al., "Tumor pretargeting with Diels-Alder: A TCO derivative with improved properties," Nuclear Medicine and Biology 64:630 (2014).
Rossin et al., "Trans-Cyclooctene Tag with Improved Properties for Tumor Pretargeting with the Diels-Alder Reaction," Molecular Pharmaceutics 11:3090-3096 (2014).
Roxin et al., "Flexible or fixed: a comparative review of linear and cyclic cancer-targeting peptides," Future Med. Chem. 4(12):1601-1618 (2012).
Sharkey et al., "Signal amplification in molecular imaging by pretargeting a multivalent, bispecific antibody," Nature Medicine 11(11):1250-1255 (2005).

(56) References Cited

OTHER PUBLICATIONS

Siegel et al., "Cancer statistics, 2014" CA Cancer J Clin 64:9-29 (2014).
Sohn et al., "Resected Adenocarcinoma of the Pancreas-616 Patients: Results, Outcomes, and Prognostic Indicators," J Gastrointest Surg 4:567-579 (2000).
Trajkovic-Arsic et al., "Multimodal Molecular Imaging of Integrin αvβ3 for In Vivo Detection of Pancreatic Cancer," Journal of Nuclear Medicine 55:446-451 (2014).
Xiong et al., "Cetuximab, a Monoclonal Antibody Targeting the Epidermal Growth Factor Receptor, in Combination with Gemcitabine for Advanced Pancreatic Cancer: A Multicenter Phase II Trial," Journal of Clinical Oncology 22(13):2610-2616 (2004).
Yoshimoto et al., "In vivo SPECT Imaging with (111)In-DOTA-c(RGDfK) to Detect Early Pancreatic Cancer in a Hamster Pancreatic Carcinogenesis Model," Journal of Nuclear Medicine 53:765-771 (2012).
Zeglis et al., "A Pretargeted PET Imaging Strategy Based on Bioorthogonal Diels-Alder Click Chemistry," Journal of Nuclear Medicine 54:1389-1396 (2013).
Zeglis et al., "Optimization of a Pretargeted Strategy for the PET Imaging of Colorectal Carcinoma via the Modulation of Radioligand Pharmacokinetics," Molecular Pharmaceutics 12:3575-3587 (2015).
Zeng et al., "Comparison of Conjugation Strategies of Cross-Bridged Macrocyclic Chelators with Cetuximab for Copper-64 Radiolabeling and PET Imaging of EGFR in Colorectal Tumor-Bearing Mice," Mol. Pharmaceutics 11:3980-3987 (2014).
Zeng et al., "The Growing Impact of Bioorthogonal Click Chemistry on the Development of Radiopharmaceuticals," Journal of Nuclear Medicine 54:829-832 (2013).
Liu et al., "Dual Integrin and Gastrin-Releasing Peptide Receptor Targeted Tumor Imaging Using $^{18}$F-labeled PEGylated RGD-Bombesin Heterodimer $^{18}$F-FB-PEG$_3$-Glu-RGD-BBN," J. Med. Chem., vol. 52, No. 2, pp. 425-432 (2009).
Oliveira et al., "Radiotracers for different angiogenesis receptors in a melanoma model," Melanoma Research, vol. 22, No. 1, pp. 45-53 (2012).
Schweinsberg et al., "Novel Glycated [99mTc(CO)3]-Labeled Bombesin Analogues for Improved Targeting of Gastrin-Releasing Peptide Receptor-Positive Tumors," Bioconjugate Chemistry, 19:2432-2439 (2008).
U.S. Appl. No. 16/179,817, filed Sep. 15, 2020 Final Office Action.
U.S. Appl. No. 16/179,817, filed Feb. 22, 2022 Non-Final Office Action.

* cited by examiner

Figure 7A
Figure 7B

PRE-TARGETING STRATEGIES FOR MOLECULAR IMAGING AND/OR RADIOIMMUNOTHERAPY

CROSS-REFERENCE TO RELATED APPLICATIONS

This application is a continuation of International Patent Application No. PCT/US2017/030652, filed May 2, 2017, which claims priority to U.S. Provisional Application No. 62/330,622, filed May 2, 2016, U.S. Provisional Application No. 62/346,783, filed Jun. 7, 2016, and United States Provisional Application No. 62/373,036, filed Aug. 10, 2016, the contents of each and all of which are hereby incorporated by reference in their entireties.

GRANT INFORMATION

This invention was made with government support under Grant Nos. EB017317 and EB020737 awarded by the National Institute of Health. The government has certain rights in the invention.

1. INTRODUCTION

The present invention relates to a dual-receptor pre-targeted molecular imaging and/or targeted drug delivery method, wherein a biomarker targeting ligand is integrated into an antibody-targeting molecule that carries the imaging label and/or drug. Therefore, the antibody-targeting molecule can bind to both a pre-administered target-specific antibody (e.g., tumor or cancer specific antibody) and a biomarker on the biological subject of interest (e.g., tumor or cancer cell) resulting in increased sensitivity, increased specificity, improved signal to noise ratio, and greater applicability, as both internalizing and non-internalizing probes (e.g., antibodies) can be used.

2. BACKGROUND OF THE INVENTION

Due to their specificity and affinity, antibodies radiolabeled with various radioisotopes are attractive targeting probes for molecular imaging and radioimmunotherapy (RIT). Directly radiolabeled monoclonal antibodies ("mAbs"), however, have a few intrinsic shortcomings, such as a relatively low tumor/non-tumor binding ratio and a relatively high radiation dose to patients due to the need to use radioisotopes with long half-lives (e.g., $^{89}$Zr; $t_{1/2}$=78.4 h).

As an alternative to using directly radiolabeled antibodies, a pre-targeting strategy (FIG. 1) was previously developed involving sequential administrations of a slow-clearing monoclonal antibody (mAb) vector and a fast-clearing radioactive molecule (RM). The fast clearing radionuclide must be administered at an optimal lag time for tumor accumulation and concomitant blood clearance of the pre-injected mAb.

Current pre-targeting strategies also have their own limitations that have tempered clinical translation including: 1) they are restricted to non-internalizing mAbs, because internalized mAbs are no longer available for ligation with the antibody-targeting RM; 2) they have significantly lower tumor uptake due to the rapid clearance and antibody-targeting RM's lack of tumor targeting, which consequently requires greater amounts of radionuclide to achieve high-quality imaging and effective radiotherapy; and 3) clinical translation to human use is hampered because in humans there is an over 100-fold dilution of the antibody-targeting RM in the circulation as compared to the antibody-targeting RM in mouse blood (5.4-6.0 mCi 64Cu in 5-7 L human blood vs 0.25-0.5 mCi 64Cu in 1.5-2 mL mouse blood).

Therefore, there is a need in the art for a molecular imaging and radioimmunotherapy method with increased sensitivity, increased selectivity, improved signal to noise ratio, and improved clinical translation, which can utilize both internalizing and non-internalizing antibodies.

3. SUMMARY OF THE INVENTION

The present invention relates to methods and compositions for targeted molecular imaging and/or targeted drug delivery. In its broadest aspect, the present invention relates to at least two components or probes that interact with biomarkers on a cell and separately interact with each other to form a stable covalent bond. It is based, at least in part, on the discovery that targeting both a first targeting probe (e.g., an antibody probe) and a second targeting probe (e.g., carrying a detectable label and/or active agent) to the tumor cell improves the sensitivity and/or specificity and/or cellular target uptake of the imaging label and/or active agent.

The present invention provides for methods, compositions, and kits for molecular imaging. In certain non-limiting embodiments, the methods comprise administering at least one first targeting probe, wherein the at least one first targeting probe comprises a primary targeting moiety, where the primary targeting moiety binds to a biomarker on or in a cell or tissue or other structure of interest, and a complexing target. In certain non-limiting embodiments, the method further comprises administering at least one second targeting probe, wherein the at least one second targeting probe comprises a secondary targeting moiety that recognizes the complexing target, a tertiary targeting moiety that binds to a second biomarker on or in a cell or tissue or other structure of interest, and a detectable label. In certain non-limiting embodiments, the at least one second targeting probe is administered after the at least one first targeting probe. In certain non-limiting embodiments, the at least one first targeting probe and the at least one second targeting probe are concurrently administered, or administered such that they are both locally present at effective levels at the cell, tissue, or other structure of interest. In certain non-limiting embodiments, the detectable label is an imaging label. In certain non-limiting embodiments, the imaging label can be, but is not limited to, $^{64}$Cu, $^{68}$Ga, $^{18}$F, $^{89}$Zr, $^{111}$In, or $^{99m}$Tc.

The present invention provides a method of targeting drug delivery. In certain non-limiting embodiments, the methods comprise administering at least one first targeting probe, wherein the at least one first targeting probe has a primary targeting moiety and a complexing target. In certain non-limiting embodiments, the methods comprise administering at least one second targeting probe, wherein the at least one second targeting probe has a secondary targeting moiety, a tertiary targeting moiety, and an active therapeutic agent. In certain non-limiting embodiments, the at least one second targeting probe is administered after the at least one first targeting probe. In certain non-limiting embodiments, the at least one first targeting probe and the at least one second targeting probe are administered concurrently, for example, overlapping administration or administration at the same time.

In certain non-limiting embodiments, the second targeting probe is labeled with an imaging label. In certain non-limiting embodiments, the imaging label can be, but is not limited to, $^{64}$Cu, $^{68}$Ga, $^{18}$F, $^{89}$Zr, $^{111}$In, or $^{99m}$Tc.

In certain non-limiting embodiments, the active agent can be, but is not limited to, a protein, peptide, small molecule, nanoparticle, pharmaceutical, or radiopharmaceutical. In certain non-limiting embodiments, the isotopic component of the radiopharmaceutical can be, but is not limited to, $^{67}Cu$, $^{177}Lu$, $^{90}Y$, $^{131}I$, $^{212}Bi$, $^{211}At$, $^{225}Ac$, $^{188}Re$, or $^{111}In$. In certain non-limiting embodiments, the small molecule can be, but is not limited to, doxorubicin, paclitaxel or fluorouracil.

In certain non-limiting embodiments, the secondary targeting moiety of the second probe binds to and/or reacts with the complexing target on the first targeting probe. In certain non-limiting embodiments, the complexing target of the first targeting probe comprises a first bioorthogonal ligation moiety and the secondary targeting moiety of the second targeting probe comprises a second bioorthogonal ligation moiety that ligates to the first bioorthogonal ligation moiety. In certain non-limiting embodiments, the complexing target of the first targeting probe comprises at least one azide moiety and the secondary targeting moiety of the second targeting probe comprises at least one cyclooctyne moiety. In certain non-limiting embodiments, the complexing target of the first targeting probe comprises at least one cyclooctyne moiety and the secondary targeting moiety of the second targeting probe comprises at least one azide moiety. In certain other non-limiting embodiments, the complexing target on the first targeting probe can be, but is not limited to, alkene or tetrazole. In certain other non-limiting embodiments, the secondary targeting moiety on the second targeting probe can be, but is not limited to, alkene or tetrazole. In certain non-limiting embodiments, the complexing target on the first targeting probe can be, but is not limited to, trans-cyclooctene or tetrazine. In certain non-limiting embodiments, the secondary targeting moiety on the second targeting probe can be, but is not limited to, trans-cyclooctene or tetrazine.

In certain non-limiting embodiments, the primary targeting moiety of the first targeting probe and the tertiary targeting moiety of the second targeting probe each bind to at least one biomarker of a biological subject of interest. In certain non-limiting embodiments, the first and second targeting probe target the same or different biomarker of a biological subject of interest. In certain non-limiting embodiments, if the first and second targeting probes bind two different biomarkers, the biomarkers are expressed on the same biological subject (e.g., cell, tissue, or other structure). In certain non-limiting embodiments, the biological subject of interest can be, but is not limited to, a tumor or cancer cell. In certain non-limiting embodiments, the biological subject of interest is a pancreatic cancer cell. In certain non-limiting embodiments, the biomarker can be expressed on the surface of the cell or internally. In certain non-limiting embodiments, the biomarker can be, but is not limited to, a cell surface protein. In certain non-limiting embodiments, the biomarker can be, but is not limited to, an integrin. In certain non-limiting embodiments, the biomarker can be, but is not limited to, epidermal growth factor receptor (EGFR) and/or integrin αvβ3.

In certain non-limiting embodiments, the first targeting probe can be, but is not limited to, a protein, antibody, peptide, small molecule, nanoparticle, polysaccharide, or polynucleotide. In certain non-limiting embodiments, the first targeting probe can be internalizable or non-internalizable. In certain non-limiting embodiments, the second targeting probe can be, but is not limited to, a protein, antibody, peptide, small molecule, nanoparticle, polysaccharide, or polynucleotide. In certain non-limiting embodiments, the second targeting probe can be internalizable or non-internalizable. In certain non-limiting embodiments, the primary targeting probe can be an anti-EGFR antibody, such as, but not limited to, cetuximab, panitumumab, nimotuzomab. In certain non-limiting embodiments, the secondary targeting probe can be the peptide, such as, but not limited to, cyclo(RGDyK) (RGD).

In certain non-limiting embodiments, the complexing target of the first targeting probe comprises a photolabile moiety and the secondary targeting moiety of the second targeting probe comprises a moiety that only binds to and/or reacts with the photolabile moiety once it has been exposed to photon irradiation. In certain non-limiting embodiments, the photolabile moiety can be, but is not limited to, Photo-OIDBO.

In certain non-limiting embodiments, the present invention provides a kit for targeted medical imaging and/or targeted drug delivery. In certain non-limiting embodiments, the kit includes at least one first targeting probe comprising a primary targeting moiety and a complexing target. In certain non-limiting embodiments, the kit includes at least one second targeting probe selected from either an imaging probe or a therapeutic probe. In certain non-limiting embodiments, the imaging probe includes a secondary targeting moiety, tertiary targeting moiety, and a detectable label. In certain non-limiting embodiments, the therapeutic probe includes a secondary targeting moiety, tertiary targeting moiety, and an active agent. In certain non-limiting embodiments, the kit contains instructions for using the kit.

4. BRIEF DESCRIPTION OF THE FIGURES

FIG. 1. Traditional trans-cyclooctene (TCO)/tetrazine (Tz)-based pre-targeted PET imaging (for comparison).

Figure 2:
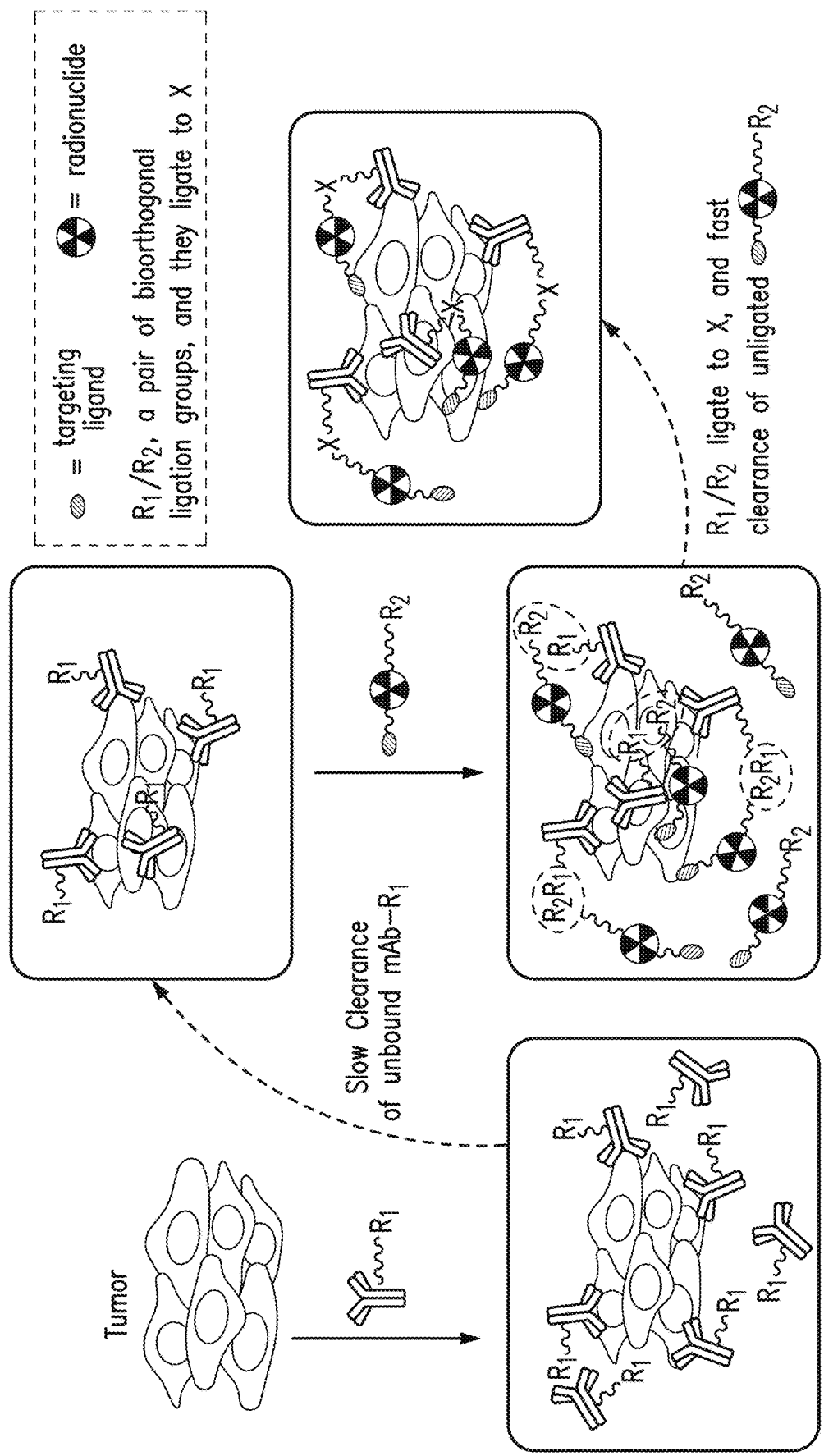

FIG. 2. Dual-receptor pre-targeted imaging strategy.

Figure 3:
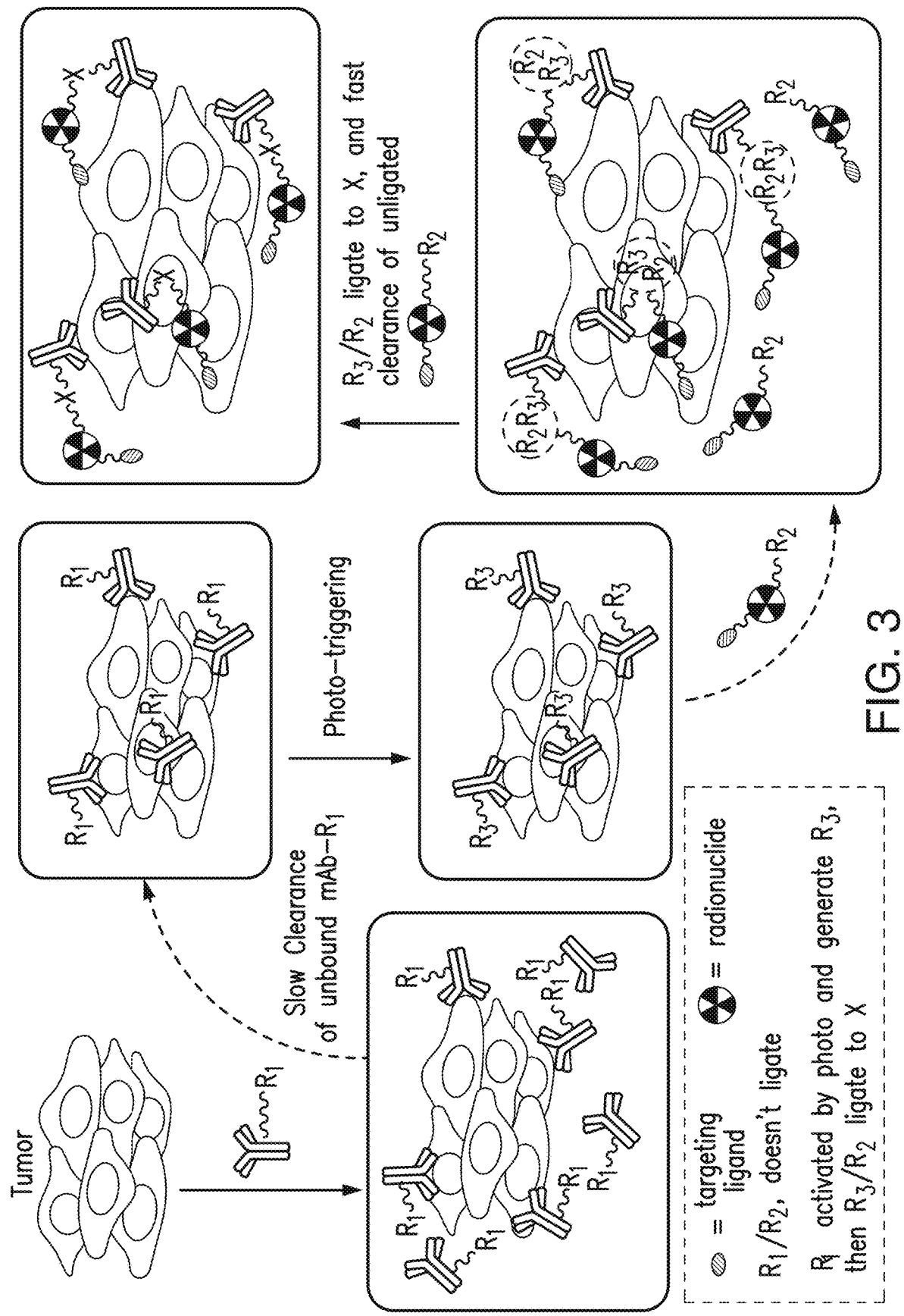

FIG. 3. Photon-triggered dual-receptor pre-targeted imaging strategy.

FIG. 4A-FIG. 4D. PET imaging of mice bearing 4T1 cells (left shoulder) & U87MG (right shoulder). FIG. 4A provides PET images for pre-targeting with dual-receptor pre-targeting (DRPT), cetuximab-PEG$_4$-TCO+Tz-($^{64}$Cu)NOTA-PEG$_4$-RGD (18 h p.i.). FIG. 4B provides PET images for traditional pre-targeting, cetuximab-PEG$_4$-TCO+Tz-($^{64}$Cu) NOTA (18 h p.i.). FIG. 4C provides PET images for direct targeting using cetuximab-($^{64}$Cu)NOTA (18 h p.i.). FIG. 4D provides PET images for targeting with ($^{64}$Cu)NOTA-PEG$_4$-RGD (1 h p.i.).

Figure 5:
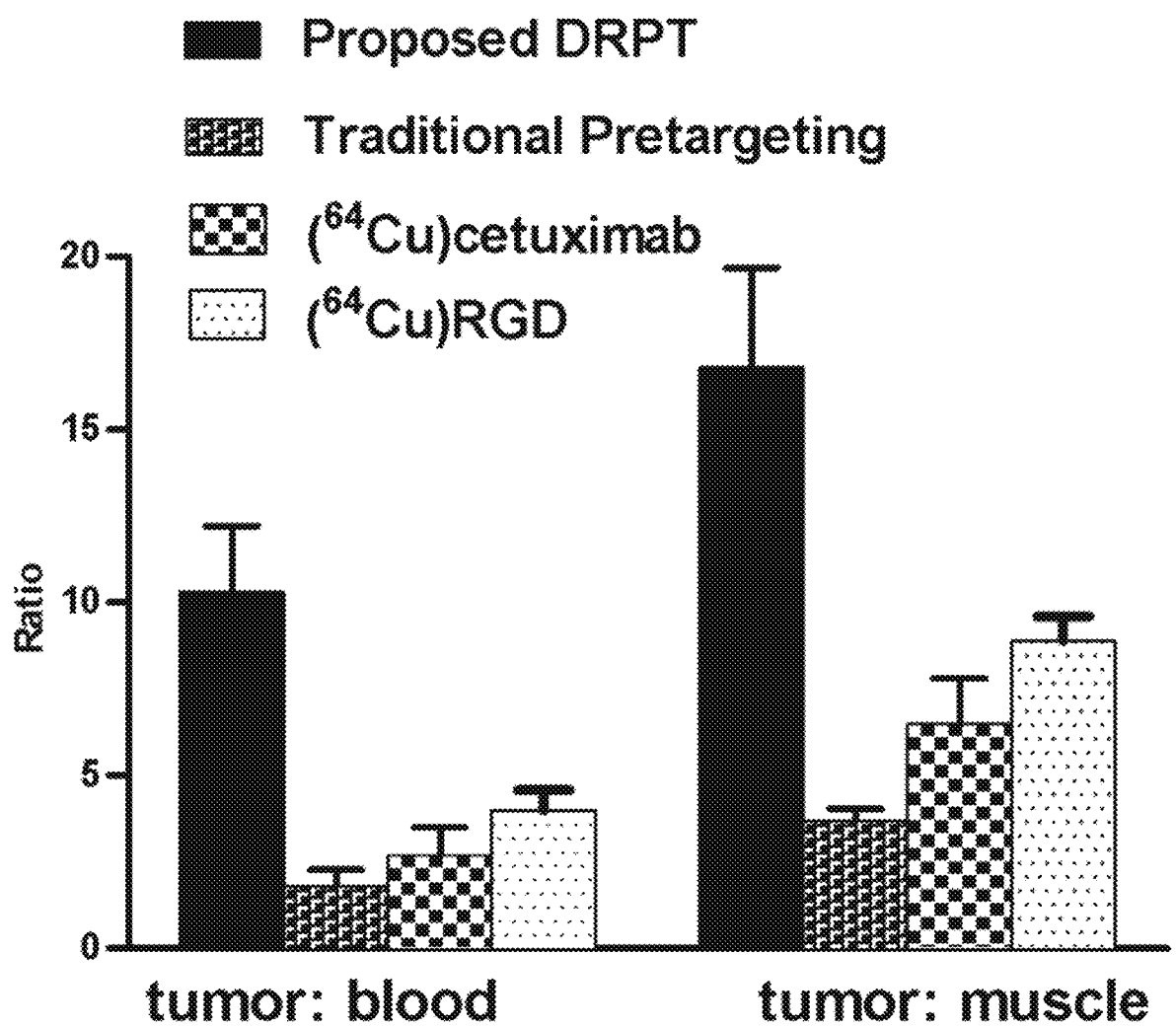

FIG. 5. Graph examining tumor/non-tumor binding ratios.

Figure 6:
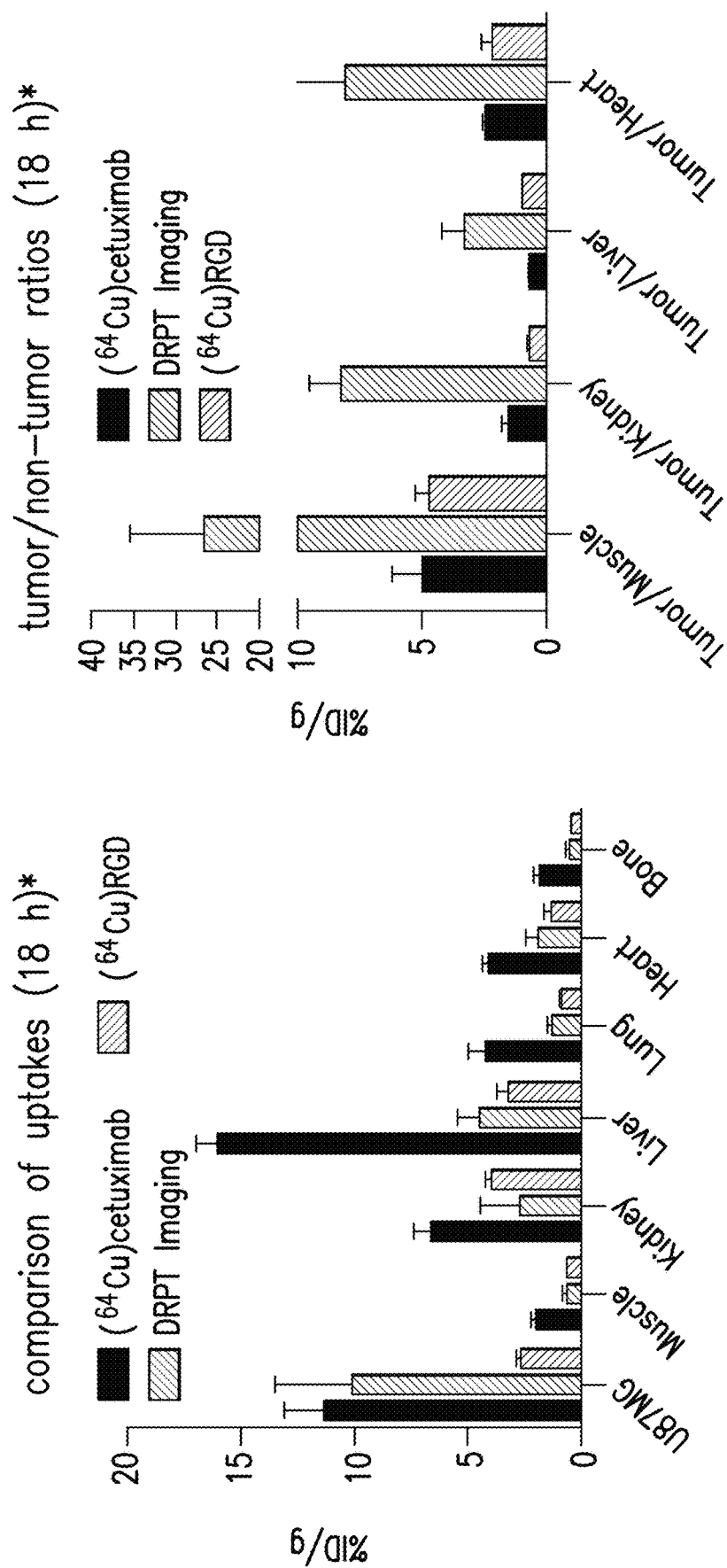

FIG. 6. Comparison of uptakes (left) and tumor/non-tumor binding ratios (right).

FIG. 7A-FIG. 7B. PET/CT imaging (18 h, p.i.) of mice bearing 4T1 (left shoulder) and U87MG (right shoulder) xenografts using DRPT strategy. FIG. 7A provides images after treatment with cetuximab-PEG$_4$-TCO+Tz-($^{64}$Cu)-PEG$_4$-RGD.

FIG. 7B provides images after treatment with cetuximab-PEG$_4$-TCO+Tz-($^{64}$Cu)-RGD.

Figure 8A:
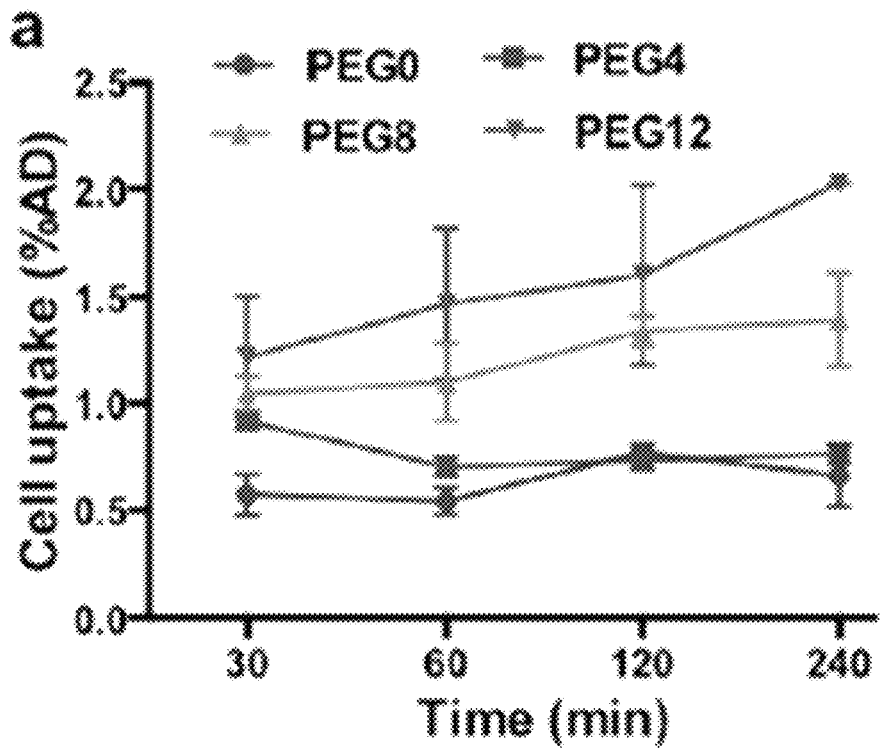
Figure 8B:
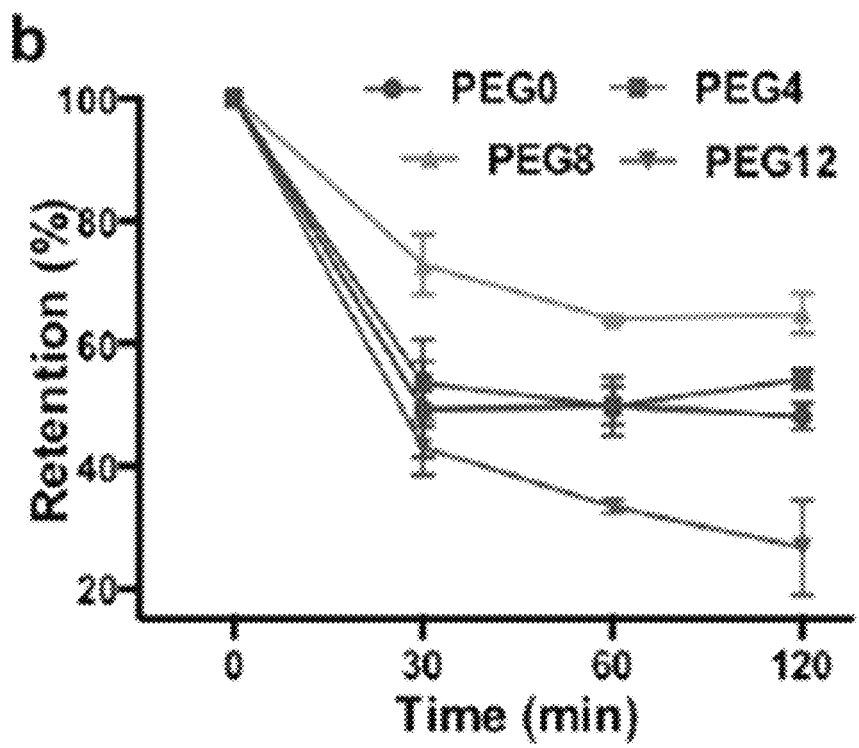
Figure 8C:
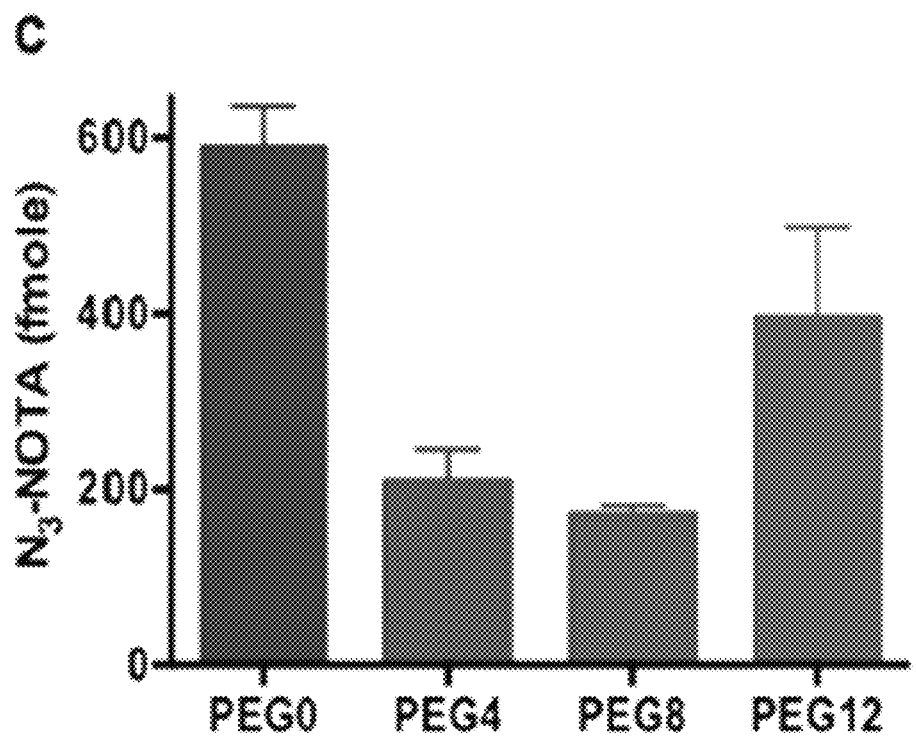

FIG. 8A-FIG. 8C. In vitro spacer evaluation results. FIG. 8A provides results from a traditional cell uptake assay. FIG. 8B provides results from a cell efflux assay. FIG. 8C provides in vitro screen results using a spacer optimization platform in accordance with this invention.

Figure 9:
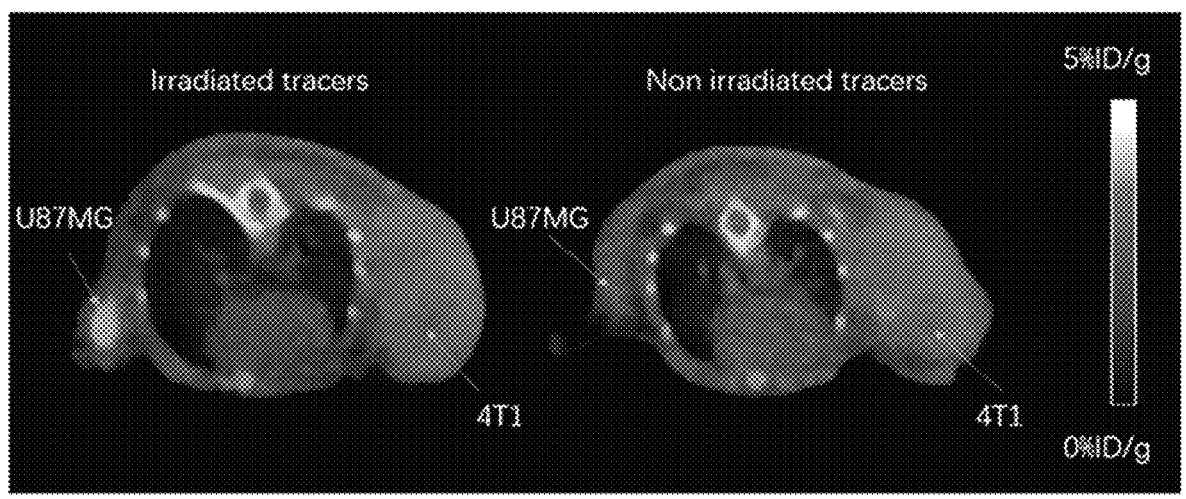

FIG. 9. PET/CT imaging of mice bearing human U87MG and mouse 4T1 tumor xenografts: left, with photon-irradiation; right without photon-irradiation.

Figure 10:
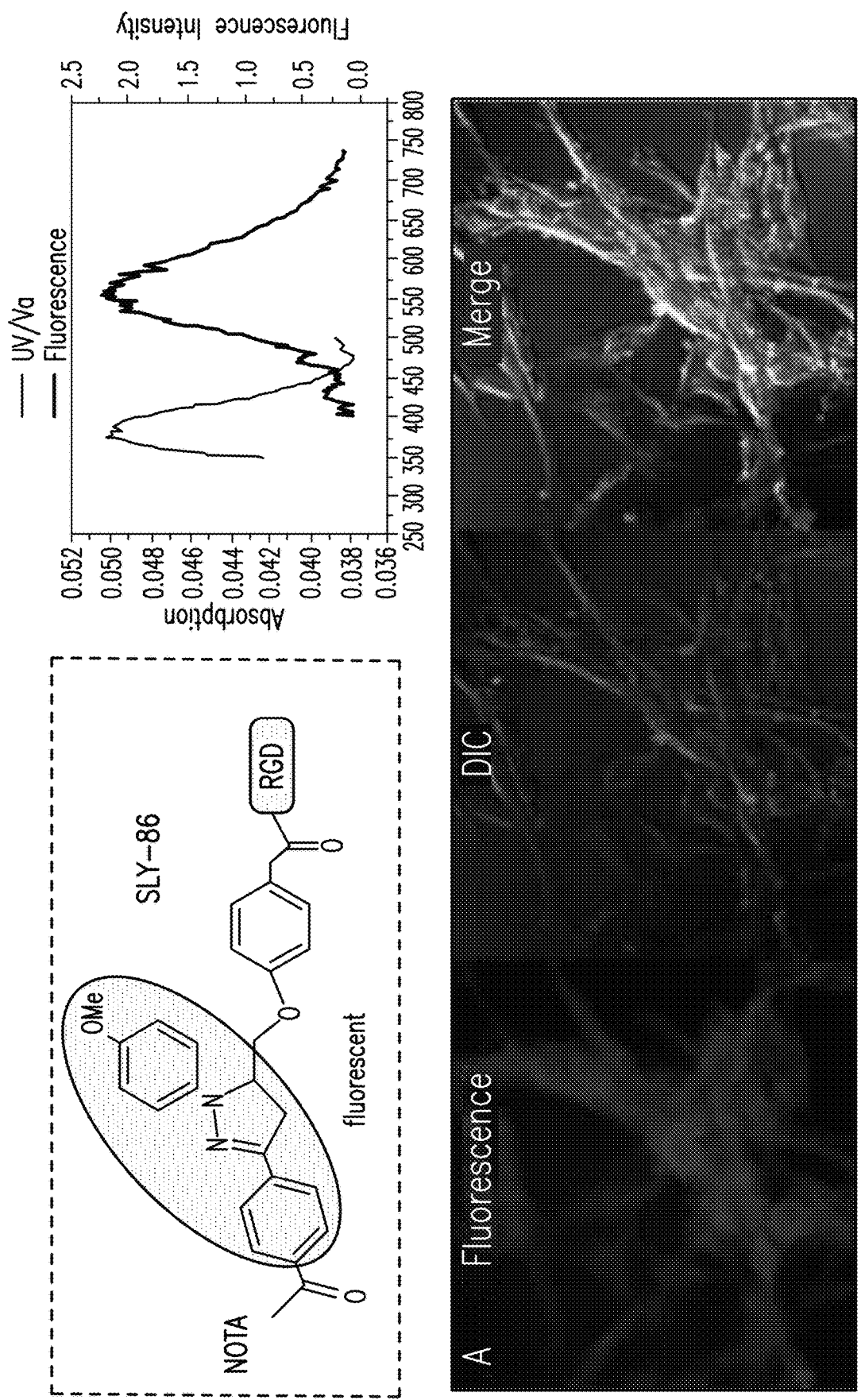

FIG. 10. Diagram of a photoclick product (SLY-86; top left) and its absorption/emission spectra (top right) with confocal fluorescent images demonstrating its interactions with U87MG cells, as described in Example 6.

Figure 11:
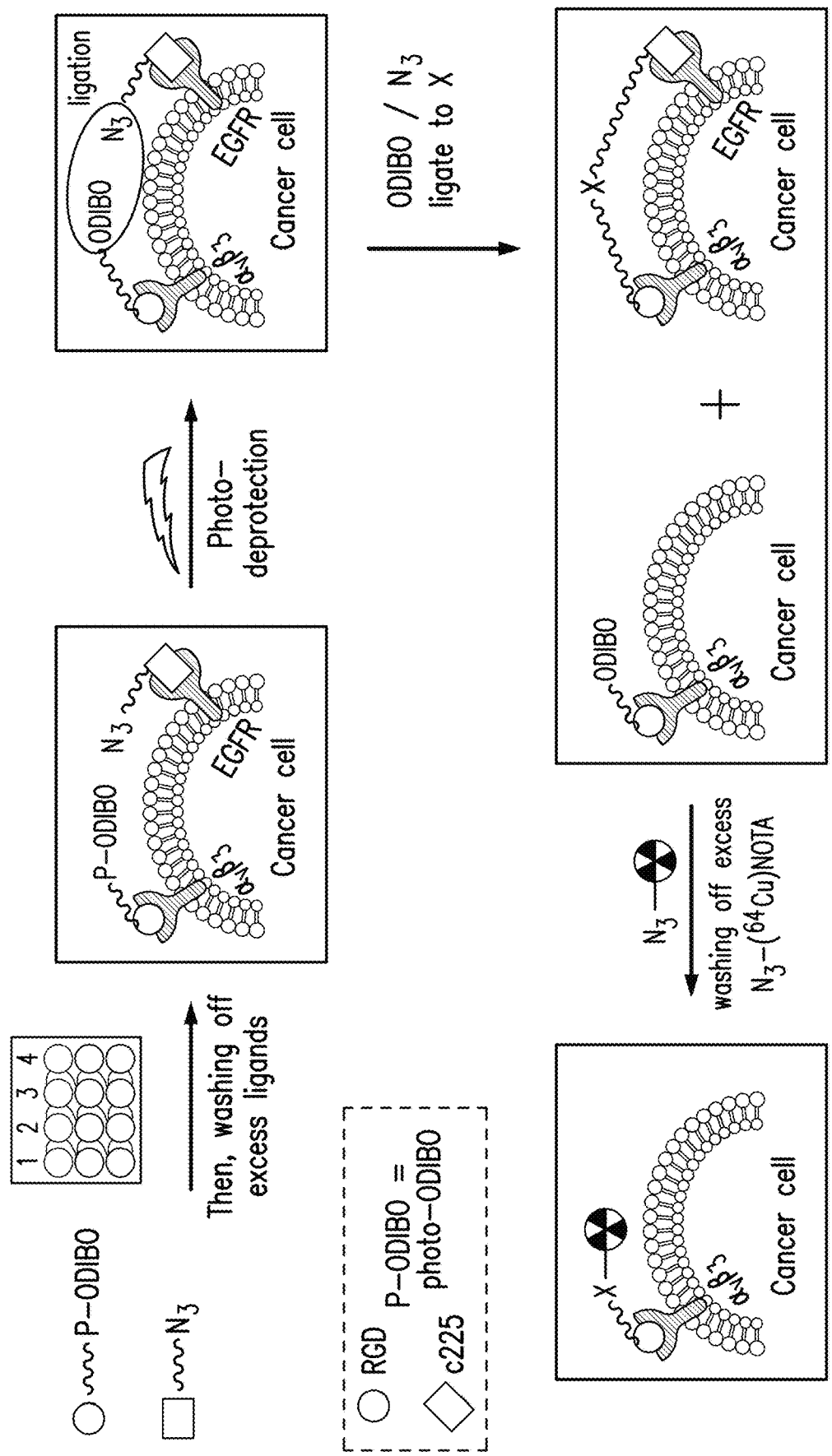

FIG. 11. In vitro spacer optimization platform for heterodimers.

Figure 12:
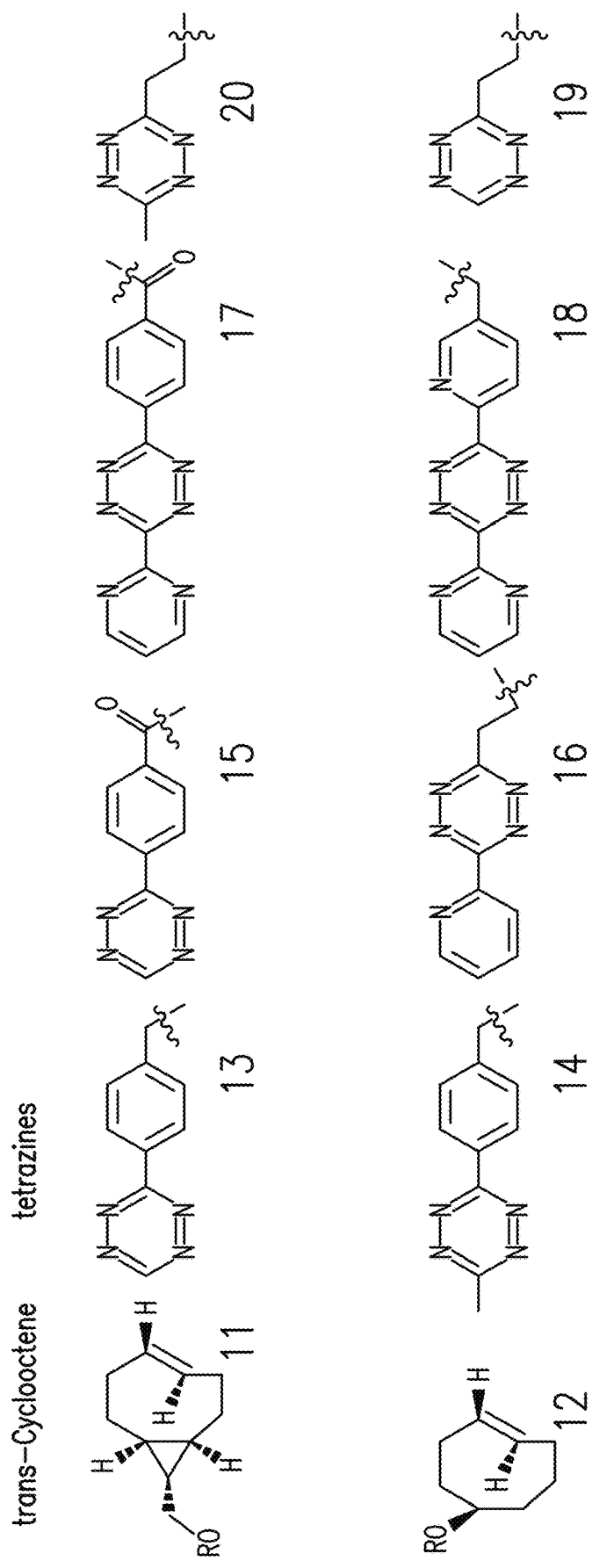

FIG. 12. Various combinations of TCOs and Tzs.

Figure 13:
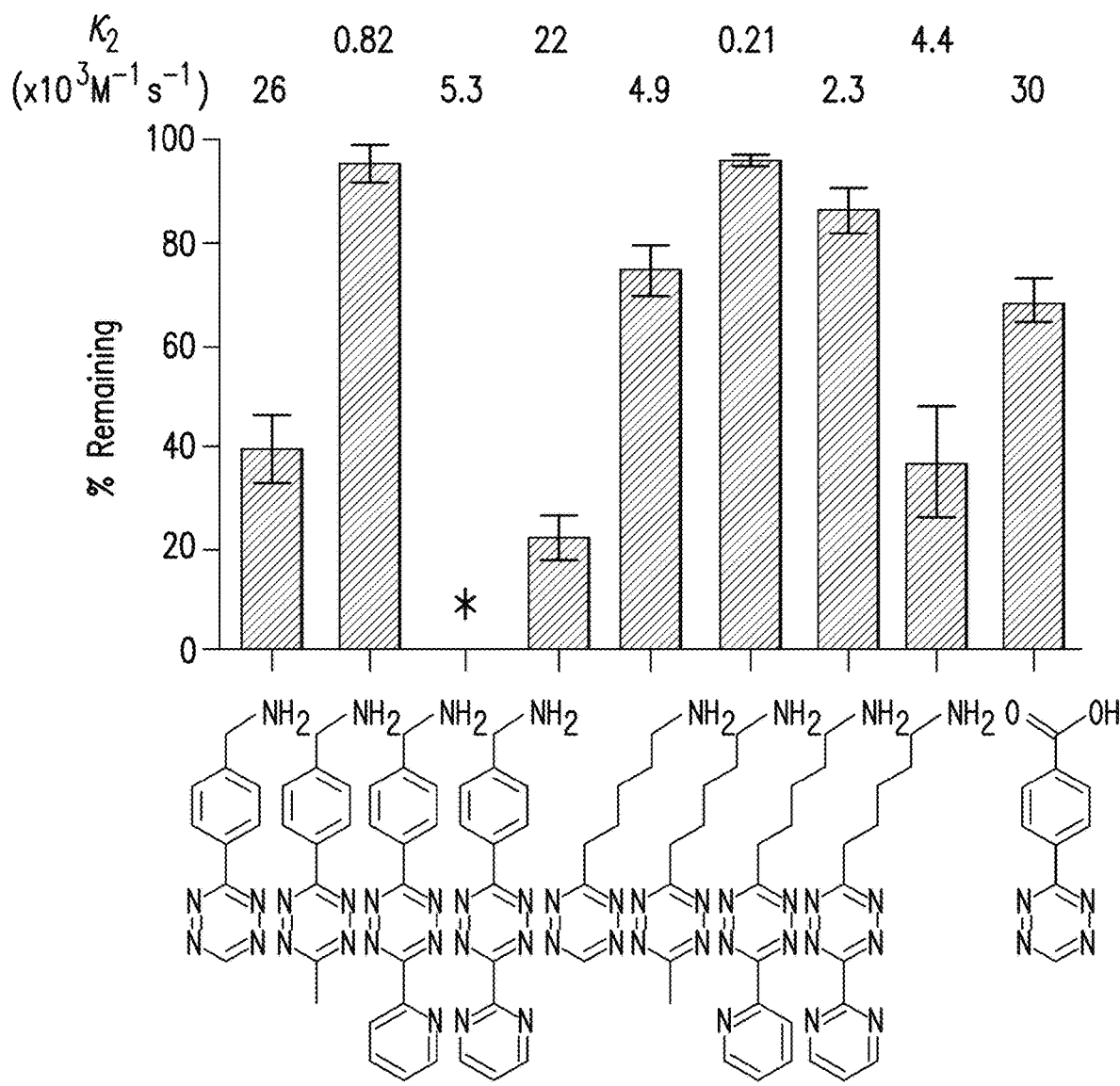

FIG. 13. Kinetics and serum stabilities of Tzs.

Figure 14:
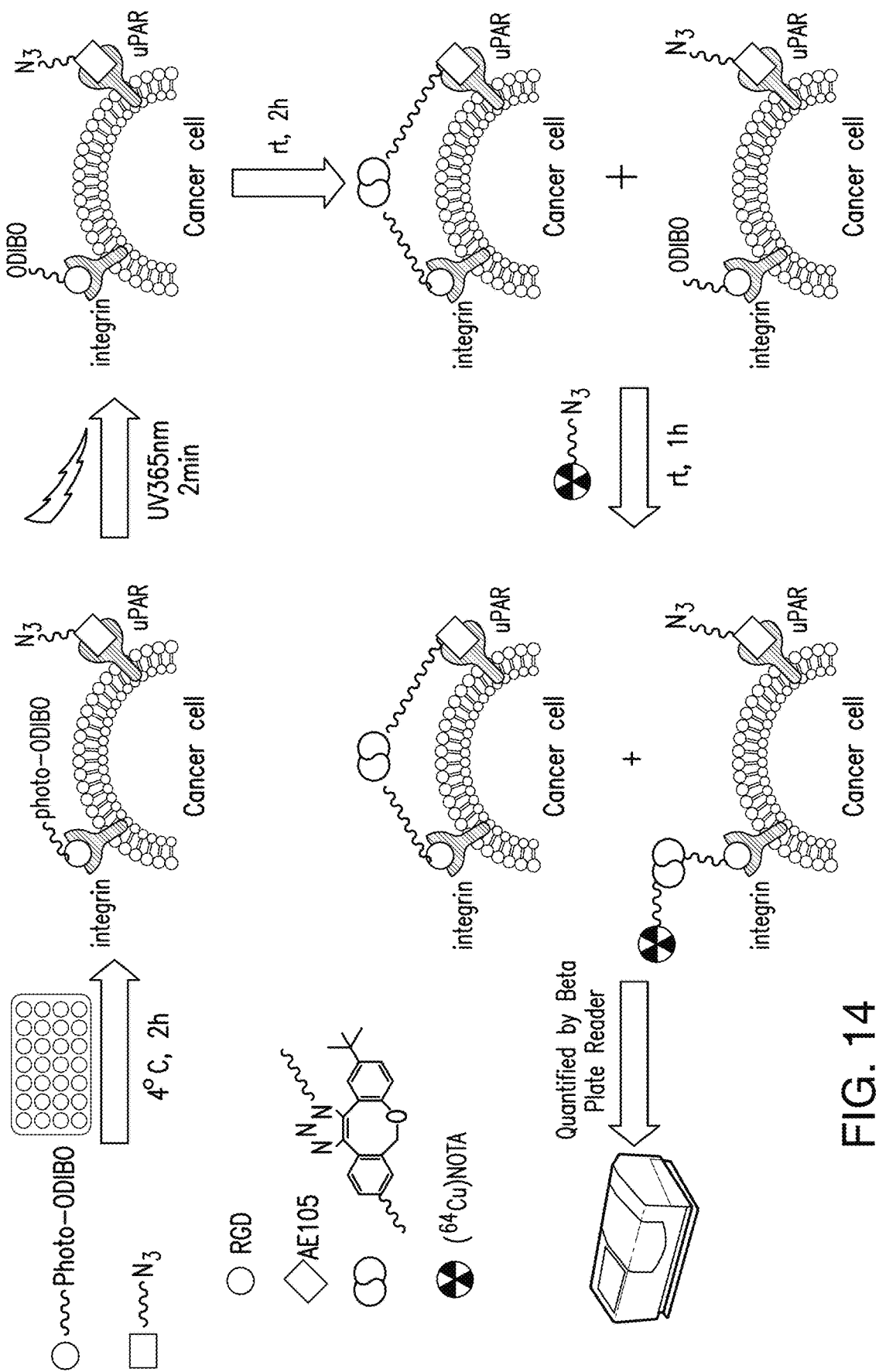

FIG. 14. Schematic illustration of the working rationale of an in vitro screening platform according to the present invention.

Figure 15A:
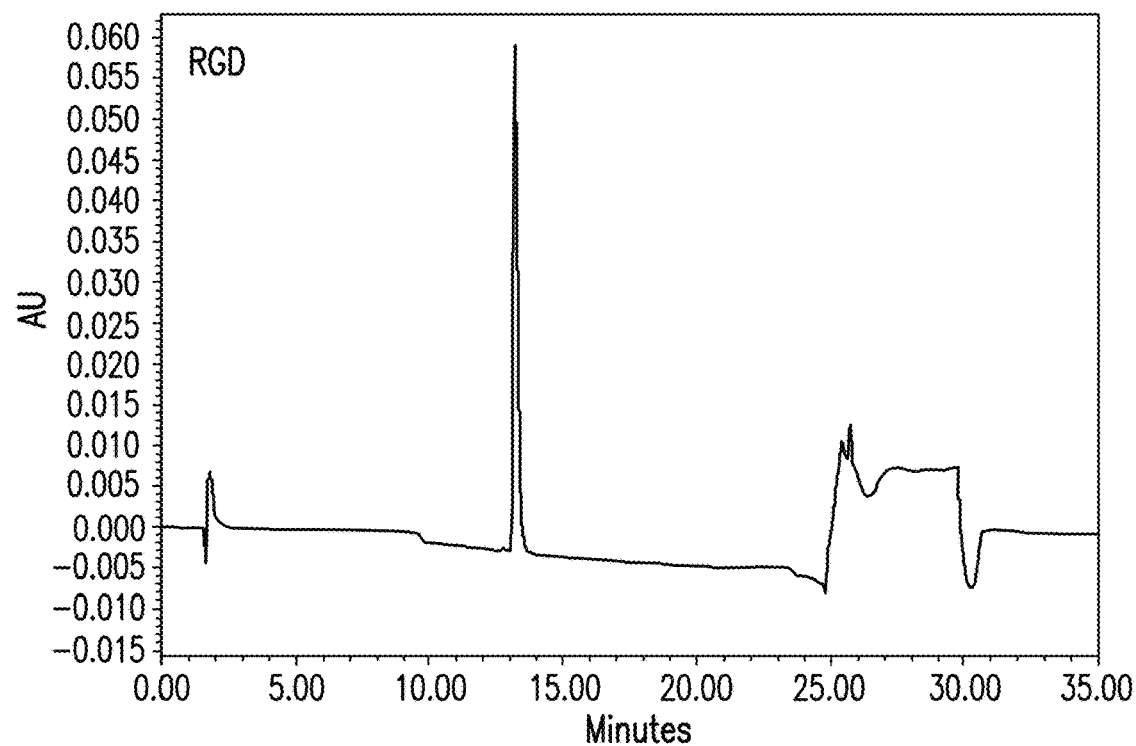
Figure 15B:
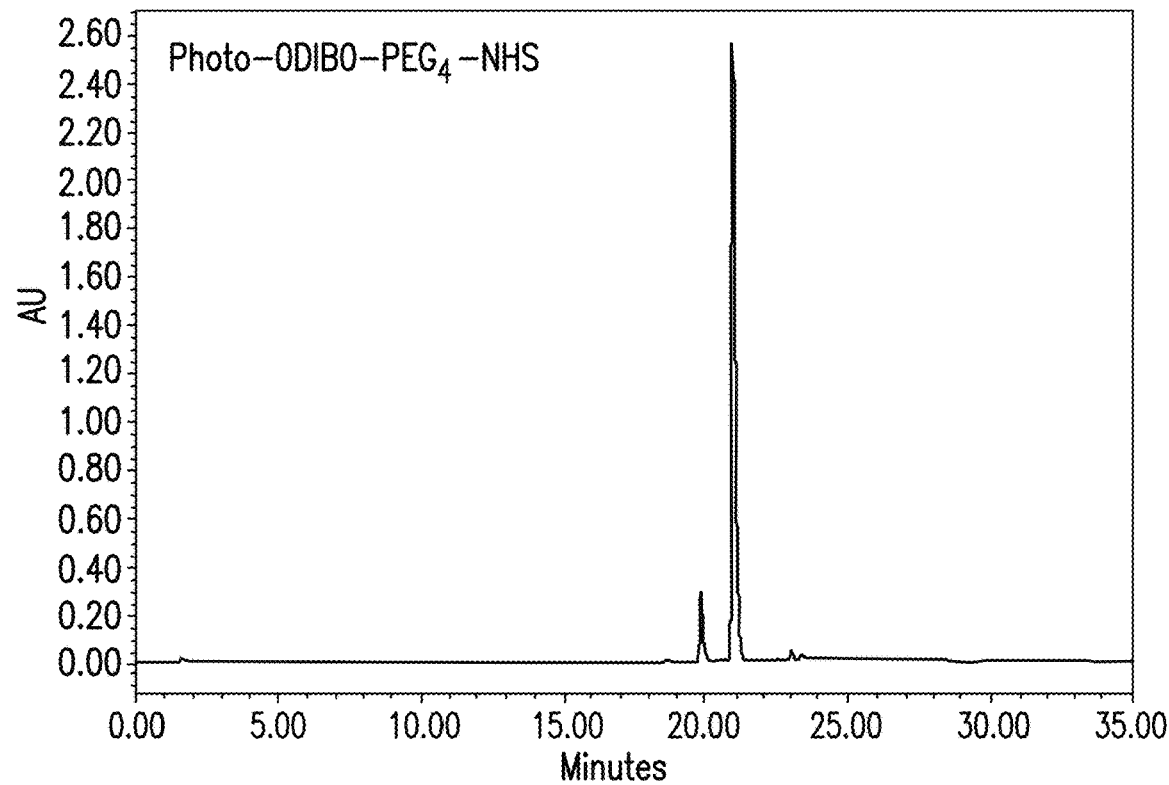

FIG. 15A-FIG. 15D. HPLC monitoring of RGD functionalization. FIG. 15A shows HPLC of RGD. FIG. 15B shows HPLC of Photo-ODIBO-PEG4-NHS.

Figure 15C:
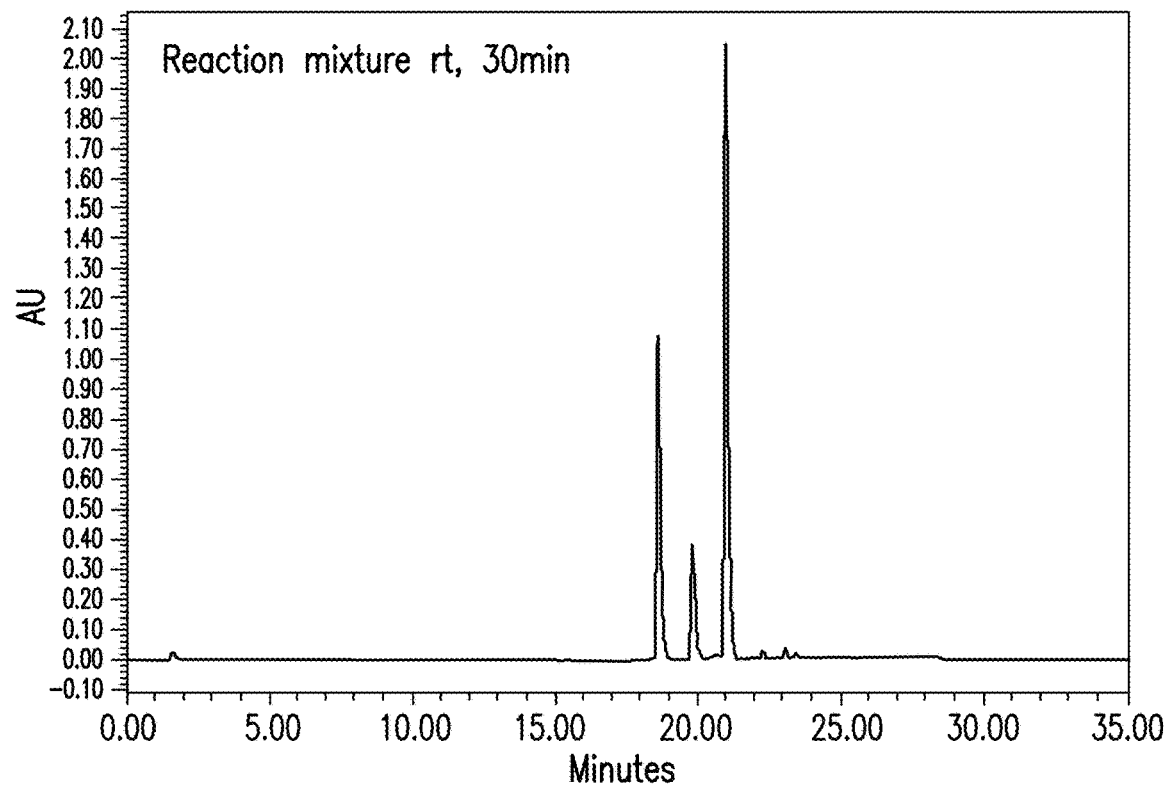
Figure 15D:
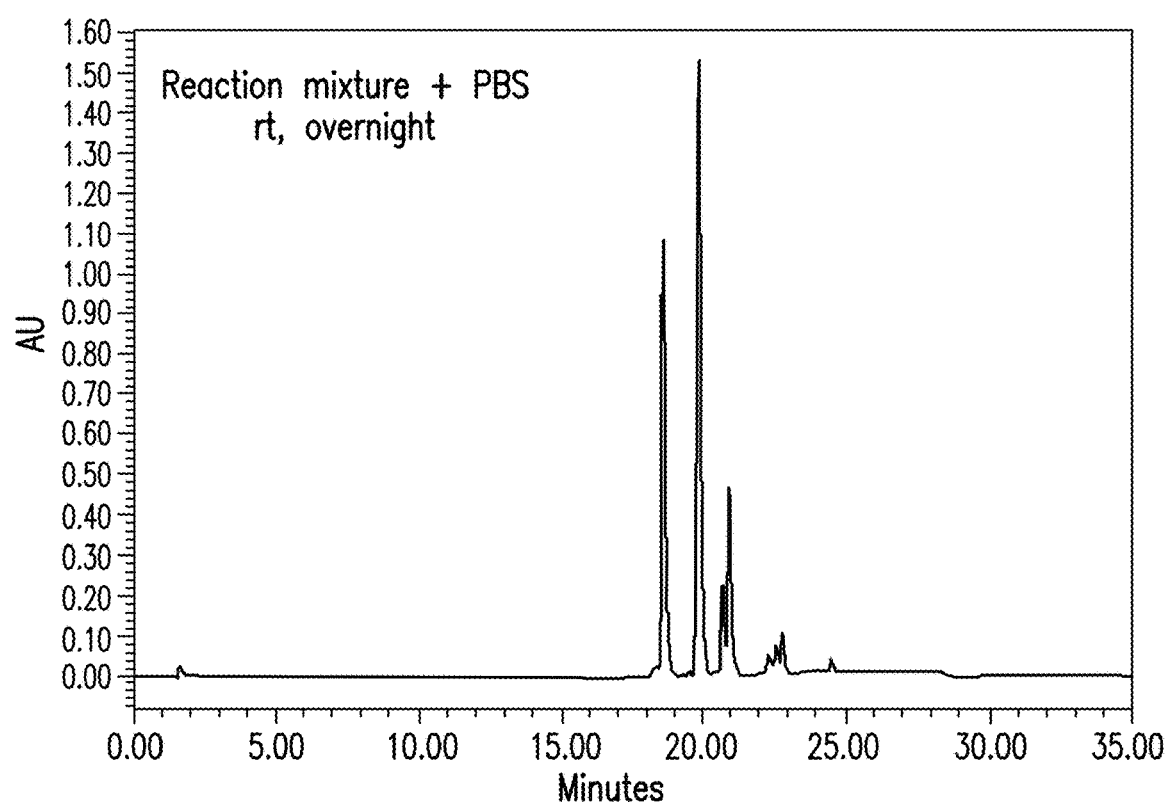

FIG. 15C shows HPLC of the reaction mixture of Example 13 after 30 minutes. FIG. 15D shows HPLC of the reaction mixture of Example 13 after addition of PBS and overnight incubation.

Figure 16:
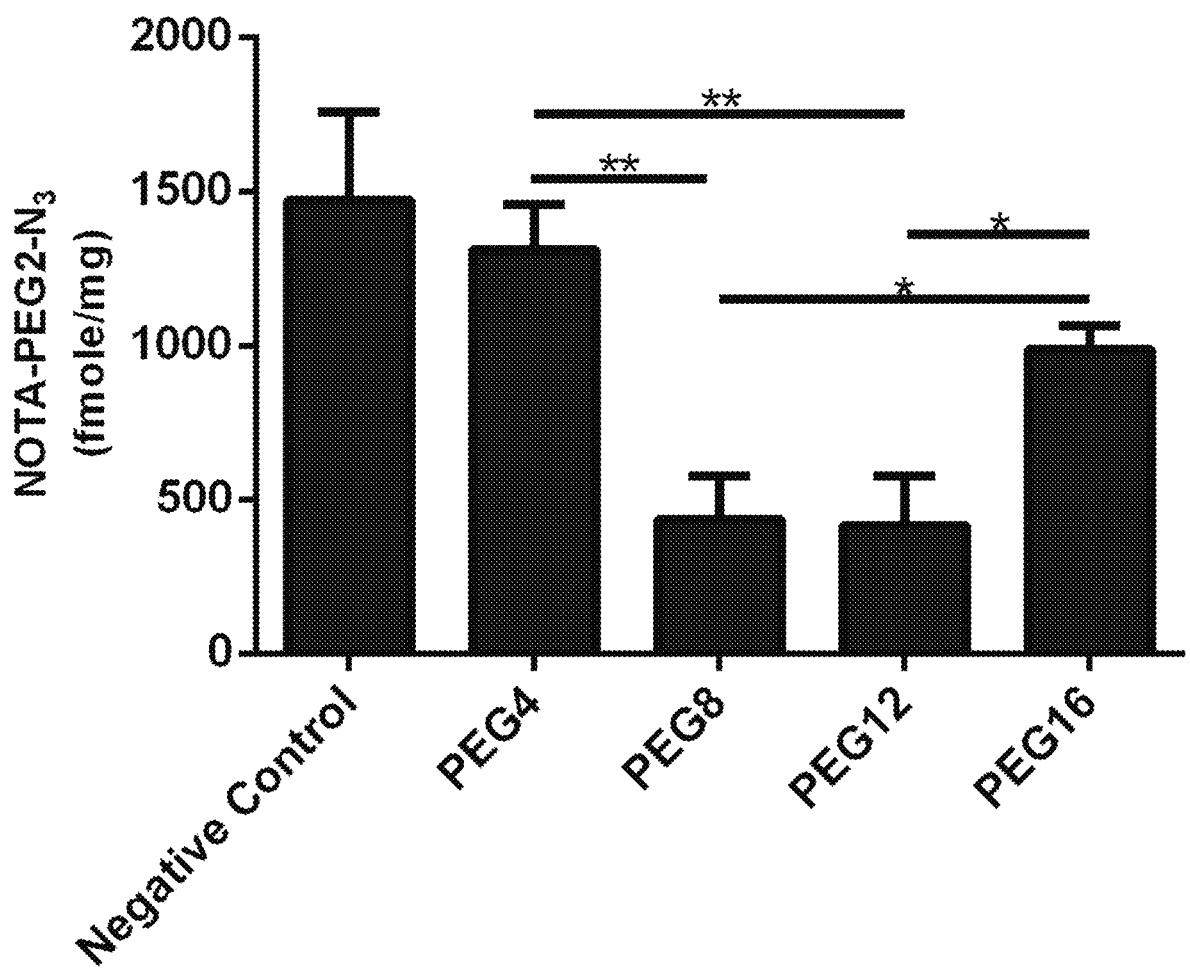

FIG. 16. In vitro screening of selected spacers via the developed platform. (*, P<0.05; **, P<0.01.)

Figure 17A:
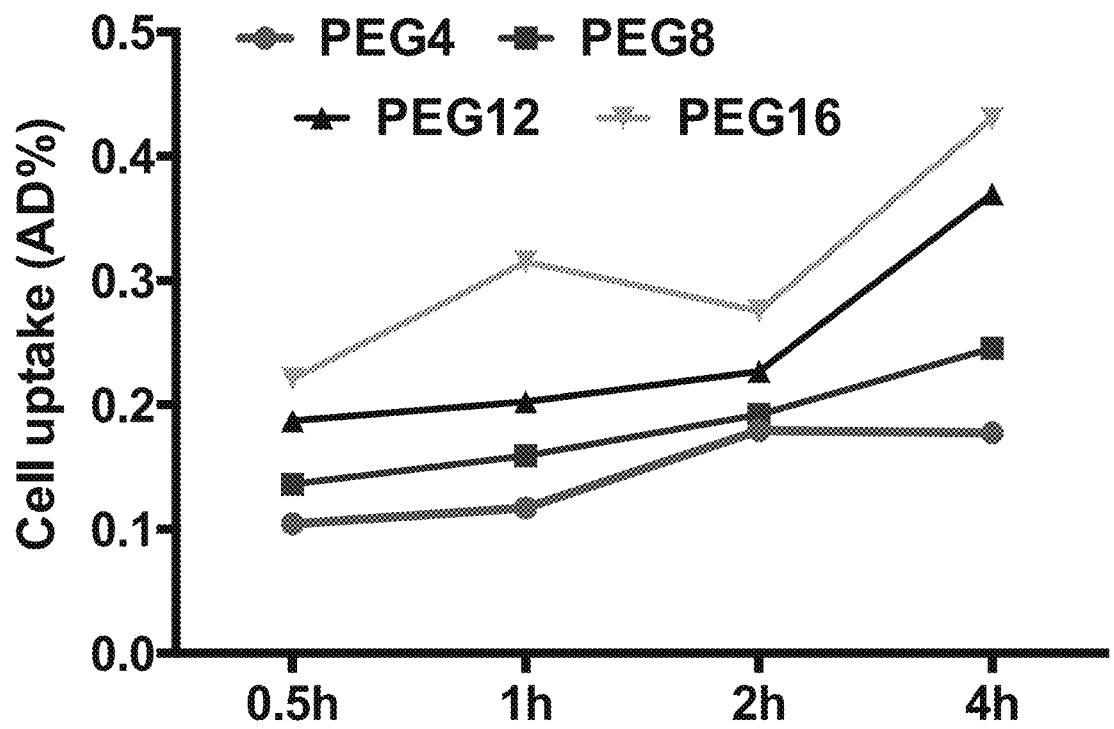
Figure 17B:
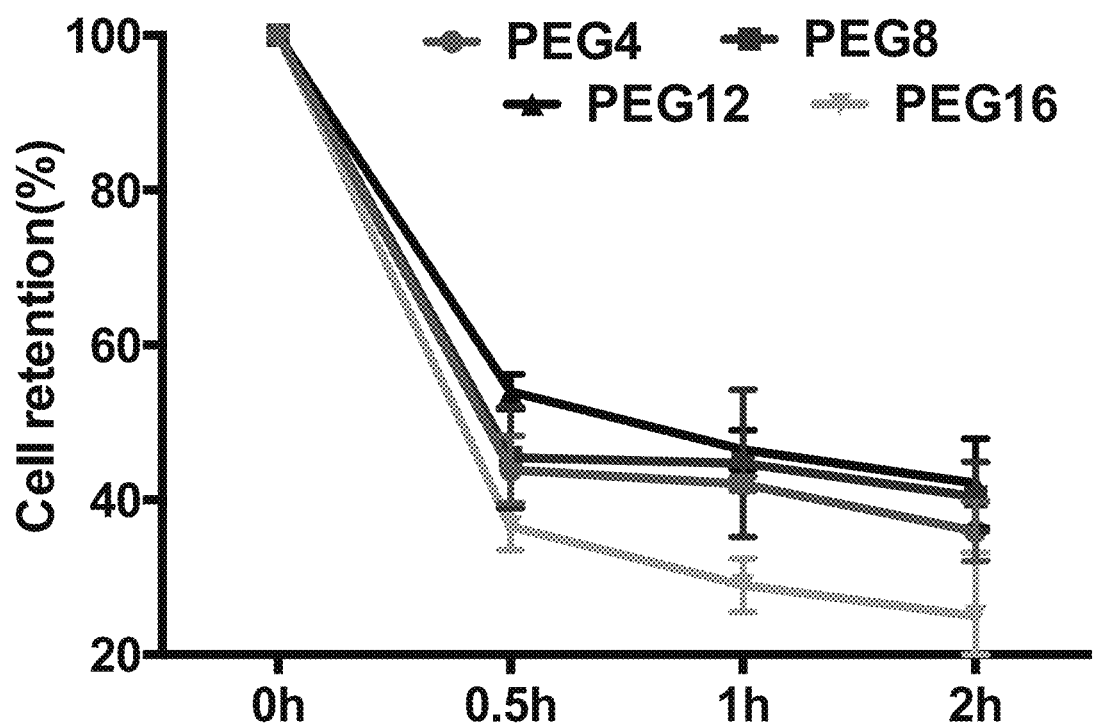

FIG. 17A-FIG. 17B. Cell uptake and efflux studies. FIG. 17A provides results of the cell uptake study for heterodimers with varied spacers according to Example 7. FIG. 17B provides results of the cell efflux study for heterodimers with varied spacers according to Example 7.

Figure 18:
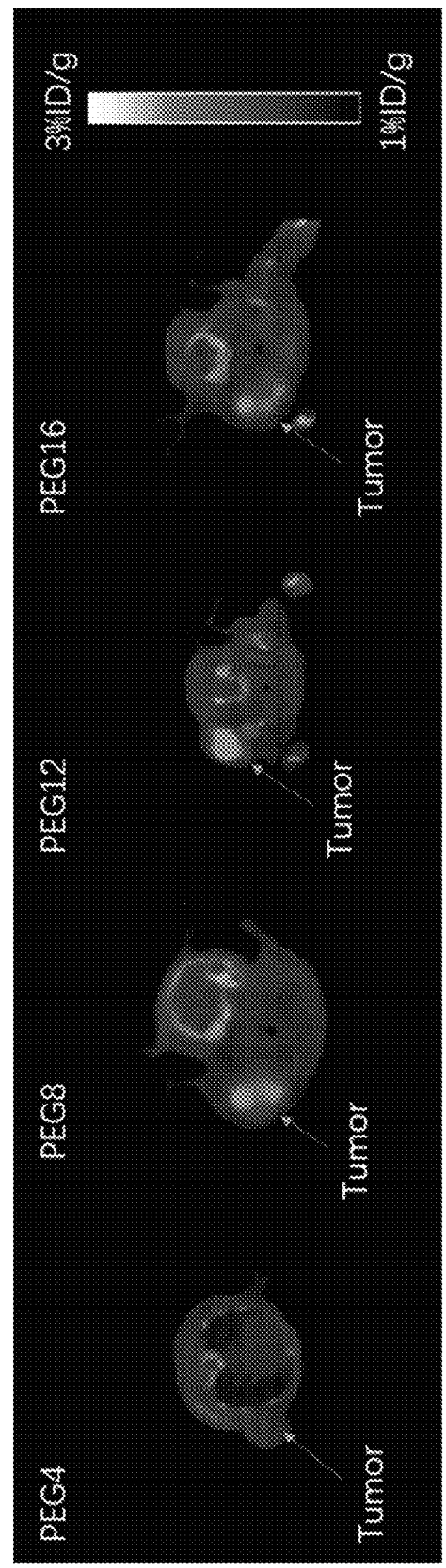

FIG. 18. PET imaging of the u87MG tumor using $Ga^{68}$ labeled heterodimers bearing the same length spacers as selected for the in vitro screening.

Figure 19:
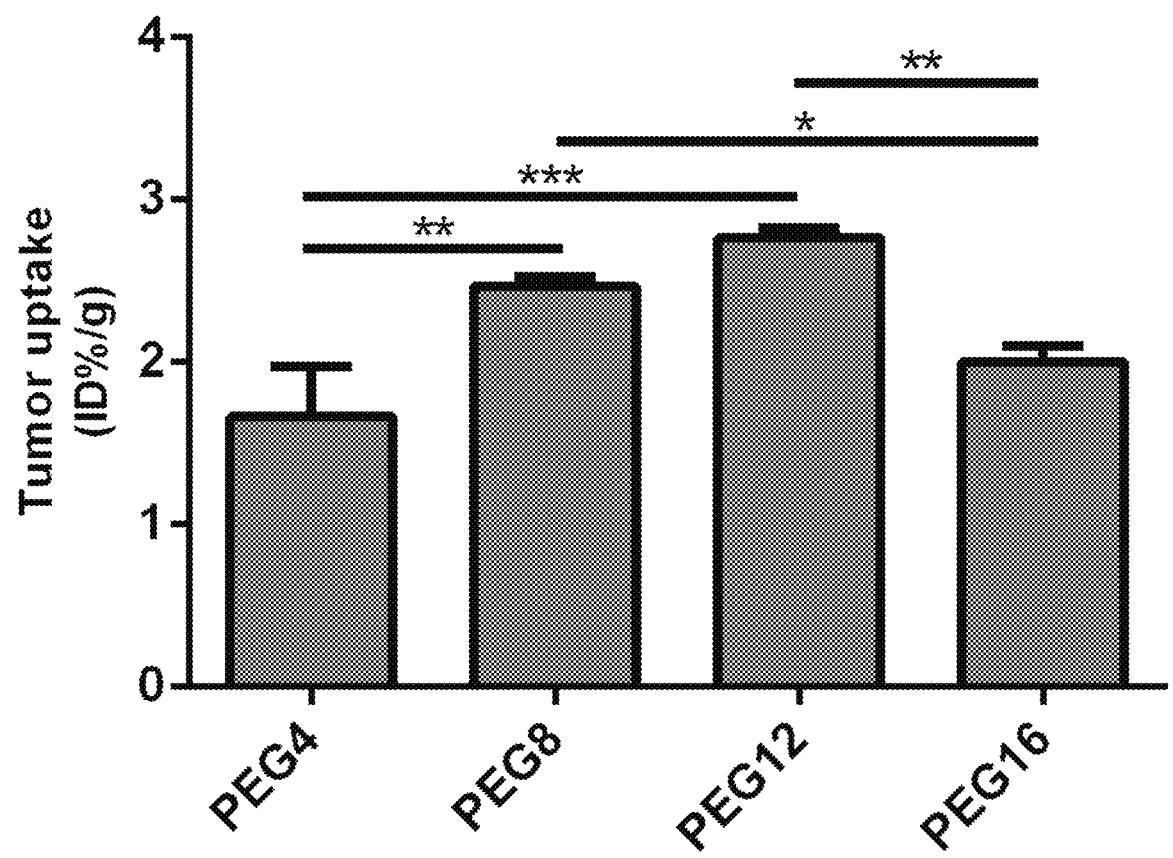

FIG. 19. ROI quantification based on PET images. (*, P<0.05; , P<0.01; * P<0.001).

Figure 20:
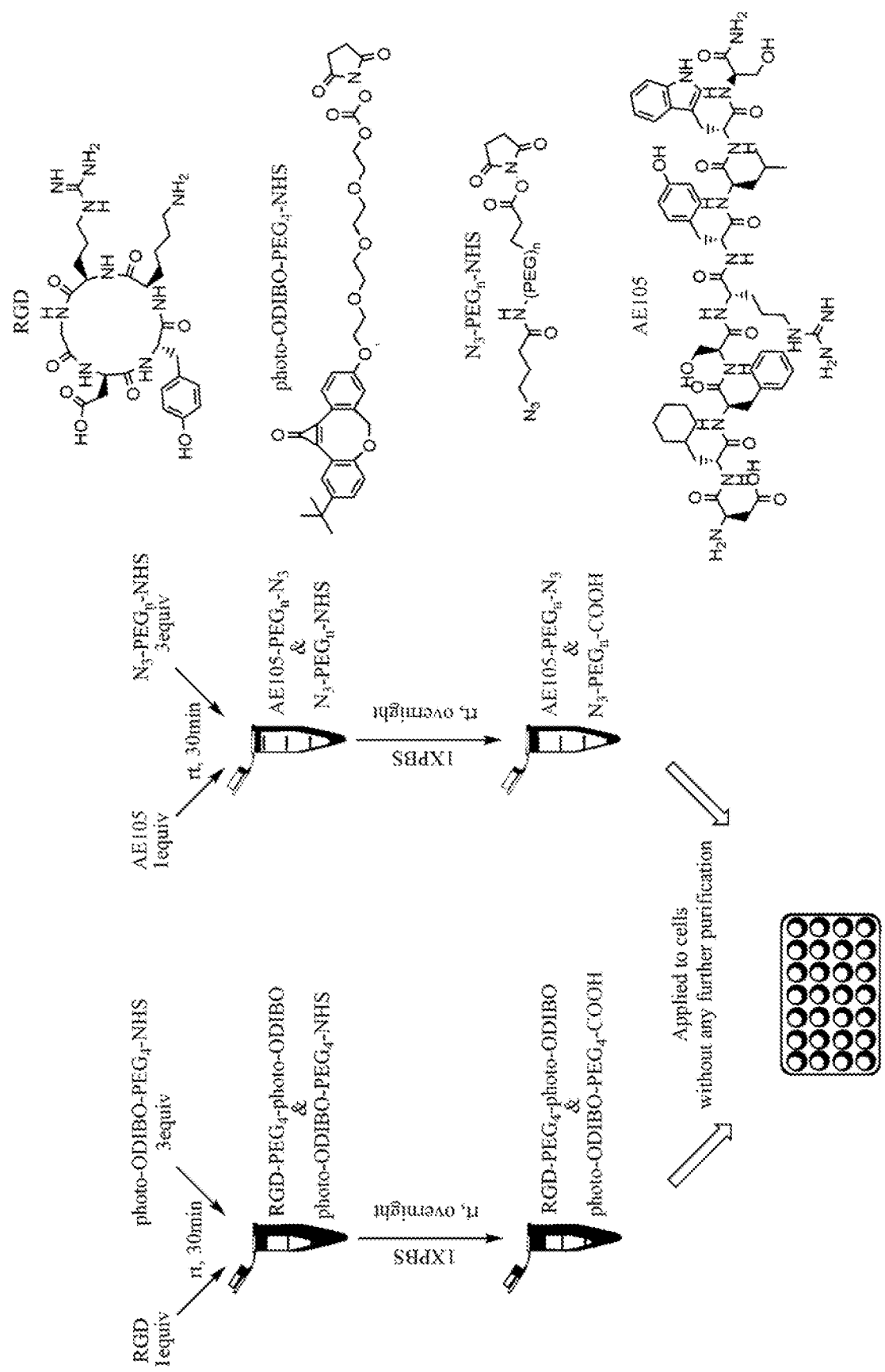

FIG. 20. A schematic of preparation of chemical tools used in the high-throughput screening platform described in Example 8.

Figure 21:
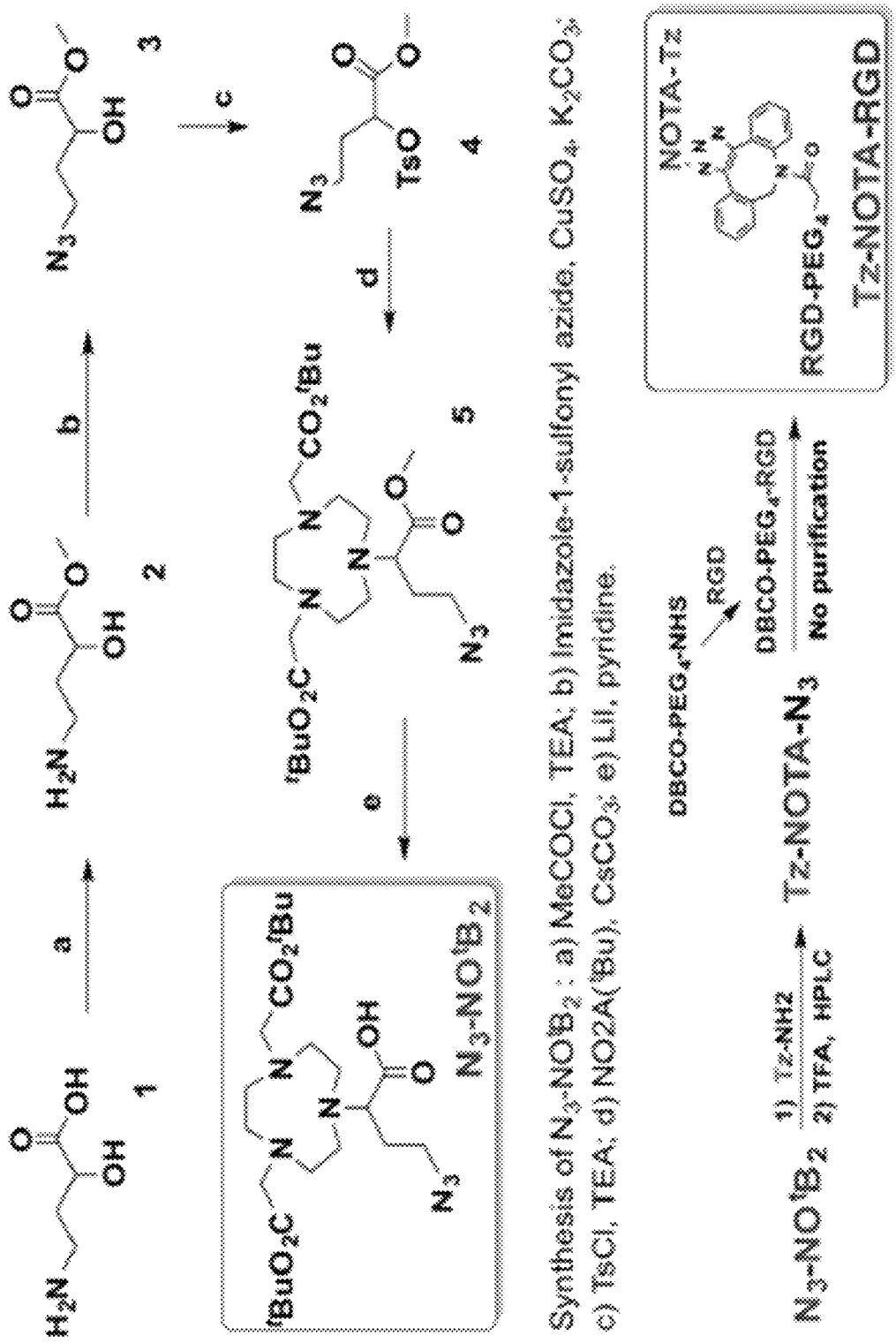

FIG. 21. A schematic of the synthesis of the Dual Receptor Radioactive Molecule chemical tools used in Example 2.

5. DETAILED DESCRIPTION OF THE INVENTION

The present invention provides a method of targeted molecular imaging and/or targeted drug delivery, wherein two components or probes each interacts with biomarkers on a biological subject and separately binds with each other to form a stable bond, e.g., a covalent bond. In certain non-limiting embodiments, the biological subject is a tumor or cancer cell. The present invention also relates to compounds, compositions, probes, and kits for pre-targeted imaging and/or therapy.

In certain non-limiting embodiments, the disclosed targeted molecular imaging and/or targeted drug delivery methods allow for prolonged retention of the fast-clearing detectable label and/or active agent, which consequently increases cellular uptake significantly. In certain non-limiting embodiments, the disclosed methods provide increased sensitivity and/or increased specificity. In certain non-limiting embodiments, the disclosed methods broaden the choice of applicable probes to include both internalizing and non-internalizing probes (e.g., antibodies). In certain non-limiting embodiments, the disclosed targeted molecular imaging and/or targeted drug delivery methods can be broadly applied to various dual-biomarker combinations and targets (e.g., tumors or cancer).

In certain non-limiting embodiments, the methods of the present invention provide a ligation product (i.e., complex) between the first targeting probe and a second targeting probe (caused by the binding of the reactive groups/ligation moieties) that binds more tightly to a cell, tissue, or other structure of interest (e.g., a tumor or cancer cell) relative to a targeting probe linked via a single site, which can result in less non-specific binding and less false positive results. A tighter ligation product can result in smaller amounts of the bound first and second targeting probes dissociating from the biological subject of interest. In certain non-limiting embodiments, the tighter ligation product increases cellular update and/or decreases uptake by non-targeted cells. In the case of tumor cells, achieving high avidity can significantly enhance binding affinity on tumor that overexpresses two targeted biomarkers simultaneously, but not significantly affect the binding affinity on non-tumor tissues that express only one (or none) of the two targeted biomarkers, thus tumor/non-tumor ratio will increase significantly. In certain non-limiting embodiments, by overcoming the over 100-fold dilution of the antibody-targeting radioactive molecule in the circulation in the current pre-targeting strategies, the methods of the present invention provide a higher potential for clinical translation as the targeting ligand incorporated radioactive/drug molecule can accumulate at the site of interest and then continue to be entrapped due to the ligation to the pre-injected slow clearing first targeting probe, thereby increasing the uptake.

The term "pre-targeting approach," refers to a method wherein (i) in a first step a composition that binds to a primary target is administered into a body or in vitro in a cellular system; and (ii) in a second step a labeled composition that binds specifically to the composition that is bound to the primary target is administered. The current invention provides an alternative to the known pre-targeting approach.

The term "pre-targeting ligand", as used herein, refers to compound having a first reactive group and a compound having a second reactive group, respectively. The reactive groups react with one another to form a linkage, such as a covalent linkage, and thereby yield a complex. The reaction of reactive groups varies with each pair of reactive groups. Bioorthogonal ligands are non-limiting examples of pre-targeting ligands. Examples of pre-targeting ligand reactive groups are discussed in greater detail below.

The term "bioorthogonal ligand", as used herein, refers to compound having a first bioorthogonal ligation moiety and a compound having a second bioorthogonal ligation moiety, respectively. Reactive groups, ligating, and ligation moieties are used interchangeably. The bioorthogonal ligation moieties react with one another to form a linkage, such as a covalent linkage, and thereby yield a bioorthogonal complex or complex. The reaction of bioorthogonal ligation moieties varies with each pair of bioorthogonal ligation moieties. Examples of bioorthogonal ligation moieties are discussed in greater detail below.

The term "biomarker", as used herein, refers to a marker (e.g., including but not limited to proteins (including monomeric and multimeric proteins, glycoproteins, lipoproteins, etc.), carbohydrates, lipids, nucleic acids and combinations thereof) that allows detection of a disease or disorder in an individual, including detection of disease or disorder in its early stages. Diseases or disorders include but are not limited to disorders of proliferation, including but not limited to cancers, autoimmune conditions, degenerative conditions, vascular disorders, neurological disorders, and infectious diseases; biomarkers associated with numerous diseases and disorders in human and nonhuman animals are known in the art. In certain non-limiting embodiments, the presence or absence of a biomarker is determined by imaging. In certain non-limiting embodiments, the presence or absence of a biomarker in a biological sample of a subject is compared to a reference control.

The term "active agent" refers to an agent that is capable of having a physiological effect when administered to a subject. In certain embodiments, the term "active agent" refers to a protein, peptide, small molecule, or radiopharmaceutical. In certain non-limiting embodiments, the active agent is a chemotherapeutic agent. In certain non-limiting embodiments, the active agent is an immunotherapeutic agent.

The term "therapeutically effective amount", as used herein, refers to that amount of active agent sufficient to treat, prevent, or manage a disease. Further, a therapeutically effective amount with respect to the second targeting probe of the disclosure can mean the amount of active agent alone, or in combination with other therapies, that provides a therapeutic benefit in the treatment or management of the disease, which can include a decrease in severity of disease symptoms, an increase in frequency and duration of disease symptom-free periods, or a prevention of impairment or disability due to the disease affliction. The term can encompass an amount that improves overall therapy, reduces or avoids unwanted effects, or enhances the therapeutic efficacy of or synergies with another therapeutic agent.

The term "biological subject", as used herein, refers to, but is not limited to, a protein, virus, cell, tissue, organ or organism. In certain non-limiting embodiments, the biological subject can be a normal or diseased or degenerated or infected cell, tissue, or organ. In certain non-limiting embodiments, the cell can be a tumor or cancer cell.

Ranges disclosed herein, for example "between about X and about Y" are, unless specified otherwise, inclusive of range limits about X and about Y as well as X and Y For clarity of description, and not by way of limitation, the detailed description of the invention is divided into the following subsections:
  (i) methods of dual-receptor pre-targeted molecular imaging;
  (ii) methods of photo-triggered dual-receptor pre-targeted molecular imaging;
  (iii) biomarkers;
  (iv) targeting probes; and
  (iv) kits.

5.1. Methods of Dual-Receptor Pre-Targeted Molecular Imaging and/or Drug Delivery The present invention provides a method of targeted molecular imaging and/or targeted drug delivery. In certain non-limiting embodiments, the disclosed methods provide two components or probes that each interacts with at least one biomarker on a cell and that separately bind with each other to form a stable bond, e.g., covalent bond. As embodied herein, the targeting can be achieved using a detectable label, i.e., present on a first targeting probe and/or second targeting probe.

In certain non-limiting embodiments, the methods comprise administering at least one first targeting probe to a subject, wherein the at least one first targeting probe includes a primary targeting moiety and a complexing target. For example, the primary targeting moiety can bind to a biomarker of the cell, tissue, or structure.

In certain non-limiting embodiments, the methods comprise administering at least one second targeting probe to a subject, wherein the at least one second targeting probe includes a secondary targeting moiety, a tertiary targeting moiety, and a detectable label. In certain non-limiting embodiments, the methods comprise administering at least one second targeting probe, wherein the at least one second targeting probe includes a secondary targeting moiety, a tertiary targeting moiety, an active agent, and optionally a detectable label. The secondary targeting moiety can bind to the complexing target of the first targeting probe. The tertiary targeting moiety can bind to a biomarker of the cell, tissue, or structure.

In certain non-limiting embodiments, the primary targeting moiety and the tertiary targeting moiety can bind to the same biomarker of the cell, tissue, or structure. Alternatively, the primary targeting moiety and the tertiary targeting moiety can bind to a different biomarker of the cell, tissue, or structure.

The present invention similarly provides method for treating a disease or disorder of a cell, tissue, or structure in a subject in need of such treatment comprising administering at least one first targeting probe comprising a primary targeting moiety and a complexing target to a subject, administering at least one second targeting probe comprising a secondary targeting moiety, a tertiary targeting moiety, and a detectable label to the subject, and imaging the detectable label.

FIG. 2 is a non-limiting example of a dual-receptor pre-targeted molecular imaging and/or drug delivery method. In FIG. 2, R1-mAb is anon-limiting example of a first targeting probe comprising the complexing target (R1), and R2-radionuclide-targeting ligand is a non-limiting example of a second targeting probe. R2 depicts a secondary targeting moiety that binds to the complexing target (R1). The radionuclide is a non-limiting example of a detectable label. The targeting ligand depicts a tertiary targeting moiety.

In certain non-limiting embodiments, the primary targeting moiety of first targeting probe and the tertiary targeting moiety of the second targeting probe bind to at least one biomarker of a biological subject of interest. In certain non-limiting embodiments, the first and second targeting probe target the same or different biomarker of a biological subject (e.g., cell) of interest. In certain non-limiting embodiments, if the first and second targeting probes bind two different biomarkers, the biomarkers are expressed on the same cell. Biomarkers are discussed in greater detail below.

In certain non-limiting embodiments, the at least one second targeting probe is administered after the at least one first targeting probe. For example, the second targeting probe can be administered after the target site accumulation and/or concomitant blood clearance. In certain non-limiting embodiments, the at least one first targeting probe and the at least one second targeting probe are administered concurrently—for example, overlapping administration or administration at the same time. Administration can be oral or intravenous but other routes of administration can also be employed, such as, but not limited to, intravitreal, parenteral, nasal, buccal, transdermal, sublingual, intramuscular, rectal, vaginal, etc.

In certain non-limiting embodiments, a second targeting probe can be administered one day to a few weeks after administration of a first targeting probe. In certain non-limiting embodiments, the second targeting probe can be administered within 24 hours, up to and including one day, up to and including two days, up to and including three days, up to and including four days, up to and including five days, up to and including six days, up to and including seven days, up to and including eight days, up to and including nine days, up to and including ten days, up to and including eleven days, up to and including twelve days, up to and including thirteen days, up to and including fourteen days, up to and including fifteen days, up to and including sixteen days, up to and including seventeen days, up to and including eighteen days, up to and including nineteen days, or up to and including twenty days after administration of the first targeting probe. In certain non-limiting embodiments, the second targeting probe can be administered between about one and about two days, between about one and about three days, between about one and about four days, between about one and about five days, between about one and about six days, between about one and about seven days, between about one and about ten days, between about one and about fourteen days, between about one and about twenty days, between about one and about twenty four days, or between about one and about thirty two days after administration of the first targeting probe. The timing in which the second targeting probe can be administered depends on the body clearance and half-life of the first targeting probe.

In certain non-limiting embodiments, after the administration of the second targeting probe, at least one reactive moiety of the complexing target on the first targeting probe binds (e.g., via a covalent bond) to at least one reactive moiety of the secondary targeting moiety of the second targeting probe to form a complex (depicted as X in FIG. 2). The reactive moieties are discussed in greater detail below.

In certain non-limiting embodiments, after the administration of the first and second targeting probe, the subject is imaged. In certain non-limiting embodiments, imaging can be conducted by Positron Emission Tomography (PET), Single Photon Emission Computed Tomography (SPECT), Planar gamma camera, X-ray CT, planar X-ray, Magnetic Resonance Imaging (MRI), optical imager, or other diagnostic imaging technique.

In certain non-limiting embodiments, the subject includes any human or nonhuman animal. In certain embodiments, the subject is a pediatric patient. In certain embodiments, the subject is an adult patient. In certain non-limiting embodiments, nonhuman animal includes, but is not limited to, all vertebrates, e.g., mammals and non-mammals, such as non-human primates, sheep, dogs, cats, rodents, rabbits, horses, cows, chickens, amphibians, reptiles, etc.

5.2. Methods of Photon-Triggered Dual-Receptor Pre-Targeted Molecular Imaging and/or Drug Delivery The present invention provides a method of photon-triggered targeted molecular imaging and/or targeted drug delivery. In certain non-limiting embodiments, the disclosed methods provide two components or probes that each interacts with at least one biomarker on a biological subject and that separately bind with each other to form a stable bond only once the primary targeting probe is exposed to photon irradiation.

In certain non-limiting embodiments, the methods comprise administering at least one first targeting probe, wherein the at least one first targeting probe includes a primary targeting moiety and a complexing target.

In certain non-limiting embodiments, the methods comprise administering at least one second targeting probe, wherein the at least one second targeting probe includes a secondary targeting moiety, a tertiary targeting moiety, and a detectable label. In certain non-limiting embodiments, the methods comprise administering at least one second targeting probe, wherein the at least one second targeting probe includes a secondary targeting moiety, a tertiary targeting moiety, an active agent, and optionally a detectable label.

In certain non-limiting embodiments, the primary targeting moiety of the first targeting probe and the tertiary targeting moiety of the second targeting probe bind to at least one biomarker of a biological subject of interest. In certain non-limiting embodiments, the first and second targeting probe target the same or different biomarkers of a biological subject of interest. In certain non-limiting embodiments, if the first and second targeting probes bind two different biomarkers, the biomarkers are expressed on the same cell. Biomarkers are discussed in greater detail below.

In certain non-limiting embodiments, the complexing target of the first targeting probe comprises a photolabile moiety and the secondary targeting moiety of the second targeting probe comprises a moiety that only binds to the photoliable moiety once it has been exposed to photon irradiation.

FIG. 3 is a non-limiting example of a photon-triggered dual-receptor pre-targeted molecular imaging and/or drug delivery method. In FIG. 3, R1-mAb is anon-limiting example of a first targeting probe comprising an unactivated complexing target (R1), and R2-radionuclide-targeting ligand is a non-limiting example a second targeting probe. Once R1 is exposed to photon irradiation it converts from the unactivated complexing target to the activated complexing target (R3). R2 depicts a secondary targeting moiety that binds to the activated complexing target (R3). The radionuclide is a non-limiting example of a detectable label. The targeting ligand depicts a tertiary targeting moiety.

In certain non-limiting embodiments, the at least one second targeting probe is administered after the at least one first targeting probe. For example, the second targeting probe can be administered after the target site accumulation and/or concomitant blood clearance. In certain non-limiting embodiments, the at least one first targeting probe and the at least one second targeting probe are administered concurrently—for example, overlapping administration or administration at the same time. Administration can be oral or intravenous but other routes of administration can also be employed, such as, but not limited to, intravitreal, parenteral, nasal, buccal, transdermal, sublingual, intramuscular, rectal, vaginal, etc.

In certain non-limiting embodiments, after the administration of the first and/or second targeting probe, the target of interest is exposed to photon irradiation. In particular, the second targeting probe is administered after the administration of the first targeting probe, the targeted biomarker is then exposed to photon generated sources (including but not limited to laser and other light sources) for 1 min to a few hours, depending on the size and location of targeted biomarker, to convert the unactivated complexing target (R1) on the first targeting probe to the activated complexing target (R3).

In certain non-limiting embodiments, after photo irradiation, at least one reactive moiety of the complexing target on the first targeting probe binds (e.g., via a covalent bond) to at least one reactive moiety of the secondary targeting moiety of the second targeting probe to form a complex (depicted as X in FIG. 3). The reactive moieties are discussed in greater detail below.

In certain non-limiting embodiments, the accumulation of the second targeting probe can be controlled either temporally and/or spatially by the activation of the unactivated complexing target by photon irradiation. The second targeting probe could be administered one day to a few weeks after administering of the first targeting probe, depending on the body clearance rate of the first targeting probe (see time frames as listed in 5.1). In certain non-limiting embodiments, the second targeting probe could be administered 1 min to a few hours after the photon irradiation that can last for 1 min to a few hours.

In certain non-limiting embodiments, after the administration of the first and second targeting probe, the subject is imaged as discussed above.

In certain non-limiting embodiments, the subject includes any human or nonhuman animal, as discussed above.

5.3. Biomarkers

In certain non-limiting embodiments, the first targeting probe and the second targeting probe target at least one biomarker of a biological subject of interest. In certain non-limiting embodiments, the first and second targeting probe can target the same or different biomarker(s) of a biological subject of interest. In certain non-limiting embodiments, when the first and second targeting probes are directed to two different biomarkers, the biomarkers are expressed on the same cell.

In certain non-limiting embodiments, the biomarker can be expressed on the surface of the cell or internally. In certain non-limiting embodiments, the biomarker can be a cell surface protein, receptor, receptor subunit, tissue-specific antigen, virally derived protein, virally encoded envelope protein, bacterially derived protein, bacterial surface protein, etc. In certain non-limiting embodiments, the biomarker is an integrin.

In certain non-limiting embodiments, the biological subject is a protein, virus, cell, tissue, organ or organism. In certain non-limiting embodiments, the cell can be, but is not limited to, a tumor or cancer cell. In certain non-limiting embodiments, the first and second targeting probe bind to a cell from a tumor or cancer such as, but not limited to, pancreatic cancer, breast cancer, colorectal cancer, NSCLC, lung cancer, bone cancer, skin cancer, cancer of the head or neck, cutaneous melanoma, intraocular melanoma, uterine cancer, ovarian cancer, rectal cancer, anal region cancer, stomach cancer, gastric cancer, colon cancer, breast cancer, uterine cancer, fallopian tube carcinoma, endometrial carcinoma, cervical carcinoma, vaginal carcinoma, vulval carcinoma, Hodgkin's Disease, esophagus cancer, small intestine cancer, endocrine system cancer, thyroid gland cancer, parathyroid gland cancer, adrenal gland cancer, soft tissue sarcoma, urethral cancer, penis cancer, prostate cancer, bladder cancer, kidney cancer, ureter cancer, renal cell carcinoma, renal pelvis carcinoma, mesothelioma, hepatocellular cancer, biliary cancer, chronic leukemia, acute leukemia, lymphocytic lymphoma, CNS neoplasm, spinal axis cancer, brain stem glioma, glioblastoma multiform, astrocytoma, schwannoma, ependymoma, medulloblastoma, meningioma, squamous cell carcinoma and pituitary adenoma tumors, or tumor metastasis. In certain non-limiting embodiments, the cell of interest is a pancreatic cancer cell.

In certain non-limiting embodiments, the biomarker can be epidermal growth factor receptor (EGFR), integrin $\alpha 1\beta 1$, integrin $\alpha 2\beta 1$, integrin $\alpha 3\beta 1$, integrin $\alpha 4\beta 1$, integrin $\alpha 5\beta 1$, integrin $\alpha 6\beta 1$, integrin $\alpha v\beta 3$, uPAR, gastrin-releasing peptide (GRP), SSTR2, SSTR3, SSTR4, SSTR5, Folate receptor, CCR5, CXCR4, plectin-1, VEGF, CA19-9, PD-I1, Her2/neu, 5-alpha reductase, $\alpha$-fetoprotein, AM-1, APC, APRIL, BAGE, $\beta$-catenin, Bcl2, bcr-abl (b3a2), CA 125, CASP-8/FLICE, Cathepsins, CD19, CD20, CD21, CD23, CD22, CD38, CD33, CD35, CD40, CD44, CD45, CD46, CD5, CD52, CD55, CD59 (791Tgp72), CDC27, CDK4, CEA, c-myc, COX-2, Cytokeratin, DCC, DcR3, E6/E7, EGFR, EMBP, Ena78, Estrogen Receptor (ER), FGF8b and FGF8a, FLK 1/KDR, G250, GAGE-Family, gastrin 17, Gastrin-releasing hormone (bombesin), GD2/GD3/GM2, GnRH, GnTV, gp100/Pme117, gp-100-in4, gp15, gp75/TRP-1, hCG, Heparanase, Her3, HMTV, Hsp70, hTERT (telomerase), IGFR1, IL 13R, iNOS, Ki 67, KIAA0205, K-ras, H-ras, N-ras, KSA (CO17-1A), LDLR-FUT, MAGE Family (MAGE1, MAGE3, etc.), Mammaglobin, MAP17, Melan-A/MART-1, mesothelin, MIC A/B, MT-MMP's, such as MMP2, MMP3, MMP7, MMP9, Mox1, Mucin, such as MUC-1, MUC-2, MUC-3, and MUC-4, MUM-1, NY-ESO-1, Osteonectin, p15, P170/MDR1, p53, p97/melanotransferrin, PAI-1, PDGF, Plasminogen (uPA), PRAME, Probasin, Progenipoietin, Progesterone Receptor (PR), PSA, PSM, RAGE-1, Rb, RCAS1, SART-1, SSX gene family, STAT3, STn (mucin assoc.), TAG-72, TGF-$\alpha$, TGF-$\beta$, Thymosin $\beta$-15, IFN-$\gamma$, TPA, TPI, TRP-2, Tyrosinase, VEGF, ZAG, p161NK4, Myo D1, Glutathione and S-transferase. In certain non-limiting embodiments, the biomarker can be epidermal growth factor receptor (EGFR), integrin $\alpha v\beta 3$, uPAR, gastrin-releasing peptide (GRP), SSTR2, Folate receptor, CCR5, CXCR4, integrin $\alpha 4\beta 1$, plectin-1, VEGF, MUC4, CA19-9, CD40 or PD-I1. In certain non-limiting embodiments, the biomarker is EGFR and/or integrin $\alpha v\beta 3$.

As both $\alpha v\beta 3$ and EGFR are overexpressed in many different types of tumors, the combination of $\alpha v\beta 3$/EGFR can be used to image and/or treat various different types of tumors or cancer.

5.4. Targeting Probes

The present invention provides two components or probes that each interacts with at least one biomarker on a biological subject and that separately interact with each other to form a stable bond, e.g., a stable covalent bond. Thus, in certain non-limiting embodiments, the present invention provides a composition comprising a primary targeting moiety and a complexing target (e.g., from a first targeting probe) and a secondary targeting moiety, a tertiary targeting moiety, and a detectable label (e.g., from a second targeting probe).

5.4.1. First Targeting Probes

The present invention provides for use of at least one first targeting probe. In certain non-limiting embodiments, the first targeting probe comprises a primary targeting moiety and a complexing target. In certain non-limiting embodiments, the first targeting probe comprises a primary targeting moiety and an unactivated complexing target.

In certain non-limiting embodiments, the first targeting probe can be an antibody, protein, peptide, small molecule, nanoparticle, polysaccharide, or polynucleotide that binds to the biomarker. In certain non-limiting embodiments, the first targeting probe is an antibody. The term "antibody" as used herein, includes, but is not limited to antibodies, antibody derivatives, organic compounds derived there from, monoclonal antibodies, antibody fragments, modified antibodies, single chain antibodies and fragments thereof and miniantibodies, bispecific antibodies, diabodies, triabodies, or di-, oligo- or multimers thereof. In certain non-limiting embodiments, modified antibodies includes synthetic antibodies, chimeric or humanized antibodies, or mixtures thereof, or antibody fragments which partially or completely lack the constant region, e.g., Fv, Fab, Fab' or F(ab)'2 etc. In certain embodiments, the antibody is a monoclonal antibody. In certain non-limiting embodiments, the first targeting probe can be internalizable or non-internalizable.

In certain non-limiting embodiments, the antibodies are commercially available. In certain non-limiting embodiments, an antibody can be made against a specific biomarker by any technique understood by those of skill in the art.

In certain non-limiting embodiments, the complexing target comprises a reactive moiety. In certain non-limiting embodiments, the complexing target is a bioorthogonal ligand with a bioorthogonal ligation moiety, such as, but not limited to trans-cycloocten, tetrazine, cyclooctyne, alkyne, azide, alkene, tetrazole, photo-DIBO and cyclopropenones. Photo active moieties are the precursor of tetrazole and photo-DIBO. Non-limiting examples of possible trans-cyclooctenes and tetrazines are shown in FIG. 12. FIG. 13 also shows the kinetics and serum stabilities of various azides. The combination of bioorthagonal ligands can be selected based on the needs of the target.

In certain non-limiting embodiments, the complexing target is attached, preferably by a covalent bond, to the first targeting probe via a spacer. In certain non-limiting examples, the spacer can be a polymer or a biomolecule. In certain non-limiting embodiments, the polymer can be synthetic or natural. In certain non-limiting examples, the polymer can be polyethylene glycol (PEG). For example, the polymer can have a molecular weight of about 40 Da, about 40 Da, about 100 Da, about 200 Da, about 300 Da, about 400 Da, about 1.00 Da, about 10,000 Da, about 25,000 Da, about 30,000 Da, about 35,000 Da, or about Da 40,000, or for further example, from about 40 Da to about 100,000 Da, from about 200 Da to about 100,000 Da, or from about 10,000 Da to about 100,000 Da, or from about 25,000 to about 100,000 Da, or from about 25,000 Da to about 50,000 Da. For further example, the polymer can be polyacrylic acid; hydroxyethyl starch (HES); poly lactide-co-glycolide; poly-D, L-p-dioxanonepoly lacticacid-ethylene glycol block copolymer (PLA-DX-PEG); poly (ortho) esters; poly-glutamate; polyaspartates; a polymer of α-β-unsaturated monomers, such as (meth) acrylic acid, crotonic acid, maleic acid, maleic anhydride, fumaric acid, itaconic acid or anhydride, etc.; a comonomer comprising vinyl ethers, vinyl esters, vinylamine amides, olefins, diallyl dialkyl ammonium halides, preferably vinyl ether; poly (diethylenglycoladipat); polyethyleneimine; polyglycolide; polyurea; Polylimonen (or Polylimo); poly (2-methyl-1, 3-propylene adipate); a graft polymer; graft (block) polymer with other polymers. In certain non-limiting embodiments, the polymer is linear, branched, or dendrimic. In certain non-limiting embodiments, the polymer is PEG. In certain non-limiting embodiments, the PEG spacer can have a molecular weight of about 200 Da to about 20 kDa.

In certain non-limiting embodiments, the polymer comprises at least one subunit (e.g., in the case of a PEG polymer, one subunit is ethylene oxide). In certain embodiments, the first targeting probes have the same number of polymer subunits. In certain embodiments, the first targeting probes have different numbers of polymer subunits. In certain non-limiting embodiments, the polymer can comprise between about 1 to about 30 subunits. In certain non-limiting embodiments, the polymer can comprise between about 1 to about 20, between about 2 to about 19, between about 3 to about 18, between about 4 to about 17, between about 5 to about 16, between about 6 to about 15, between about 7 to about 14, between about 8 to about 13, between about 9 to about 12, or between about 10 to about 11 subunits. In certain non-limiting embodiments, the polymer can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 55, at least 26, at least 27, at least 28, at least 29, or at least 30 subunits. In certain non-limiting embodiments, the polymer can comprise between about 1 to about 6, between about 2 to about 5, or between about 3 to about 4 subunits. In certain non-limiting embodiments, the polymer can comprise about 1, about 2, about 3, about 4, about 5, about 6, about 7, about 8, about 9, about 10, about 11 about, 12, about 13, about 14, about 15, about 16, about 17, about 18, about 19, or about 20 subunits. In certain non-limiting embodiments, the polymer can comprise about 4 subunits. In certain non-limiting examples, 2, 4, 6, 8, 10, 12, 14, or 16 polymer subunits can be used.

In certain non-limiting embodiments, the first targeting probes have at least one complexing target. In certain embodiments, the first targeting probes have 2~50 of the same repeating complexing target. In certain embodiments, the first targeting probes have 2~50 different kinds of complexing targets (e.g., combinations of PEG, PLA, and other polymers). In certain non-limiting embodiments, the 2~50 complexing targets are each attached to the first targeting probe with separate spacers. In certain non-limiting embodiments, the 2~50 complexing targets are attached to the first targeting probe with a single branched polymer.

5.4.2. Second Targeting Probes

The present invention provides for use of at least one second targeting probe. In certain non-limiting embodiments, the second targeting probe comprises a secondary targeting moiety, a tertiary targeting moiety, and a detectable label. In certain non-limiting embodiments, the second targeting probe comprises a secondary targeting moiety, a tertiary targeting moiety, an active agent, and optionally a detectable label. In certain embodiments, the active agent can be the tertiary targeting moiety.

In certain non-limiting embodiments, the second targeting probe can be an antibody, protein, peptide, small molecule, nanoparticle, polysaccharide, or polynucleotide that binds to the biomarker. In certain non-limiting embodiments, the second targeting probe is an antibody as outlined above for the first targeting probe. In certain non-limiting embodiments, the second targeting probe can be intemalizable or non-internalizable.

In certain non-limiting embodiments, the secondary targeting probe comprises a reactive moiety. In certain non-limiting embodiments, the secondary targeting moiety is a bioorthogonal ligand with a bioorthogonal ligation moiety, such as, but not limited to trans-cyclooctene, tetrazine, cyclooctyne, alkyne, or azide, alkene, tetrazole, or cyclopropenones. See FIG. 12 for non-limiting examples of bioorthogonal ligands.

In certain non-limiting embodiments, the secondary targeting moiety is attached, preferably by a covalent bond, to the second targeting probe via a spacer. In certain non-limiting examples, the space can be a polymer or a biomolecule as outlined above.

In certain non-limiting embodiments, the detectable label is attached to the second targeting probe via a spacer. In certain non-limiting examples, the spacer can be a polymer or a biomolecule as outlined above.

In certain non-limiting embodiments, the polymer comprises at least one subunit (e.g., in the case of a PEG polymer, one subunit is ethylene oxide). In certain embodiments, the first targeting probes have the same number of polymer subunits. In certain embodiments, the first targeting probes have different numbers of polymer subunits. In certain non-limiting embodiments, the polymer can comprise between about 1 to about 30 subunits. In certain non-limiting embodiments, the polymer can comprise between about 1 to about 20, between about 2 to about 19, between about 3 to about 18, between about 4 to about 17, between about 5 to about 16, between about 6 to about 15, between about 7 to about 14, between about 8 to about 13, between about 9 to about 12, or between about 10 to about 11 subunits. In certain non-limiting embodiments, the polymer can comprise between about 1 to about 6, about 2 to about 5, or about 3 to about 4 subunits. In certain non-limiting embodiments, the polymer can comprise about 1, about 2, about 3, about 4, about 5, about 6, about 7, about 8, about 9, about 10, about 11 about, 12, about 13, about 14, about 15, about 16, about 17, about 18, about 19, or about 20 subunits. In certain non-limiting embodiments, the polymer can comprise about 4 subunits. In certain non-limiting examples, 2, 4, 6, 8, 10, 12, 14, or 16 polymer subunits can be used. In certain non-limiting embodiments, the PEG spacer can have a molecular weight of about 200 Da to about 20 kDa.

In certain non-limiting embodiments, the tertiary targeting moiety can be a protein, peptide, small molecule, or polynucleotide that binds to the biomarker. In certain non-limiting embodiments, the tertiary targeting moiety is an antibody as defined above. In certain non-limiting embodiments, the tertiary targeting moiety is a peptide.

In certain non-limiting embodiments, the detectable label is an imaging label, and/or therapeutic probe. In certain non-limiting embodiments, the imaging label can be, but not limited to, $^{110}$In, $^{111}$In, $^{177}$Lu, $^{52}$Fe, $^{62}$Cu, $^{64}$Cu, $^{32}$P, $^{11}$C, $^{13}$N, $^{15}$O, $^{67}$Cu, $^{67}$Ga, $^{68}$Ga, $^{86}$Y, $^{90}$Y, $^{18}$F, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{186}$Re, $^{188}$Re, $^{51}$Mn, $^{52m}$Mn, $^{55}$Co, $^{72}$As, $^{75}$Br, $^{76}$Br, $^{82}$mRb, $^{83}$Sr, and other gamma-, beta- or positron-emitters. In certain non-limiting embodiments, the therapeutic probe is therapeutic radioisotope, such as but not limited to $^{67}$Cu, $^{177}$Lu, $^{90}$Y, $^{131}$I, $^{212}$Bi, $^{211}$At, or $^{225}$Ac. In certain non-limiting embodiments, the therapeutic probe is an anticancer drug, such as, doxorubicin, paclitaxel, fluorouracil, etc. In certain embodiments, the active agent can be the tertiary targeting moiety.

In certain non-limiting embodiments, the active agent can be, but not limited to, a protein, peptide, small molecule, peptide nucleic acid (PNA), pharmaceutical, or radiopharmaceutical. Non-limiting examples of pharmaceuticals (which can optionally incorporate a radioisotope) include anticancer agents, antiinfective agents, antiproliferative agents, agents that modulate the immune response including agents that augment or that reduce the immune response, antithrombotic agents, etc.

In certain non-limiting embodiments, the active agent can be, but not limited to, trastuzumab, T-DM1, lapatinib, pertuzumab, cetuximab, panitumumab gefitinib, afatinib, dacomitinib, KD-019 erlotinib, cisplatin, carboplatin, gemcitabine, pemetrexed, irinotecan, 5-fluoruracil, paclitaxel, docetaxel, or capecitabine.

In certain non-limiting embodiments, the radiopharmaceutical can be $^{111}$In-ibritumomab tiuxetan, $^{90}$Y-ibritumomab tiuxetan, $^{131}$I-tositumomab, $^{131}$I-labetuzumab, $^{131}$I-rituximab $^{212}$Pb-trastuzumab, $^{131}$I-trastuzumab, $^{111}$In-trastuzumab, $^{188}$Re-trastuzumab.

5.4.3. Spacers and Methods of Optimizing the Length Thereof

As noted above, the first targeting probe and/or the second targeting probe can be attached to another moiety, e.g., a complexing target, detectable label, and/or the other of the first targeting probe and the second targeting probe, via a spacer.

In certain non-limiting embodiments, the invention provides an in vitro high-throughput screening platform for optimizing the length of spacers between the targeting molecules of the imaging and/or targeted drug delivery compounds. In certain non-limiting embodiments, the in vitro high-throughput screening platform is a sensitive assay that only utilizes targeting molecules in the nM range for each test. Using fewer targeting molecules can reduce the cost of the screening assay. In certain non-limiting embodiments, the invention provides reactions involving only one to two steps. FIG. 11 is a non-limiting example of an in vitro high-throughput screening assay of the invention.

In certain non-limiting embodiments, the method combines click chemistry and radio chemistry to optimize the spacer length. In certain non-limiting embodiments, cells can be used as a screening platform via on-site formation of targeted molecular imaging and/or targeted drug delivery compounds. In certain non-limiting embodiments, the targeting molecules of the targeted molecular imaging and/or targeted drug delivery compounds can be functionalized separately with a nonactivated photolabile functional group (i.e., photo-triggerable functional group) or a reactive functional group that binds to the photoliable functional group once activated by a photon generating source.

In certain non-limiting embodiments, the high-throughput screening platform comprises exposing cells to a first functionalized targeting molecule and a second functionalized targeting molecule, wherein either the first functionalized targeting molecule and/or second functionalized targeting molecule comprises spacers of different lengths between the targeting molecule and the reactive functional group. In certain non-limiting embodiments, either the first functionalized targeting molecule or second functionalized targeting molecule comprises spacers of a set length between the targeting molecule and the reactive functional group.

In certain non-limiting embodiments, the cells are exposed to photon energy to activate a nonactivated photolabile functional group, which allows the two targeting molecules to be linked via their respective spacers. In certain non-limiting embodiments, the assay can be quenched with excess radio-metal labeled chelators that are able to bind to the unbound activated photolabile functional group. In certain non-limiting embodiments, the amount of bound radio-metal labeled chelators can be measured. In certain non-limiting embodiments, the decrease in measured radioactivity indicates that the spacer length is appropriate or optimized.

In certain non-limiting embodiments, the first functionalized targeting molecule comprises a photolabile functional group. In certain non-limiting embodiments, the photolabile functional group can be, but is not limited to, Photo-OIDBO or Photo-tertrazole.

In certain non-limiting embodiments, and the second functionalized targeting molecule comprises a reactive functional group that only binds to the photolabile functional group once the photolabile functional group has been exposed to photon energy. In certain non-limiting embodiments, the reactive functional group of the second functionalized targeting molecule can be, but is not limited to, an azide or an alkene.

5.4.3.1. Preparation of Multivalent Compounds

In certain non-limiting embodiments, the first functionalized targeting molecule is a Nonactivated Photolabile Functional Group-(Monomer)n-Targeting Molecule (exemplified as p-ODIBO in FIG. 3) that comprises spacers (e.g., PEG) of various monomer lengths. In certain non-limiting embodiments, the spacer can comprise about 2 to about 30 monomers (as discussed above). For example, but not by way of limitation, n can equal 2, 4, 6, 8, 10, 12, 14, 16, 18, 20, or 30 monomers. In certain non-limiting embodiments, the Nonactivated Photolabile Functional Group-(Monomer)n-Targeting Molecules can be prepared by first forming $NH_2$-(Monomer)n-Targeting Molecules by adding Boc-(Monomer)n-NHS to the targeting molecule of interest followed by Boc deprotection. For example, the Boc-(Monomer)n-NHS can be combined with the targeting molecule in a suitable buffer (e.g., phosphate buffered saline (PBS)) followed by deprotection with trifluoroacetic acid (TFA) (e.g., 95%). The prepared NH2-(Monomer)n-Targeting Molecule can then be mixed with Nonactivated Photolabile Functional Group-NHS to produce Nonactivated Photolabile Functional Group-(Monomer)n-Targeting Molecules.

In certain non-limiting embodiments, the second functionalized targeting molecule is a Reactive Functional Group-Spacer-Targeting Molecule (exemplified as $N_3$ in FIG. 3), which comprises a spacer with a set monomer length. In certain non-limiting embodiments, the spacer can comprise about 2 to about 30 monomers (as discussed above). For example, but not by way of limitation, the spacer can be 4 or 8 monomers. In certain non-limiting embodiments, the reactive functionalized targeting molecule can be prepared by mixing the targeting molecule and Reactive Functional Group-Spacer-NHS in a suitable buffer (e.g., PBS).

In certain non-limiting embodiments, the reactive functionalized targeting molecule comprises spacers of different lengths rather than the photolabile functionalized targeting molecule. As one non-limiting example, it can be more convenient to test the spacer length using a reactive functionalized targeting molecule instead of a photolabile functionalized targeting molecule, as the former can be easier to prepare.

By way of example, and not limitation, the photolabile functionalized targeting molecule can be a photo-ODIBO-PEGn-RGD peptide (e.g., n=2, 4, 6, 8, 10, 12, 14, 16, 18, 20). Also by way of example, and not limitation, the reactive functionalized targeting molecule can be N3-PEGn-cetuximab.

5.4.3.2. In Vitro High-Throughput Assay

In certain non-limiting embodiments, Reactive Functional Group-Spacer-Targeting Molecules can be mixed with one set of Nonactivated Photolabile Functional Group-(Monomer)n-Targeting Molecules with a spacer having a particular monomer length. For example, in such embodiments, there can be one mixture of each spacer length combination. In certain non-limiting embodiments, Nonactivated Photolabile Functional Group-Spacer-Targeting Molecules can be mixed with one set of Reactive Functional Group-(Monomer)n-Targeting Molecules with a spacer having a particular monomer length. In certain non-limiting embodiments, the reactive functionalized targeting molecules and nonactivated photolabile functionalized targeting molecules can be mixed in about a 1:1 molar ratio to prepare mixed-targeting molecule stock solutions. This ratio can be adjusted depending on the densities of the two targeted receptors. In certain non-limiting embodiments, each reaction mixture comprises functionalized targeting molecules each with one specific spacer length.

In certain non-limiting embodiments, one of the mixed-targeting molecule stock solutions can be added to cells comprising the biomarkers of interest. It is desirable to have a large excess of targeting molecules present. In certain non-limiting embodiments, after the targeting molecules bind to the targeted biomarker, the unbound targeting molecules will be washed off (e.g., using a suitable buffer).

In certain non-limiting embodiments, the cells are exposed to photon energy (including but not limited to laser and/or other light sources) for between, for example, about 1 min and 1 hour (inclusive), i.e., for a period of time effective to convert the nonactivated photolabile functional group on the functionalized targeting molecule to the activated photolabile functional group.

In certain non-limiting embodiments, radiolabeled reactive functional groups that bind to the activated photolabile functional group are added to the cells. In certain non-limiting embodiments, the cells are incubated 2-4 hours before adding the radiolabeled reactive functional group. In certain embodiments, the radiolabeled functional group can be a N3-Radioactive Element-Chelator (e.g., N3-($^{64}$Cu) NOTA), and can, in non-limiting embodiments, be added 2-4 hours after the photo irradiation to allow sufficient time for the click reaction between two different targeting molecules. The purpose of adding this N3-Radioactive Element-Chelator is to detect the amount of non-reacted photolabile functional group for measuring the extent of the click reaction between the two different targeting molecules. In certain non-limiting embodiments, the radiolabeled reactive functional groups bind to the "excess" activated photolabile group that is bound to the biomarker but did not bind to the reactive group of a functionalized targeting molecule.

In certain non-limiting embodiments, the cells are washed with an appropriate buffer to remove excess radiolabeled reactive groups before detecting the level of radioactivity by methods known to those of skill in the art. In certain non-limiting embodiments, the combination of functionalized targeting molecules with the lowest radio-counts, containing the lowest "excess" radiolabeled reactive groups, indicates that the corresponding spacers are of an appropriate or optimal length.

By way of example, and not limitation, the Reactive Functional Group-Spacer-Targeting Molecule (e.g., N3-PEG4-cetuximab) can be mixed with one or more (e.g., about ten) Nonactivated Photolabile Functional Group-(Monomer)n-Targeting Molecules (e.g., photo-ODIBO-PEGn-RGD peptides; n=2, 4, 6, 8, 10, 12, 14, 16, 18, 20) in a 1:1 molar ratio to prepare one or more (e.g., about ten) mixed-targeting molecules stock solutions. Each of the mixed-targeting molecules stock solutions can be added to separate cell culture wells pre-seeded with cells and the cells can be incubated with the mixed-targeting molecules (e.g., until binding equilibrium is achieved). In certain embodiments, the cells are pre-seeded in 24, 48, 96, 384, or 1536 well plates. Following incubation with the mixed targeting molecules, the cells can be washed with a suitable buffer (e.g., PBS) to remove unbound targeting molecules. The cells can then be exposed to photon energy (e.g., a UV lamp (365 nm)) to activate the photolabile functional group (e.g., to generate azide-active "ODIBO"), subsequently triggering ligation between the reactive group and the activated photolabile group (e.g., N3-PEGn-AE105 and ODIBO-PEGn-RGD) bound to the biomarkers on the cells. Following incubation to allow the two targeting molecules to bind (e.g., 2-4 hours), radiolabelled reactive groups (e.g., N3-($^{64}$Cu) NOTA) can be added to the cells, which will bind to the activated photolabile groups not bound to the reactive groups of the functionalized targeting molecules. The unbound radiolabelled reactive group can be washed away, and the plate of cells can be processed to be read with a plate reader (e.g., a high-throughput MicroBeta2 Plate Counter) to measure the radiolabelled reactive groups.

5.4.3.3. Cell Lines

In certain embodiments, this method can be applied using various cell cultures, including but not limited to, primary cell cultures, tissue explants, or transformed cell cultures known in the art. Non-limiting examples of such cell cultures include: Primary-hBM SC; Primary-hSkin FB; Primary-cow CC; Primary-rat BMSC; Primary-h CC; MC3T3-E1; Primary-hUVEC; Primary-rabbit CC; NIH 3T3; Primary-CC; Primary-rat Liver Hep; Primary-hSkin Keratinocyte; MG63; HEP-G2; L929; Primary-BM SC; Primary-rabbit BM SC; Primary-pig CC; Primary-hBone OB; MCF-7; Primary-rat Heart CM; Primary-h Foreskin FB; PrimaryhAdipose SC; Primary-hFB; Primary-hAdipose SC; Primary-FB; Primary-ratAortaSMC; Primary-Bone; Primary-dog CC; 3T3 (nonspecific); C2C12; MDA-MB-231; SaOS-2; Primary-mouse BM SC; Primary-rat CC; Primary-h Mesoderm Mes Pre C; Primary-rat Brain Neuronal; PC12; Primary-Cancerous; Primary-h Skin EC; Primary-rat BM OB; Primary-mouse Embryo SC; MCF-10A; Primary-h Bone OB-like; Primary-goat BMSC; Primary-h Aorta SMC; MDCK (Madin-Darby Canine Kidney); Primary-hi DAnnulus C; Primary-ratBone OB; Primary-h Adipose Preadipocyte; Primary-SC; Primary-rat Skeletal Muscle Myoblast; Primary-Heart CM; Primary-cow AortaEC; Primary-dog BM SC; Primary-sheep BM SC; Primary-sheep CC; Primary-pig BMSC; Primary-cow BMSC; Primary-h BladderSMC; Primary-pig Aorta EC; Primary-h Cornea Epi C; Primary-h Aorta EC; Primary-h Cornea FB; Primary-pig Aorta SMC; Primary-mouse Liver Hep; A549; Primary-Bone OB; Primary-h Bladder Uro; Primary-h UV SMC; Swiss 3T3; Primary-Liver Hep; Primary-h Lig FB; Primary-h Coronary Artery SMC; Primary-OB-like; Primary-h Teeth Mes Pre C; HT1080; Primary-rat Heart FB; Primary-pig HV Intersticial C; C3A; Primary-h Breast Cancerous; Primary-h Foreskin Keratinocyte; Primary-h Oral Mucosa Keratinocyte; Primary-mouse Ovary Oocytes; Primary-h Vase SMC; 3T3-L1; Primary-h Lung FB; Primary-chicken Ganglia Neuronal; Primary-h U CStC; Primary-cow Aorta SMC; Primary-mouse Embryo FB; Primary-h Bronchi EpiC; CHO-Kl; Primary-h Liver Hep; Primary-hSaphVEC; Primary-hTeethPDL; Primary-rat Skin FB; Primary-pig Liver Hep; PC-3; Primary-SMC; Primary-hMVEC; Primary-mouseFB; Primary-h Nasal Chondrocyte; Primary-hCorneaKeratinocyte; Primary-hOvaryCancerous; Primary-h U CBSC; Primary-rat Heart EC; Primary-Vasc; Primary-mouse Skin FB; Primary-h Tendon TC; Primary-rat Brain Astrocyte; Primary-rat Nerve SC; Ha CaT; Primary-h Gingiva FB; Primary-Neural; Primary-cow Bone OB; Primary-rat Adipose SC; Primary-mouse Bone OB; Primary-h Teeth PC; Primary-h Blood Mononuclear; Primary-rat Hippocampus Neuronal; D3; HeLa; HEK293; C17.2; Primary-h Skin Melanocyte; Primary-h Blood EC-like; HOSTE85; Primary-h UC SC-like; Primary-h Cornea SC; Primary-rat Aorta EC; Primary-h Saph VSMC; Primary-h UCBEC; Primary-mouse Heart CM; D10RL UVA; Primary-h Coronary Artery EC; Primary-h Aorta Myo FB; HT-29; Primary-h Tendon FB; RAW 264; Primary-rat Dental Pulp SC; 3T3-J2; H1; Primary-pig Teeth; Primary-rat Sciatic Schwann; Primary-rabbit Bone OB-like; Primary-sheep Aorta EC; Primary-rabbit Cornea Epi C; Primary-h Ovary Epi C; Primary-rabbit Ear Chondrocyte; SH-SY5Y; Primary-h Teeth FB; Primary-h Oral Mucosa FB; Primary-rabbit FB; C6; Primary-rat Testes Stertoli; Primary-cow Arterial EC; Primary-pigHVEC; Primary-cow Nucleus Pulposus Cells; Primary-rat Ganglia Neuronal; Primary-dog Bladder SMC; Primary-Vasc SMC; 129/SV; Primary-pig Ear Chondrocyte; ED27; Primary-rabbit Bone B; Primary-h Brain Glioblast; Primary-rat Adipose Preadipocyte; Primary-h Cartilage Synov; Primary-rat Pancreas Insulin; Primary-hEC; Primary-sheep Aorta SMC; Primary-h Endometrium EpiC; U251; Primary-h Endometrium StC; Primary-pig Bladder SMC; Primary-h HVIintersticial C; Primary-pig Esoph SMC; Primary-h NP Neuronal; Primary-rabbit Aorta SMC; Primary-h NSC; Primary-rabbit CorneaFB; Primary-h oral Cancerous; Primary-rabbit Lig FB; Primary-h SC; Primary-rat BMOB-like; Primary-h Skeletal Muscle Myoblast; COS-7; C-28/12; HK-2; Primary-h Uterus Cancerous; Primary-rat Ventricle CM; Primary-h Vase EC; Primary-sheep Carotid Artery SMC; HCT-116; ROS 17/2.8; Primary-h Vocal FB; UMR-106; Primary-mouse Aorta SMC; H9; R1; Primary-rat Fetal Neuronal; Primary-chicken Ear EpiC; Huh7; Primary-rat Vasc SMC; Primary-h NP SC; ES-D3; IMR-90; Primary-rat Bladder SMC; 293T; Primary-h Foreskin VascularEC; Primary-h Placenta EC; Primary-h Lung EpiC; Primary-h Prostate EpiC; U-87 MG; Primary-dog Carotid Artery SMC; Primary-rabbit Cornea StC; Primary-dog ID Annulus Fibrosus; Primary-chicken Embryo Chondrocyte; Primary-EC; HFF; Vero; HFL-1; Primary-h Adipose FB; Primary-cow FB; Primary-h UTSMC; Primary-rat Ventricle FB; AH 927; Primary-sheep Vasc FB; DU-145; ST2; B16.F10; Primary-h Nasal EpiC; Primary-ID Annulus C; Primary-h Dental Pulp SC; 3H10T1/2; Primary-Heart Valve; Primary-h Bone Alveolar; Primary-rabbit Tendon FB; Primary-mouse Kidney Insulin; HEPM; Primary-baboon Aorta SMC; HTK; Primary-mouse MDSC; Primary-rat Esoph EpiC; Primary-mouse Nerve SC; Primary-h Fetus OB-like; Primary-mouse Skeletal Muscle SC; hFOB 1.19; Primary-Nerve Schwann; Primary-h Ganglia Neuronal; Caco-2; Primary-h Kidney Renal; Primary-h Breast EpiC; Primary-h Liver SC; Primary-pig Bladder Uro; Primary-h Lung EC; Primary-h Breast FB; Primary-sheep Jugular Vein EC; Primary-pig Esoph EpiC; Primary-h Lymph EC; Primary-chicken CC; Primary-h Lymph TCell; Primary-h Colon Adenocarcinoma; Primary-h Mammary EC; Primary-pig Vocal FB; Primary-h Mammary EpiC; Primary-rabbit Adipose SC; Primary-h Cornea EC; H9c2; Primary-h UT StC; Primary-cat Heart CM; Primary-mouse Pancreas EpiC; HS-5; Primary-sheep Skeletal Muscle Fetus Myoblast; Primary-cow ID; Primary-mouse BM OCpre; Primary-cow Knee Meniscus C; Hep-3B; Primary-cow Lig FB; HL-1; HuS-E/2; RWPE1; Primary-cow Retina EpiC; Primary-hVascMyoFB; IEC-6; Primary-mouse Fetal Hep; HS68; OVCAR-3; Primary-dog Knee MeniscusC; Primary-rabbit Mesoderm Mes PreC; Primary-dog Lig FB; Primary-rat Lung Alveolar; Primary-dog Skin Keratinocyte; CRL-11372; Primary-dog Vase SMC; HMEC-1; Primary-Embryo SC; T-47D1; Pimary-goatCC; Primary-h UVSC-like; Primary-guineapig Ear EpiC; Primary-Ligament; Primary-guineapig Skin FB; Primary-mouse Cortical Neuronal; Primary-hAdipose Adipocyte; Primary-mouse Liver SC; Primary-h Adipose FB-like; CAL72; J774; P19; Primary-h Amniotic fluid; Primary-rabbit Cornea EC; Primary-h Amniotic FSC; Primary-rat BMFB-like; ARPE-19; Primary-rat Kidney Mesangial; K-562; Primary-rat Nasal Ensheathing; Primary-h Bladder StC; Primary-chicken Embryo Proepicardium; ATDC5; Primary-sheep FB; Kasumi-1; Primary-Skeletal Muscle; Primary-h Bone Mes PreC; HMT-3522; Primary-h Bone Periosteal; A431; Primary-h Brain EC; Primary-h UTFB; KLE; 143b OST; BALB/3T3; Primary-h Vasc FB; LLC-PKI; Primary-h Vasc Pericyte; BHK21-C13; Primary-Mammary EpiC; M.DUNNI; C4-2B; ZR-75; HEC-1B; Primary-h Gingiva Keratinocyte; U178; Primary-h HN Cancerous; Primary-mouse Mammary EpiC; Primary-h Keratinocyte; Primary-mouse Sciatic N Schwann; OVCA429; Primary-h Kidney EpiC; Primary-pig Esoph FB; MBA-15; Primary-pig Mandible FB-like; Primary-h Liver Cancerous; Primary-rabbit Bladder Uro; GD25betalA; Primary-rabbit ID AnnulusC; HSC-T6; Primary-rabbit NP Neuronal; DOV13; HEY; Primary-h Mammary FB; HTB-94; BZR-T33; Primary-chicken CorneaFB; MiaPaCa2; Primary-rat Mucosa Ensheathing; Primary-hOvaryFB; Primary-rat Salivary Acinar; Primary-h Ovary Oocyte; Primary-rat Testes Germ; Primary-h Pancreas Cancerous; Primary-chicken Embryo StC; Primary-h Pancreas Stellate Cells; Primary-sheep Carotid Artery FB; MLO-Y4; Primary-chicken Retina SC-like; Primary-h Prostate Cancerous; Primary-chicken Ten TC; Primary-h Saph V Myo FB; Primary-Synoviocyte; MTLn3; Primary-Vasc EC; Primary-h Skeletal Muscle Pre; RT4-D6P2T; C2; SCA-9; HOC-7; T31; Primary-h UC EpiC; TR146; HCS-2/8; EA.hy926; Primary-rat Ebryo; SW480; Primary-sheep Fetus CC; Primary-dog Pancreas Insulin; KS-IMM; BPH-1; Primary-rat Pancreas SC; M2139; RIN-5F; Primary-hGallbladderCancerous; E14/TG2a; M4E; HES3; G8; Primary-hConjunctivaFB; Primary-dogSaphVEC; LN CaP; Primary-dog Saph V SMC; M4T; Primary-h Fetus CC; BR-5; Primary-pig UT Uro; Primary-Hippocampus Neuronal; PE-0041; Primary-dog Skin FB; Primary-rabbit Skeletal Muscle Myo-Blast; Primary-cow Denta ipulp; CGR8; Primary-dog Teeth PDL; Primary-rat Fetus Hep; Primary-dog Tendon FB; Primary-rat Mammary; Primary-h Knee C; Primary-rat SMC; BRC6; Primary-sheep Artery FB; Primary-dog Vasc EC; Primary-cow Mammary Alveolar; pZIP; 293 cell line; BMC9; Primary-h Lung Cancerous; SKOV-3; IOSE; TEC3; MCF-12A; Primary-rabbitBladderEpiC; Gli36DeltaEGFR; Primary-rabbit Conjunctiva EpiC; Primary-h Lung Neuronal; Primary-rabbit Endometrium EpiC; 1205Lu; Primary-rabbit MDSC; 3T3-A31; Primary-rabbit Tendon Tenocyte; MDA-MB-435; Primary-h Cancerous; Primary-cow EC; Primary-rat Cornea FB; Primary-EpiC; Primary-rat Fetal Cardiac; Primary-h Meninges Arachnoidal; COS-1; Primary-Eye; Primary-rat Liver Oval C; GLUTag-INS; Primary-rat Oral Mucosa Keratinocyte; GM3348; CRFK; 21NT; Primary-rat Testes EC; Primary-h Nasal FB; Primary-h Dura MaterSC; Primary-h Nasal OB; Primary-dog NP Neuronal; Primary-h Nasal Secretory; Primary-sheep Lung FB; AC-1M59; BHPrE1; MIN6; Primary-UT; MKN28; RAT-2; MLO-A5; RT112; CRL-2266; S91; GM5387; SK-ChA-1; Primary-horse CC; SPL201; Primary-horse Tendon FB; Primary-h Fetus Mes PreC; D283; Primary-pig Thyroid EpiC; H1299; Par-C10; AE-6; Primary-rabbit Blood Platelet; Primary-goat Carotid EC; Primary-rabbit Bone OC; Primary-goat Carotid FB; Primary-cow Cornea FB-like; Primary-h Pancreas SC; Primary-rabbit CT Pericyte; Primary-goat Carotid SMC; Primary-rabbit Esophagus SMC; Primary-h Parotid Acinar; Primary-baboon Blood EC; A498; Primary-h Bronchi SMC; Primary-h Placenta SC; Primary-rabbit Sphincter SMC; Primary-cow Retina SC; 7F2; MM-Sv/HP; A10; Primary-h Prostate StC; Primary-buffalo Embryo SC-like; Primary-h Salivary Cancerous; CHO-4; Primary-h Salivary Salisphere; Primary-rat Cortical Neuronal; H13; Primary-rat Embryo Neuronal; Primary-guineapig Pancreas EpiC; Primary-rat Fetal OB; H144; CNE-2; MPC-11; 21PT; Primary-cow Synovium; Primary-rat Liver EC; Primary-cow Fetus CC; 20 BEAS-2B; H2122; LM2-4; Detroit 551; C18-4; FLC4; Ishikawa; Primary-rat Skin Keratinocyte; H35; Primary-rat Tendon; Primary-h SMC; HTR8; Primary-h Synovial CC; E8.5; H460M; HL-60; MUM-2B; CRL-1213; MUM-2C; CRL-12424; W20-17; Lovo; Primary-dog Blood EC; Primary-sheep Nasal CC; HAK-2; Primary-sheep Skin FB; Primary-h Testes Sertoli; Primary-h Thyroid Cancerous; Primary-Trachea; Primary-h Trachea; LRM55; Primary-h UASC-like; Primary-Colon FB; Primary-hUASMC; r-CHO; HAT-7; RN22; HC-11; Primary-h Eye Vitreous; AEC2; S2-020; HCC1937; CRL-2020; AG1522; SCC-71; N18-RE-105; SK-N-AS; Primary-h Uterus SMC; SLMT-1; IMR-32; STO; NB4; Swan 71; Primary-h Alveolar Perosteum; Primary-dog Oral Mucosa EpiC; Primary-h Amnion EP; Primary-h Fetus Schwann; Primary-dog Bone OB; Primary-pig UTSMC; 184A1; Panc 1; NCTC 2544; 46C; Primary-cow Cornea EC; B6-RPE07; Primary-hamster EC; cBAL111; Primary-hamster Retina Neuronal; HEPA-1Clc7; NEB1; CCE; NHPrE1; Primary-rabbit Conjunctiva FB; 410; Hepa RG; Primary-Keratinocyte; PMC42-LA; Primary-dog Cartilage Synov; 21MT; NOR-P1; Primary-rabbit Endometrium StC; Primary-Lymphnode Lymphocyte; DLD-1; Primary-Lymphnode TCell; Primary-rabbit Lacrimal Gland Acinar; AB2.1; primary-rabbit Lung Pneumocyte; Primary-monkey Embryo; ES-2; Primary-monkey Kidney FB-like; Primary-rabbit Penis SMC; Primary-mouse Adipose StC; Primary-rabbit Skin FB; NR6; Primary-Blood SC; Primary-mouse BM Macrophage; 786-0; AT2; Primary-rat Adrenal Chromaffin; AT3; CCF-STTG1; Primary-mouse Bone Calvarial; Primary-rat Bladder Uro; HCT-8/E11; CE3; Primary-mouse Brain Neuronal; CFK2; Primary-mouse Breast Cancerous; L6; Primary-mouse Chondrocytes; HeyA8; Primary-mouse Colon EpiC; Primary-rat Cortical Astrocyte; Primary-dog CFB; Primary-buffalo Ovary EpiC; Primary-dog Cornea Chondrocyte; Primary-rat Embryo CM; Primary-mouse Embryo Neuronal; A2780; C5.18; Primary-dog MV EpiC; Primary-mouse Esophagus SC; Primary-rat Fetal Renal; HEK001; A357; EFO-27; Primary-chicken Bone OB; Primary-mouse Fetal Lung; Primary-rat Heart SC-like; Primary-mouse Germ; Primary-rat Kidney; EN Stem-A™; Primary-rat Lacrimal Acinar; U-251 MG; Primary-dog Myofibroblasts; A4-4; Primary-rat Liver SC-like; Primary-cow Brain EC; Primary-rat Lung FB; Primary-mouse Kidney Renal; BEL-7402; NT2; HIAE-101; Primary-h BM Mononuclear; Primary-rat Ovary; Primary-mouse Lymph FB-like; Primary-rat Pancreas Islets; Primary-dog Esophageal EpiC; Primary-rat Renal EpiC; Primary-mouse Mast; Primary-chicken Embryo Blastoderm; NTera2/cl.D1; G-415; Null; Primary-rat Small Intestine; Primary-mouse Ovary Cumulus C; Primary-rat Teeth SC-like; HEL-299; Primary-rat Tendon Tenocyte; KB; b-End-2; Primary-mouse Pancreas Insulin; Primary-rat Vase EC; Primary-mouse Salivary Salisphere; Primary-h Duodenum EpiC; Primary-h Bone Fetus OB; Primary-Respiratory EpiC; Primary-mouse Skeletal Muscle Myoblast; Primary-sheep Amniotic fluid; OC2; Primary-chicken Heart CM; Daudi; Primary-shee pArtery MyoFB; Primary-mouse SkinKeratinocyte; Primary-sheep Bone OB-like; Primary-mouse Small Intestine; Primary-chicken Heart ECM; Primary-mouse Spleen Tcell; LNZ308; Primary-mouse Teeth Odontoblast; Primary-sheep ID Annulus Fibrosus; Primary-mouse Testes SC; Primary-sheep Jugular Vein SMC; Primary-mouse Testes Sperm; Primary-sheep Lung SC; Primary-mouse UT Uro; Primary-sheep Saph VEC; Primary-mouse Uterus EpiC; Primary-sheep Skin EC; OCT-1; Primary-sheep Vasc EC; HELF; Primary-sheep Vasc SMC; CAC2; HL-7720; OPC1; Primary-Teeth PDL; Primary-dog Heart SC; Primary-UCB Mononuclear; Primary-pig Artery Carotid EC; Primary-h Endometriotic CystStC; Primary-pig Artery Carotid SMC; Primary-Colon Cancerous; Primary-pig Artery Coronary SMC; QCE-6; Primary-pig Bladder FB; R221A; OSCORT; LS180; B35; RIF-1; Calu-1; RL-65; Calu-3; Primary-cow Adrenal ChrC; B5/EGFP; RT-112; Primary-pigEC; RW.4; Primary-pig ESC; S2-013; OVCAR-5; S5Y5; Primary-h Bone OC-like; SA87; INT-407; SAV-I; Primary-pig Fetus Hep; SCC-68; P69; HNPSV-1; CaSki; SK-CO15; Primary-pig Iliac EC; SK-N-DZ; Hep2; SKOV31p.1; Primary-pig Mandible Ameloblast; SNB 19; Primary-cow Joint Synovial; Primary-h Fetus FB; Primary-pig Mandible Odontoblast; SW1353; Primary-pig NP Neuronal; SW948; Primary-pig Oral MucosaEpiC; CRL-2102; Primary-cow PancreasIslets; T4-2; Primary-pig PulmonarySMC; TE-85; Primary-pig Salivary Acinar; THP-1; Primary-pig SynoviumSC; BME-UV1; KG-1; D4T; HUES-9; Primary-mouse Hippocampus Neuronal; ECV304; NRK; Primary-mouse Kidney Mesangial; D407; 10T1/2 cell line; and Primary-h Foreskin Melanocyte.

5.4.4. Examples of Targeting Probes

Table 1 below provides non-limiting examples of targeting ligands (i.e., the first targeting probe and/or the tertiary targeting moiety) that bind specific biomarkers.

TABLE 1

Examples of targeting ligands

| Biomarkers | Targeting ligand monoclonal antibody | peptide (or small molecule) ligand |
|---|---|---|
| Integrin α4β1 | N/A | LLP2A (peptide) |
| uPAR | N/A | AE105 (peptide) |
| gastrin-releasing peptide (GRP) | N/A | BBN(7-14) (peptide) |
| SSTR2 | N/A | Tyr(3)-octreotate (peptide) |
| Folate receptor | N/A | Folic acid (small molecule) |
| CCR5 | N/A | DAPTA (peptide) |
| CXCR4 | UMB2 (ab124824) | AMD 3465 (small molecule), T140, CPCR4-2 (peptides) |
| Integrin αvβ3 | Etaracizumab | RGD (peptide) |
| Plectin-1 | E398P (ab32528) | PTP (peptide) |
| EGFR | Cetuximab | Erlotinib (small molecule) |
| VEGF | Bevacizumab | N/A |
| MUC4 | mAb 8G7 | N/A |
| CA19-9 | 1116NS19-9 | N/A |
| CD40 | CP-870,893 | N/A |
| PD-l1 | Atezolizumab | N/A |

In addition to the targeting ligands discussed above, the methods of the present invention can also be applied to other pre-targeting strategies such as, but not limited to metal-free click reactions, bispecific antibodies and radiolabeled haptens, biotin-(strept)avidin, etc.

In certain non-limiting embodiments, the methods comprise administering at least one first targeting probe, wherein the at least one first targeting probe includes a primary targeting moiety and a complexing target. In certain non-limiting embodiments, the primary targeting moiety can be an antibody. In certain non-limiting embodiments, the complexing target can be a bioorthogonal ligand. In certain non-limiting embodiments, the bioorthogonal ligand can be trans-cyclooctene. In certain non-limiting embodiments, the method comprises administering at least one second targeting probe, wherein the at least one second targeting probe includes a secondary targeting moiety, a tertiary targeting moiety, and a detectable label. In certain non-limiting embodiments, the secondary targeting moiety can be a bioorthogonal ligand. In certain non-limiting embodiments, the bioorthogonal ligand can be tetrazine. In certain non-limiting embodiments, the tertiary targeting moiety can be a peptide. In certain non-limiting embodiments, the detectable label can be an imaging label. In certain non-limiting embodiments, the primary targeting moiety binds EGFR. In certain non-limiting embodiments, the tertiary targeting moiety binds αvβ3. In certain non-limiting embodiments, the imaging label can be detectable label can be $^{64}$Cu.

5.5. Kits

The present invention further provides kits that can be used to practice the invention. For example, and not by way of limitation, a kit of the present invention can comprise at least one first targeting probe and/or at least one second targeting probe. In certain embodiments, a kit of the present invention can optionally comprise instructions on how to use the kit for molecular imaging and/or targeted drug delivery. In certain non-limiting embodiments, a kit can further comprise an administration device such as a syringe and/or catheter and/or introducer sheath.

In certain non-limiting embodiments, the at least one first targeting probe comprises a primary targeting moiety and a complexing target. In certain non-limiting embodiments, the at least one second targeting probe can be selected from either an imaging probe or a therapeutic probe. In certain non-limiting embodiments, the imaging probe comprises a secondary targeting moiety, tertiary targeting moiety, and a detectable label. In certain non-limiting embodiments, the therapeutic probe comprises a secondary targeting moiety, tertiary targeting moiety, and an active agent. In certain non-limiting embodiments, the therapeutic probe can further comprise a detectable label.

The present invention further provides kits for preparing the first targeting probe and/or second targeting probe. In certain embodiments, the kit of the present invention contains the first targeting probe (in dry or liquid form) and/or the second targeting probe (in dry or liquid form) for application on the biomaterial. When the probe is provided in dry form, the kit can contain the appropriate buffer or solvent to create a solution or composition.

The following Example is offered to more fully illustrate the disclosure, but is not to be construed as limiting the scope thereof. Methods and materials described in the examples are hereby incorporated by reference into the detailed description of the invention.

6. EXAMPLES

Example 1: PET Imaging Using Dual-Receptor Pre-Targeting Imaging

1. Introduction

The present example describes the development of a dual-receptor pre-targeting molecular imaging method in which a radioactive molecule binds to both the pre-administered tumor specific antibody and the tumor cell. While the introduction of this example focuses on PDAC, it is equally applicable to other types of tumors and cancer.

PDAC is the fourth leading cause of cancer death in the United States. In 2014, an estimated 46,400 people were diagnosed with PDAC, and 39,600 of these subsequently perished from this disease (29). The deep anatomical location of the pancreas and the relatively nonspecific symptomatic nature of PDAC frequently results in its late-stage diagnosis, which results in a median survival rate of 6 months and an overall 5-year survival rate of less than 5% (30, 31). Retrospective studies demonstrate that tumor size is inversely correlated with improved survival, and PDAC patients with <1 cm tumors have a realistic chance of a cure and nearly 100% 5-year survival rates (32-35).

The current low rate of detection is due to the fact that the majority of imaging methods for pancreatic cancer rely largely on morphological changes. Unlike anatomical imaging modalities, PET delivers biochemical/metabolic information about tumor biology along with very high sensitivity, making it a very attractive method for pancreas cancer early detection (36). Currently available targeting PET tracers, however, fail to detect early pancreatic cancer due to lack of sufficient specificity or sensitivity. Therefore, there exists a need to develop a novel PET imaging technology to detect resectable PDAC tumors, ideally with a size of <1.0 cm.

This example utilized a dual-receptor pre-targeting (DRPT) molecular imaging method that comprises a fast-clearing tetrazine (Tz)-radioactive molecule (RM) attached to a targeting-ligand (TL) that binds to the tumor cells to enhance local concentration as well as prolong its retention on tumor resulting in increased ligation with the pre-injected slow-clearing trans-cyclooctene (TCO)-mAb.

As both αvβ3 and EGFR are overexpressed in many different types of tumors and usually associated with poor prognosis, the combination of αvβ3/EGFR used in the DRPT imaging strategy for cancer imaging.

Integrins are heterodimeric surface receptors, and they are cell adhesion molecules that mediate cell-cell and cell-matrix interactions and contribute to migration, proliferation, angiogenesis, tumor invasion, and metastasis (39). Importantly, integrins αvβ3 are usually expressed at very low (or undetectable) levels in most adult epithelia cells, but are highly upregulated in various tumor cells (40-42). Recent expression analysis demonstrated that αvβ3 was expressed in 60% of invasive PDAC at stages I-IV, and those patients with high αvβ3 expression showed significantly shorter survival times than those with low αvβ3-expression (mean survival times, 12. vs. 21.4 mo, respectively) (43). RGD peptide based radiotracers (44-49) have been developed for αvβ3 targeted cancer imaging.

Epidermal growth factor receptor (EGFR or HER1), and EGFR cell signaling has been shown to play an essential role in the upregulation of tumor cell proliferation, differentiation, metastasis, and evasion of apoptosis (50-53). Overexpression of EGFR is the hallmark of many human tumors, including colorectal, lung, breast and pancreatic cancers, and thus has proven to be a valid target for the treatment and imaging of cancers (54-58). In PDAC, EGFR overexpression is observed in >70% of patients, and signal transduction via EGFR is associated with a poor prognosis and a significant decrease in survival rate (55, 59). Among the various EGFR inhibitors, FDA-approved cetuximab (c225, a chimeric monoclonal antibody) is known to be an internalizing antibody. Cetuximab was been radiolabeled for PET imaging in this example.

2. Materials and Methods

Materials:

The potent biomarkers and corresponding available cell lines (both positive and negative) selected for this project are summarized in Table 2.

TABLE 2

Biomarkers, corresponding cells, and targeting probes

| | Probe | positive cells | negative cells |
|---|---|---|---|
| $\alpha_v\beta_3$ | Peptide: cyclco(RGDyK) (RGD) | U87MG | |
| EGFR | mAb: cetuximab | U87MG | 4T1 |

Cell lines and primary cells. All cancer cell lines in this Example was purchased from American Type Culture Collection (Manassas, VA), including human brain cancer cell line (U87MG) and mouse mammary cancer cell line 4T1. 4T1 served as negative control. All of the cell lines were cultured according to vendor recommended growth conditions.

Radiolabeling of peptides, small molecules and/or antibodies. Due to favorable decay properties (β+: 0.653 MeV, 17.4%; β−: 0.578 MeV; 39%; t½=12.7 hr), $^{64}$Cu was used. $^{64}$Cu labeling of the NOTA bifunctional chelator (NOTA BFC) attached bioconjugates (peptides, small molecules and antibodies) was conducted in a 0.2 M NH$_4$OAC buffer (pH=6.8). Briefly, $^{64}$CuCl$_2$ (usually in 0.1 N HCl) was first buffered in a 0.2 M NH$_4$OAC buffer (pH=6.8), and then the prepared NOTA-bioconjugates NODAGA-DAPTA were added. The resulting mixture was vortexed for 10 sec and incubated in a thermomixer at 37° C. for 0.5 h, after which the $^{64}$Cu incorporation yield was determined by radio-HPLC.

Animal Model:

Nude mice were injected with 4T1 cells (2 million cells in 150 μL PBS) into the subcutaneous flank of the left shoulder and U87MG (5 million cells in 150 μL PBS) into the subcutaneous flank of the right shoulder.

Dual-Receptor Pre-Targeting (DRPT) Molecular Imaging Method:

The procedures of the DRPT strategy are illustrated in FIG. 2: first, TCO-mAb was injected into bloodstream, and after its tumor accumulation and concomitant blood clearance, a targeting-ligand containing Tz-RM-TL was injected. TCO and Tz are a pair of bioorthogonal ligation groups that bind to each other (depicted as an "X" moiety in FIG. 2). The Tz-RM-TL was prepared as outlined in Example 2. The TCO-mAb was prepared as outlined in Example 3.

Statistical Analysis:

All the experiments were performed in triplicated. Comparisons between different groups of experiments were made using the two-way ANOVA test (GraphPad Prism 6). When more than two data sets were compared, a two-way ANOVA analysis with Bonferroni post-tests were applied. P values <0.05 were considered statistically significant.

3. Results and Discussion

Compared to traditional pre-targeting, the integration of an additional targeting ligand into Tz-RM significantly enhanced its sensitivity and specificity, which can be attributed to: 1) significantly increased Tz-RM-TL concentration in tumor due to its tumor-specific uptake; 2) prolonged retention of Tz-RM-TL in tumor (in traditional pre-targeting, Tz-RM is washed away immediately); 3) the possibility for internalizing Tz-RM-TL to ligate with internalized mAb inside of the tumor cells. Due to targeting of receptors overexpressed on tumor cells, it is believed that the internalizing R$_2$-RM-TL were bound and then entrapped on tumor cells, and then the bound R$_2$-RM-TL were internalized into the tumor cells and ligated with the pre-internalized mAb inside of tumor cells.

Figure 4:
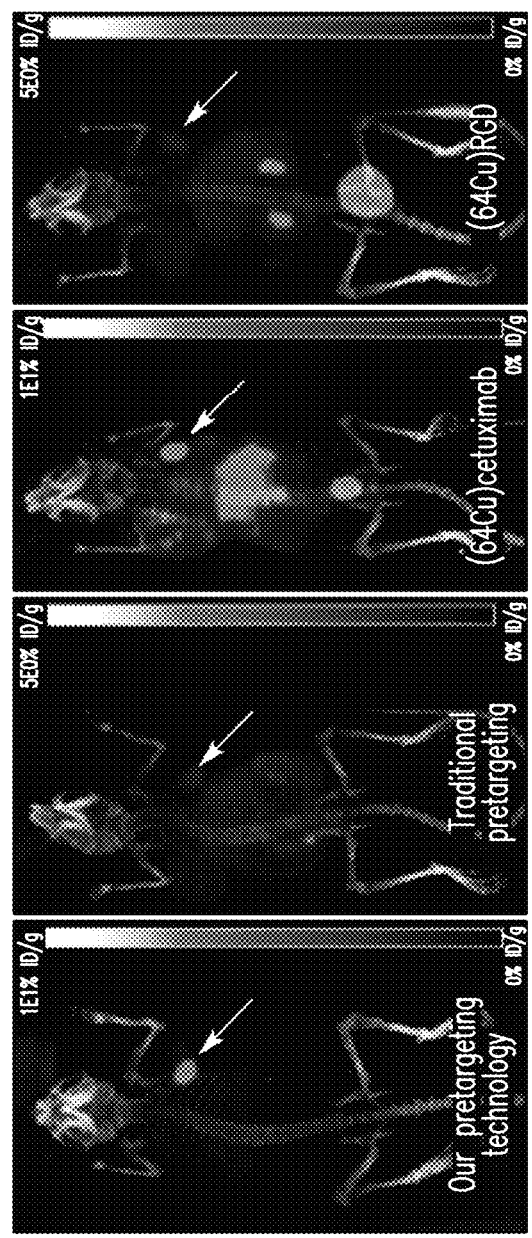

The imaging results (FIG. 4) from A) DRPT, B) traditional pre-targeting, C) direct targeting using radiolabeled cetuximab, and D) direct targeting using radiolabeled RGD, using mice bearing 4T1 (EGFR negative, on the left shoulder) and U87MG (EGFR positive, on the right shoulder) xenografts were compared. In this example, the mouse 4T1 cell line served as an internal EGFR-negative control (because the mouse EGFR expressed in 4T1 has no cross-reactivity to human anti-EGFR cetuximab), which offered an accurate comparison as the control was within the same mouse. As shown in FIG. 4, U87MG uptake from DRPT strategy (10.7±2.8. ID %/g) is comparable with (or slightly less than) that from directly radiolabeled cetuximab (13.4±3.2 ID %/g), but much higher than that from a traditional pre-targeting (1.8±0.26 ID %/g) or the directly radiolabeled RGD peptide (2.3±0.21 ID %/g). By comparing the PET/CT image FIG. 4A to FIG. 4B (current pre-targeting) and FIG. 4C (dual-receptor-targeting), it is evident that dual-receptor-targeting surprisingly performs better in vivo performance.

These results confirmed: 1) DRPT imaging significantly increased U87MG uptake and 2) the traditional pre-targeted PET imaging does not work with the internalizing cetuximab. Furthermore, DRPT also resulted in the highest tumor/ non-tumor ratios of all the strategies (FIG. 5), such as tumor/muscle (16.7±2.9) and tumor/blood (10.5±1.2). Except in FIG. 4D (direct imaging with $^{64}$Cu-NOTA-PEG4-RGD), the uptake of 4T1 (mouse cell line, in the left shoulder) was very low compared to U87MG (human cell line, in the right shoulder) in the same mouse, which can be attributed to the noncross-reactivity between human mAb cetuximab and EGFR expressed in mouse cell line 4T1. The very low uptake in 4T1 (in FIG. 4A) suggests that although the injected Tz-($^{64}$Cu)-RGD specifically bounded to 4T1, it cleared quickly because TCO-cetuximab was not available in 4T1 to ligate to the slow-clearing product (cetuximab-X-($^{64}$Cu)-RGD). FIG. 6 also looks at the comparison of uptakes and tumor/non-tumor ratios.

Additionally, in the traditional pre-targeted strategy, the uptake in U87MG was also very low (FIG. 4B, compared to those in FIGS. 4A, 4C and 4D), which could be attributed to immediately washing away of the injected Tz-(64Cu)NOTA (lack of specific binding with U87MG).

Collectively, in the DRPT imaging strategy, high specific uptake can only be observed in the tumors where the overexpressed dual-receptors are effectively targeted by a slow-clearing mAb and a fast-clearing TL, and thereby the specificity is also increased significantly. Comparing with the images (FIGS. 4B, 4C and 4D) obtained from the current imaging strategies, the one obtained from DRPT (FIG. 4A) showed not only high tumor uptake, but also substantially increased tumor/non-tumor ratios, meaning this process has great potential for PET imaging of diseases when high sensitivity and specificity are required.

Example 2: Synthesis of the Dual Receptor Radioactive Molecule

TZ-RM-TLs was prepared in three steps in high overall yields (FIG. 21):
1) $N_3$—NO'$B_2$ was conjugated to Tz-amine and then treated with trifluoroacetic acid (TFA);
2) DBCO was attached to RGD;
3) $N_3$-NOTA-Tz was click with DBCO-peptide in nearly quantitative yield.

DBCO (Click Chemistry Tools, Scottsdale, AZ) is a metal-free clicking reaction moiety. Tz-NOTA-click-PEG$_4$-RGD was radiolabeled with various PET radioisotopes: $^{64}$Cu, $^{68}$Ga $^{27}$Al, $^{18}$F. Similar to previous reports using azide containing BFCs (65,66), the triazole that formed in the click reaction greatly stabilized the resulting ($^{64}$Cu)NOTA-click complex, and in vivo metabolism studies showed that the in vivo stability of the ($^{64}$Cu)NOTA-click complex is better than (or at least comparable to) that of ($^{64}$Cu) NODAGA complex. NODAGA stands for (2,2'-(7-(1-carboxy-4-((2,5-dioxopyrrolidin-1-yl)oxy)-4-oxobutyl)-1,4,7-triazonane-1,4-diyl)diacetic acid) is a currently commonly-used chelator.

Example 3: Radioactive Labeling of the Antibody

TCO-cetuximab was prepared by incubating cetuximab with TCO-PEG$_4$-NHS (Click Chemistry Tools) overnight. TCO-cetuximab was purified using Centricon 100 centrifugal filter tubes (Millipore).

On average each cetuximab contained ~15 TCO when 100-fold TCO-PEG$_4$-NHS was added.

Example 4: Exploring Avidity Effects

Using a proper spacer (between RM and the ligand), the heterodimeric ligation product (mAb-RM-TL) formed on the tumor cells can bind to αvβ3 and EGFR simultaneously, consequently achieving avidity effect in vivo.

Due to the avidity effect, hetero-bivalency has rapidly emerged as a promising approach for molecular imaging and/or therapy. The major advantages of achieving high avidity in DRPT imaging strategy are: 1) decreased disassociation of bounded radioactivity and enhanced tumor uptake; 2) improved binding affinity on tumor cells compared to non-tumor organs that express none (or only one) of the two targeted receptors, which results in better tumor/non-tumor ratios. As shown FIG. 7, compared to DRPT PET imaging using Tz-NOTA-RGD (no PEG spacer), the imaging using Tz-NOTA-PEG$_4$-RGD showed higher tumor uptake (10.7±2.8 ID %/g vs 4.2±0.53 ID %/g), and significantly improved tumor/non-tumor ratios, e.g., tumor/blood (10.3±1.7 ID %/g vs 3.8±0.39 ID %/g).

The enhanced tumor uptake and tumor/non-tumor ratios can be attributed mainly to the avidity effect achieved by using Tz-NOTA-PEG$_4$-RGD.

Utilizing a photo-triggered metal-free click reaction between ODIBO (oxa-dibenzocyclooctynes) and azide, a generic and highly sensitive spacer optimization platform to screen high avidity heterodimeric ligand was developed. Photo-ODIBO does not react with azides, but its photo-deprotected product (ODIBO) is one of the most reactive cyclooctynes, with a cycloaddition rate of 43 $M^{-1}S^{-1}$ 72 (compared to that of widely used DBCO at ~0.36 $M^{-1}S^{-1}$ 73). This spacer-screening platform was used to optimize the spacer of heterodimer targeting to uPAR and αvβ3, and the PEG$_8$ spacer showed the highest potency based on the screening results, which is consistent with the results obtained from an in vitro evaluation (cell uptake/efflux) of the four corresponding heterodimeric radiotracers (FIG. 8).

Example 5: Photo-Triggered Dual Receptor Pre-Targeting Imaging

1. Introduction

The present example describes the development of a photo-triggered dual-receptor pre-targeting molecular imaging method in which a radioactive molecule binds to the tumor cell, but only binds to the tumor specific antibody after being photo activated.

2. Materials and Methods

Materials:

The potent biomarkers and corresponding available cell lines (both positive and negative) selected for this project are summarized in Table 3.

TABLE 3

Biomarkers, corresponding cells, and targeting probes

| | Probe | positive cells | negative cells |
|---|---|---|---|
| α,β$_3$ | Peptide: cyclco(RGDyK) (RGD) | U87MG | |
| EGFR | mAb: cetuximab | U87MG | 4T1 |

Cell lines and primary cells. All cancer cell lines in this Example was purchased from American Type Culture Collection (Manassas, VA), including human brain cancer cell line (U87MG) and mouse mammary cancer cell line 4T1. All of the cell lines were cultured according to vendor recommended growth conditions.

Radiolabeling of peptides, small molecules and/or antibodies. Due to favorable decay properties (β+: 0.653 MeV, 17.4%; β−: 0.578 MeV; 39%; t½=12.7 hr), $^{64}$Cu was used.

$^{64}$Cu labeling of the NOTA bifunctional chelator (NOTA BFC) attached bioconjugates (peptides, small molecules and antibodies) was conducted in a 0.1 M NH$_4$OAC buffer (pH=6.8). Briefly, $^{64}$CuCl$_2$ (usually in 0.1 N HCl) was first buffered in a 0.1 M NH$_4$OAC buffer (pH=6.8), and then the prepared NOTA-bioconjugates were added. The resulting mixture was vortexed for 10 sec and incubated in a thermomixer at 37° C. for 0.5 h, after which the $^{64}$Cu incorporation yield was determined by radio-HPLC.

Animal Model:

Nude mice were injected with 4T1 cells (2 million cells in 150 µL PBS) into the subcutaneous flank of the left shoulder and U87MG (5 million cells in 150 µL PBS) into the subcutaneous flank of the right shoulder.

Dual-Receptor Pre-Targeting (DRPT) Molecular Imaging Method:

The procedure of the DRPT strategy is illustrated in FIG. 3: first, Photo-OIDBO-mAb was injected into bloodstream, and after its tumor accumulation and concomitant blood clearance (1 day), a targeting-ligand containing N3-RM-TL was injected. N3 and Photo-OIDBO are a pair of bioorthogonal ligation groups that bind to each other once Photo-OIDBO is photo-triggered to OIDBO (depicted as an "X" moiety in FIG. 3). The N3-RM-TL was prepared as outlined in Example 2, except N3 was used as the bioorthogonal ligand instead of Tz. The Photo-OIDBO-mAb was prepared as outlined in Example 3 except Photo-OIDBO was used as the bioorthogonal ligand instead of TCO.

Photo-Triggering:

Photo-triggering was conducted using photon-irradiation with a UV lamp for 5 minutes to convert the Photo-OIDBO into the ODIBO.

Statistical Analysis:

All the experiments were performed in triplicated. Comparisons between different groups of experiments were made using the two-way ANOVA test (GraphPad Prism 6). When more than two data sets were compared, a two-way ANOVA analysis with Bonferroni post-tests were applied. P values <0.05 were considered statistically significant.

3. Results and Discussion

FIG. 9 presents the PET images of the mice bearing human U87MG and mouse 4T1 tumor xenografts. On the left side of FIG. 9, the use was exposed to photon-irradiation of the tumor-bottom left where the arrow for U87MG pointed to activate the bioorthogonal ligand on the cetuximab antibody, while the image on the right was taking by an animal that was not irradiated. As cetuximab is an anti-human EGFR antibody, there was no cross activity with the mouse cell line 4T1. As such 4T1 was used as a negative control to gain background information. There was high specificity for the U87MG cells in the irradiated mouse.

Example 6: Internalizing R$_2$-RM-TL Ligates to the Internalized mAB

One feature of this DRPT strategy is the use of internalizing mAb, which broadens the types of applicable monoclonal antibodies, especially when the noninternalizing mAb of the interested biomarker is not commercially available. This example looks at whether when using an internalizing antibody (e.g., cetuximab) the bound and internalized Tz-RM-RGD ligates to the pre-internalized TCO-cetuximab inside of the tumor cells, resulting in the formation of a cetuximab-X-RM-RGD (in vivo TCO/Tz ligation product).

In order to examine this, fluorogenic light-triggered photoclick chemistry was used to provide evidence of the ligation between the two internalizing species (Tz-RM-RGD and TCO-cetuximab) inside of tumor cells. In particular, one type of photoclick chemistry that enables rapid ligation of two bioorthogonal moieties upon irradiation with UV light was used. This light-triggered fluorogenic reaction is a tool to detect ligation inside of a living U87MG cell between two internalizing ligands, such as αvβ3-targeted RGD and EGFR-targeted cetuximab. By utilizing the proposed photoclick chemistry, an optical-PET dual-modality imaging agent was prepared in 1 min under the radiation of a 254-nm UV handheld lamp in PBS buffer. As shown in FIG. 10, the excitation and emission wavelengths of the resulting photoclick product (SLY-86) were 370 nm and 580 nm, respectively, and it was successfully used in the confocal microscopy imaging of a U87MG cell, which demonstrated the photophysical properties of this photoclick product was compatible with the confocal microscope.

Example 7: Exploring Spacer Lengths

Eight NH$_2$-PEGn-RGD peptides containing spacers of various PEG lengths (n=2, 4, 6, 8, 10, 12, 14, 16) will be prepared by adding the corresponding Boc-PEGn-NHS to RGD in a PBS buffer (pH=8.2), followed by Boc deprotection. Photo-ODIBO-NHS, prepared using previously reported procedures, will then be mixed with the prepared NH$_2$-PEGn-RGD in a PBS buffer (pH=8.2) to produce photo-OIDBO-PEGn-RGD. N$_3$-PEG$_4$-cetuximab will be prepared using previously reported procedures. N$_3$-PEG$_4$-cetuximab and the eight photo-ODIBO-PEGn-RGD peptides (n=2, 4, 6, 8, 10, 12, 14, 16) will be used for in vitro screening (at 4° C. to minimize the internalization of targeting probes). As shown in FIG. 11: 1): eight mixed-ligands stock solutions will be prepared by mixing N$_3$-PEG$_4$-cetuximab with one of the eight photo-OIDBO-PEGn-RGD peptides; 2) U87MG cells will be cultured in a 96-well plate; 3) one of the above eight mixed-ligands stock solution will be added into each well (eight wells in total) pre-seeded with U87MG; 2) after the ligands bind to the targeted receptors, the excess (unbound) targeting ligands will be washed off using a PBS buffer (repeated 5 times to ensure complete removal); 3) a UV lamp (365 nm) will be applied to deprotect the azide-inactive photo-ODIBO and generate azide-active "ODIBO", subsequently triggering ligation between the N$_3$-PEG$_4$-cetuximab and ODIBO-PEGn-RGD; 4) after being incubated for an additional 2 h, $^{64}$Cu-labeled N$_3$-NOTA will be added to click with the "excess" ODIBO-PEGn-RGD (that binds to cells, but does not click to N$_3$-PEG$_4$-cetuximab); and 5) the excess N$_3$-($^{64}$Cu)NOTA will be removed, and the N$_3$-($^{64}$Cu)NOTA clicked to "excess" ODIBO-PEGn-RGD will be measured on Micro-Beta2 Plate Counter. One group without UV irradiation will be used as a negative control to get counts from the non-specific binding of N$_3$-($^{64}$Cu)NOTA. After subtracting the non-specific binding, the specific binding of N$_3$-($^{64}$Cu)NOTA obtained from the eight ODIBO-PEGn-RGD (n=2, 4, 6, 8, 10, 12, 14, 16) will be compared. The well with the lowest specific binding will contain the highest amount of clicking product (between cetuximab-PEG$_4$-N$_3$ and ODIBO-PEGn-RGD), thus the corresponding spacer will be the most potent.

The ODIBO-PEGn-RGD containing the most potent PEG spacer will click with Tz-NOTA-N3 and then be radiolabeled with $^{64}$Cu, and the resulting Tz-($^{64}$Cu)NOTA-PEGn-RGD will be used for the in vitro avidity studies on U87MG cells. Tz-($^{64}$Cu)NOTA-RGD (without a PEG spacer) will be used as a negative control because the distance between RGD and cetuximab in the resulting heterodimer is too short to achieve avidity effect (proved in preliminary study, FIG. 5B). Briefly, Tz-($^{64}$Cu)NOTA-PEGn-RGD/TCO-PEG4-cetuximab ligation product (cetuximab-PEG4-($^{64}$Cu)NOTA-PEGn-RGD) will be used for cell uptake/efflux, binding affinity and Bmax measurements on U87MG cells. After high avidity effect is confirmed on the above ligation product, in vivo evaluation will be performed then. Mice bearing U87MG xenografts will be pre-injected with 100 μg of TCOPEG$_4$-cetuximab, and 24 h later, ~250-350 μCi of Tz-($^{64}$Cu)NOTA-PEGn-RGD (or Tz-($^{64}$Cu)NOTA-RGD in the negative control group) will be injected. Then 1 h dynamic PET scans will be performed at multiple time points (p.i., 4, 18, and/or 28h). As cetuximab is cleared through the liver, kinetics on tumor and liver at mid and late time points can be evaluated. At mid/late time points (4, 18, 28h) when most of the un-ligated Tz-($^{64}$Cu)NOTAPEGn-RGD has been washed off, observation of relatively slower tumor washing out and faster liver clearing (compared to that from Tz-($^{64}$Cu)NOTA-RGD) can indicate the much stronger binding with tumor cells, and thus an avidity effect of in vivo ligation product (cetuximab-PEG2-($^{64}$Cu)NOTA-PEGn-RGD) is being achieved.

Another of the expected results of avidity effect is that the decreased uptake on non-tumor organs that express none (or only one) of the dual-targeted receptors, which has been observed in Example 1.

Example 8: High-Throughput Screening Platform for Heterodimer Spacer Optimization A high throughput cell-based universal platform for rapid heterodimer spacer optimization has been developed to generate heterodimers with high avidity effects. By using the developed platform, the repetition of the traditional approach, which requires repeated synthesis and evaluation of a heterodimer library, is avoided. The platform can screen heterodimers with various spacers to identify a heterodimer with the best performance in in vitro and/or in vivo evaluations. Although this example describes spacer optimization with reference to a heterodimer comprising two peptide ligands, a person of skill will appreciate that these methods can be modified to other heterodimers, e.g., comprising an antibody and a peptide ligand.

Methodology

Two ligands of interest, RGD (targeting to integrin $α_vβ_3$) and AE105 (targeting to urokinase-type plasminogen activator receptor (uPAR)), were functionalized with a photo ODIBO group and N$_3$ group, respectively, for the in-situ formation of a heterodimer. Herein, the photo-ODIBO group is a photo-triggered metal-free click chemistry moiety, which can be deprotected to ODIBO and react with azide via the strain-promoted alkyne-azide cycloadditions (SPAAC) upon UV 365 nm irradiation. To offer the capability of high-throughput screening and facilitate its application in research groups, the preparation of chemical tools was designed to avoid complex purifications (see FIG. 20). In particular, photo-ODIBO-PEG$_4$-RGD was prepared via treating RGD dissolved in DMSO with 6 eqv. DIEA and 3 eqv. ODIBO-PEG$_4$-NHS. After the pegylation was completed, 1×PBS was added to the reaction mixture so that the excess photo-ODIBO-PEG$_4$-NHS could be hydrolyzed to non-cell reactive photo-ODIBO-PEG$_4$-COOH. Parallel synthesis of four N$_3$ functionalized AE105 analogues with different spacers was conducted via in a similar way via incubating AE105 with N$_3$-PEG$_n$-NHS (one of the four selected PEG spacers for each analogue), followed by hydrolyzing excess NHS with 1×PBS. Without further purification, the resulting photo-ODIBO-PEG$_4$-RGD and four N$_3$-PEG$_{Pn}$-AE105 solutions could be directly applied in the following heterodimer spacer optimization experiments.

Spacer optimization was performed as illustrated in FIG. 14: the photo-ODIBO-PEG$_4$-RGD and one of the N$_3$-PEGn-AE105 prepared above were mixed and then added into a 96-well plate that pre-seeded with u87MG cells (a human brain cancer cell line which over expressed both integrin $αvβ3$ receptor and uPAR). Those cells were pre-fixed with 4% paraformaldehyde to minimize the internalization. After a 2h incubation to allow sufficient binding of RGD and AE105 to integrin $α_vβ_3$ and uPAR respectively, the excess (unbound) ligands were washed off using PBS buffer. Then the plate was irradiated with a UV lamp (365 nm) for 2 minutes to deprotect the azide-inactive photo-ODIBO to the azide-active "ODIBO", triggering the metal-free click reaction between the N$_3$-PEG$_n$-AE105 and the ODIBO-PEG$_4$-RGD. After being incubated for an additional 2 h to allow the completion of the metal-free click reactions, ($^{64}$Cu)NOTA-N$_3$ was added as a radio scavenger to click with the "excess" ODIBO-PEG$_4$-RGD (that binds to cells, but did not click with N$_3$-PEG$_n$-AE105). Upon the removal of unbound ($^{64}$Cu)NOTA-N$_3$, the ($^{64}$Cu)NOTA-N$_3$ clicked to ODIBO-PEGn-RGD was measured on MicroBeta2 Plate Counter. One group without UV irradiation was used as a background control to get counts resulting from the non-specific binding of ($^{64}$Cu)NOTA-N$_3$. After subtracting the background counts due to the non-specific binding, the well with the lowest radioactivity counts contained the least amount of ($^{64}$Cu)NOTA-click-PEG4-RGDso as the highest amount of the in situ generated heterodimer (AE105-PEG$_n$-click-PEG$_4$-RGD), indicating the corresponding spacer length (PEG$_{n+4}$) will be the most suitable for achieving high avidity.

Compared with the traditional strategy, this platform avoided the abundant synthesis and evaluation of a heterodimer library consisting of heterodimers bearing varied spacers. In addition, owning to the high sensitivity of the beta counter, ligands were consumed at a nanomole scale for each test so that the cost of expensive starting materials was significantly reduced. Taking into account advantages of convenience, sensitivity, and capability on high throughput screening, this universal rapid spacer optimization platform can greatly facilitate the development of heterodimeric pharmaceuticals for research and/or clinical applications.

Results and Discussion

Firstly, the distance between one integrin $αvβ3$ receptor and one uPAR on a cell surface was estimated to select spacers of proper length for screening, and it was found that the possible distance between two receptors could be 5 nm or less. Given that the length of a single bond was around 1.5 Å (0.15 nm), the length of a PEG$_4$ unit consisting of 12 single bonds would be around 1.2 nm, when taking the bond angle into account. Therefore, to cover the length from 1 nm to 5 nm, 4 spacers consisting of PEG$_4$, PEG$_8$, PEG$_{12}$, and PEG$_{16}$ were selected for the screening purpose (see Table 2).

TABLE 2

Spacers selected for in vitro screening

| entrance | PEG units attached to RGD | PEG units attached to AE105 | Total PEG units | Estimated length (nm) |
|---|---|---|---|---|
| 1 | 4 | 0 | 4 | 1.2 |
| 2 | 4 | 4 | 8 | 2.4 |
| 3 | 4 | 8 | 12 | 3.6 |
| 4 | 4 | 12 | 16 | 4.8 |

Then RGD-PEG$_4$-photo-ODIBO and AE105-PEGn-N$_3$ (n=0, 4, 8, and 12) were prepared as shown in FIG. 20. Due to the use of 3 eqv. R-PEG-NHS ester, conversion yields of peptidic ligands reached above 95% within 30 minutes, as monitored by HPLC. FIG. 15 shows an example of converting RGD into RGD-PEG$_4$-photo-ODIBO, in which RGD, RGD-PEG$_4$-photo-ODIBO, photo-ODIBO-PEG$_4$-COOH, and photo-ODIBO-PEG$_4$-NHS were eluted at 13, 19, 20, and 21 minutes respectively. In FIG. 15, the HPLC conditions were as follows: 0-2 minutes, 100% H$_2$O; 2-12 minutes, changing from 100% H$_2$O to 80% H$_2$O and 20% ACN; 12-22 minutes, changing from 80% H$_2$O and 20% ACN to 10% H$_2$O and 90% ACN; 22-26 minutes, 10% H$_2$O and 90% ACN; 26-27 minutes changing from 10% H$_2$O and 90% ACN to 100% H$_2$O; 27-35 minutes, 100% H$_2$O with a flow rate of 1.5 ml/min. Based on the quantitative results obtained from the HPLC spectra, after the reaction mixture was stirred for 0.5h at room temperature, the RGD conversion yield was above 95%, and less than 5% photo-ODIBO-PEG$_4$-NHS was hydrolyzed to photo-ODIBO-PEG$_4$-COOH.

After the addition of 1×PBS, the reaction mixture was allowed to stand overnight to maximize hydrolysis of photo-ODIBO-PEG$_4$-NHS, and only RGD-PEG$_4$-photo-ODIBO as well as photo-ODIBO-PEG$_4$-COOH remained in the reaction mixture. Similar observations were obtained when the AE105-PEG$_n$-N$_3$ (n=0, 4, 8, and 12) was prepared. Because neither photo-ODIBO-PEG$_4$-COOH nor N$_3$-PEG$_n$-COOH would bind to cells due to the lack of a targeting ligand, they were washed away together with unbound RGD-PEG$_4$-photo-ODIBO or AE105-PEG$_n$-N$_3$. Therefore, the resulting five reaction mixtures can be directly applied in the cell based screening without further purification.

Subsequently, the RGD-PEG$_4$-photo-ODIBO was parallelly mixed with either AE105-PEG$_0$-N$_3$ or AE105-PEG$_4$-N$_3$ or AE105-PEG$_8$-N$_3$ or AE105-PEG$_{12}$-N$_3$, resulting in four groups of stock solutions each containing both RGD-PEG4-photo-ODIBO and one of the AE105-PEG$_n$-N$_3$ (n=0, 4, 8, 12). As illustrated in FIG. 14, the four groups of stock solutions were applied in the designed cell based screening assay using u87MG cells pre-fixed with 4% paraformaldehyde. In addition to the four experimental groups, a negative control group was prepared in which cells were treated with RGD-PEG$_4$-photo-ODIBO and NH$_2$-PEG$_0$-AE105; thus, no heterodimer could be generated in this negative control group as there was no ligation between ODIBO and NH$_2$. Additionally, there was a background control group, in which no UV irradiation was applied; thus, the amount of ($^{64}$Cu)NOTA-N$_3$ detected was caused by its non-specific binding on cells. After subtracting the non-specific binding recorded in the background control group, the specific bindings of ($^{64}$Cu)NOTA-N$_3$ in different groups caused by its ligation with the RGD-PEG$_4$-ODIBO were compared. As shown in FIG. 16, the groups treated with N$_3$-PEG$_4$-AE105 and N$_3$-PEG$_8$-AE105 exhibited less amount of the specific binding of ($^{64}$Cu)NOTA-N3, suggesting that RGD-PEG$_8$-AE105 and RGD-PEG$_{12}$-AE105 were the two most abundant heterodimers formed on u87MG cells. Accordingly, the two corresponding spacers (entrance 2 & 3) were the most potent among the four tested spacers.

Finally, the result obtained from the above screening assay was validated both in vitro and in vivo. The four RGD-AE105 heterodimers possessing various PEG spacers (PEG$_4$, PEG$_8$, PEG$_{12}$ and PEG$_{16}$, respectively) were prepared as described in the previous examples. The prepared heterodimers were then radiolabeled with either Cu-64 or Ga-68 for in vitro and in vivo evaluation respectively. Based on the cell uptake result as shown in FIG. 17A, the PEG$_{16}$-containing heterodimer exhibited the highest cell uptake, followed by the PEG$_{12}$-, PEG$_8$-, and PEG$_4$-contained heterodimers with 4 h uptake values of 0.46%, 0.38%, 0.24% and 0.16% respectively. In the cell efflux study (FIG. 17B), the PEG$_8$ and PEG$_{12}$-containing heterodimers showed the best cell retention, followed by the PEG$_4$-, and PEG$_{16}$-containing heterodimers with 2 h retention values of 44%, 43%, 35% and 26%, respectively. Taking into account both the cell uptake and efflux results among the four tested heterodimers, the PEG$_{12}$-containing heterodimer demonstrated the highest potential in this in vitro evaluation, consistant with the result obtained from the designed cell based screening assay.

Further in vivo validation was conducted by comparing PET imaging results obtained from mice bearing u87MG xenografts. As shown in FIG. 18, tumors could be visualized by using all the four tested heterodimeric PET tracers while the PEG$_{12}$-contained heterodimer exhibited the highest tumor to background contrast, followed by the PEG$_8$-, PEG$_{16}$-, and PEG$_4$-containing heterodimers. Quantitative tumor uptake values were subsequently revealed by the region of interest (ROI) analysis (FIG. 19). The tumor uptake value of the PEG$_{12}$-containing heterodimer was 2.8%, while those of PEG$_8$-, PEG$_{16}$-, and PEG$_4$-containing heterodimers were 2.4%, 2.10% and 1.7%, respectively, reaffirming the result obtained from the designed cell based screening assay. Collectively, results from both in vitro and in vivo evaluations successfully validated the accuracy and reliability of the rapid spacer-optimization platform. The selected AE105-PEG$_{12}$-RGD was further compared with two corresponding monomer AE105 and RGD via PET imaging of u87MG xenografts on nude mice. Superior imaging results were obtained in mice administrated with the heterodimer, indicating its better in vivo performance than the two monomer counterparts due to the avidity effects.

Thus, using a photo-triggered metal-free click reaction, a universal in vitro screening platform can be established for simplifying the spacer optimization process involved in developing high avidity heterodimers, which can be broadly applied to various dual-biomarker combinations and different diseases. The developed screening platform was successfully applied in the spacer optimization of the integrin α$_v$β$_3$-uPAR dual-targeted heterodimeric ligand. The accuracy and reliability of this platform was further validated via both in vitro and in vivo evaluations, in which heterodimers containing all the tested spacers were prepared and evaluated individually. In addition to the demonstrated capability of high throughput screening (as shown in FIG. 14), this universal platform can significantly accelerate and/or enhance the application of the dual-receptor-targeting strategy in various biomedical fields, particularly when targeted receptors are expressed in low abundance and/or when high affinity (and/or specificity) monovalent ligands are not available.

7. REFERENCES

1. Goldenberg, D. M. et al. Use of radio-labeled antibodies to carcinoembryonic antigen for the detection and localization of diverse cancers by external photoscanning. New England Journal of Medicine 298, 1384-1388 (1978).
2. Goldenberg, D. M. Cancer imaging with CEA antibodies: historical and current perspectives. The International journal of biological markers 7, 183-188 (1992).
3. Goldenberg, D. M. & Larson, S. M. Radioimmunodetection in cancer identification. Journal of nuclear medicine: official publication, Society of Nuclear Medicine 33, 803-814 (1992).
4. Larson, S. M. et al. PET scanning of iodine-124-3F9 as an approach to tumor dosimetry during treatment planning for radioimmunotherapy in a child with neuroblastoma. Journal of nuclear medicine: official publication, Society of Nuclear Medicine 33, 2020 (1992).
5. Robinson, M. K. et al. Quantitative immuno-positron emission tomography imaging of HER2-positive tumor xenografts with an iodine-124 labeled anti-HER2 diabody. Cancer research 65, 1471-1478, doi: 10.1158/0008-5472.CAN-04-2008 (2005).
6. Reardan, D. T. et al. Antibodies against metal chelates. Nature 316, 265-268 (1985).
7. Goodwin, D. A., Mears, C. F., McTigue, M. & David, G. S. Monoclonal antibody hapten radiopharmaceutical delivery. Nuclear medicine communications 7, 569-580 (1986).
8. Goodwin, D. A., Meares, C. F., McCall, M. J., McTigue, M. & Chaovapong, W. Pre-targeted immunoscintigraphy of murine tumors with indium-111-labeled bifunctional haptens. Journal of nuclear medicine: official publication, Society of Nuclear Medicine 29, 226-234 (1988).
9. Knight, J. C. & Cornelissen, B. Bioorthogonal chemistry: implications for pretargeted nuclear (PET/SPECT) imaging and therapy. American journal of nuclear medicine and molecular imaging 4, 96-113 (2014).
10. Carroll, L., Evans, H. L., Aboagye, E. O. & Spivey, A. C. Bioorthogonal chemistry for pre-targeted molecular imaging-progress and prospects. Organic & biomolecular chemistry 11, 5772-5781, doi:10.1039/c3ob40897c (2013).
11. Sharkey, R. M. et al. Signal amplification in molecular imaging by pretargeting a multivalent, bispecific antibody. Nature medicine 11, 1250-1255, doi:10.1038/nm1322 (2005).
12. Goldenberg, D. M. et al. Pretargeted molecular imaging and radioimmunotherapy. Theranostics 2, 523-540, doi: 10.7150/thno.3582 (2012).
13. Evans, H. L. et al. A bioorthogonal (68)Ga-labelling strategy for rapid in vivo imaging. Chemical communications 50, 9557-9560, doi:10.1039/c4cc03903c (2014).
14. Rossin, R. et al. In vivo chemistry for pretargeted tumor imaging in live mice. Angewandte Chemie 49, 3375-3378, doi:10.1002/anie.200906294 (2010).
15. Zeglis, B. M. et al. A pretargeted PET imaging strategy based on bioorthogonal Diels-Alder click chemistry. Journal of nuclear medicine: official publication, Society of Nuclear Medicine 54, 1389-1396, doi:10.2967/jnumed.112.115840 (2013).
16. Zeglis, B. M. et al. Optimization of a Pretargeted Strategy for the PET Imaging of Colorectal Carcinoma via the Modulation of Radioligand Pharmacokinetics. Molecular pharmaceutics 12, 3575-3587, doi:10.1021/acs.molpharmaceut.5b00294 (2015).
17. Meyer, J. P. et al. 18F-Based Pretargeted PET Imaging Based on Bioorthogonal Diels-Alder Click Chemistry. Bioconjugate chemistry, doi:10.1021/acs.bioconjchem.5b00504 (2015).
18. Rossin, R., van Duijnhoven, S. M. J., van den Bosch, S. M. & Robillard, M. S. Tumor pretargeting with Diels-Alder: A TCO derivative with improved properties. Nuclear Medicine and Biology 41, 630, doi:10.1016/j.nucmedbio.2014.05.017.
19. Rossin, R., van Duijnhoven, S. M., Lappchen, T., van den Bosch, S. M. & Robillard, M. S. Trans-cyclooctene tag with improved properties for tumor pretargeting with the diels-alder reaction. Molecular pharmaceutics 11, 3090-3096, doi:10.1021/mp500275a (2014).
20. Rossin, R., Lappchen, T., van den Bosch, S. M., Laforest, R. & Robillard, M. S. Diels-Alder reaction for tumor pretargeting: in vivo chemistry can boost tumor radiation dose compared with directly labeled antibody. Journal of nuclear medicine: official publication, Society of Nuclear Medicine 54, 1989-1995, doi:10.2967/jnumed.113.123745 (2013).
21. Rossin, R. et al. Highly reactive trans-cyclooctene tags with improved stability for Diels-Alder chemistry in living systems. Bioconjugate chemistry 24, 1210-1217, doi:10.1021/bc400153y (2013).
22. Girgis, M. D. et al. CA19-9 as a Potential Target for Radiolabeled Antibody-Based Positron Emission Tomography of Pancreas Cancer. International journal of molecular imaging 2011, 834515, doi:10.1155/2011/834515 (2011).
23. Lamberts, L. E. et al. Antibody positron emission tomography imaging in anticancer drug development. Journal of clinical oncology: official journal of the American Society of Clinical Oncology 33, 1491-1504, doi:10.1200/JCO.2014.57.8278 (2015).
24. Den, M. A., Zeglis, B. M., Francesconi, L. C. & Lewis, J. S. PET imaging with (8)(9)Zr: from radiochemistry to the clinic. Nucl Med Biol 40, 3-14, doi:10.1016/j.nucmedbio.2012.08.004 (2013).
25. Zeng, D., Zeglis, B. M., Lewis, J. S. & Anderson, C. J. The growing impact of bioorthogonal click chemistry on the development of radiopharmaceuticals. Journal of nuclear medicine: official publication, Society of Nuclear Medicine 54, 829-832, doi:10.2967/jnumed.112.115550 (2013).
26. Pfeifer, A. et al. Clinical PET of neuroendocrine tumors using 64Cu-DOTATATE: first-in-humans study. Journal of Nuclear Medicine 53, 1207-1215 (2012).
27. Persson, M. et al. First-in-human uPAR PET: Imaging of Cancer Aggressiveness. Theranostics 5, 1303-1316, doi: 10.7150/thno.12956 (2015).
28. Gai, Y., Sun, L., Xiang, G., Ma, X. & Zeng, D. Novel TACN chelator: a scaffold designed for dual-receptor targeted PET imaging. Journal of Nuclear Medicine 56, 1053-1053 (2015).
29. Siegel, R., Ma, J., Zou, Z. & Jemal, A. Cancer statistics, 2014. CA: a cancer journal for clinicians 64, 9-29, doi: 10.3322/caac.21208 (2014).
30. Ghadirian, P., Lynch, H. T. & Krewski, D. Epidemiology of pancreatic cancer: an overview. Cancer detection and prevention 27, 87-93 (2003).

31 Michaud, D. S. Epidemiology of pancreatic cancer. Minerva Chir 59, 99-111 (2004).

32 Sohn, T. A. et al. Resected adenocarcinoma of the pancreas-616 patients: results, outcomes, and prognostic indicators. J Gastrointest Surg 4, 567-579 (2000).

33 Ariyama, J., Suyama, M., Satoh, K. & Sai, J. Imaging of small pancreatic ductal adenocarcinoma. Pancreas 16, 396-401 (1998).

34 Neoptolemos, J. P. et al. A randomized trial of chemoradiotherapy and chemotherapy after resection of pancreatic cancer. N Engl J Med 350, 1200-1210, doi:10.1056/NEJMoa032295350/12/1200 [pii] (2004).

35 Egawa, S. et al. Clinicopathological aspects of small pancreatic cancer. Pancreas 28, 235-240 (2004).

36 Hutchinson, L. Imaging: PET is prognostic of survival in pancreatic cancer patients. Nat Rev Clin Oncol 7, 551, doi:10.1038/nrclinonc.2010.150 (2010).

37 Goggins, M. Identifying molecular markers for the early detection of pancreatic neoplasia. Seminars in oncology 34, 303-310, doi:10.1053/j.seminoncol.2007.05.003 (2007).

38 Kelly, K. A. et al. Targeted nanoparticles for imaging incipient pancreatic ductal adenocarcinoma. PLoS medicine 5, e85, doi:10.1371/joumal.pmed.0050085 (2008).

39 Desgrosellier, J. S. & Cheresh, D. A. Integrins in cancer: biological implications and therapeutic opportunities. Nature Reviews Cancer 10, 9-22 (2010).

40 Brooks, P. C. Role of integrins in angiogenesis. European journal of cancer 32A, 2423-2429 (1996).

41 Mizejewski, G. J. Role of integrins in cancer: survey of expression patterns. Proceedings of the Society for Experimental Biology and Medicine. Society for Experimental Biology and Medicine 222, 124-138 (1999).

42 Brooks, P. C., Clark, R. A. & Cheresh, D. A. Requirement of vascular integrin alpha v beta 3 for angiogenesis. Science 264, 569-571 (1994).

43 Hosotani, R. et al. Expression of integrin alphaVbeta3 in pancreatic carcinoma: relation to MMP-2 activation and lymph node metastasis. Pancreas 25, e30-35 (2002).

44 Kubas, H. et al. Multivalent cyclic RGD ligands: influence of linker lengths on receptor binding. Nucl Med Biol 37, 885-891, doi:10.1016/j.nucmedbio.2010.06.005 (2010).

45 Haubner, R. et al. Noninvasive visualization of the activated alphavbeta3 integrin in cancer patients by positron emission tomography and [18F]Galacto-RGD. PLoS medicine 2, e70, doi:10.1371/journal.pmed.0020070 (2005).

46 Chen, H., Niu, G., Wu, H. & Chen, X. Clinical Application of Radiolabeled RGD Peptides for PET Imaging of Integrin alphavbeta3. Theranostics 6, 78-92, doi:10.7150/thno.13242 (2016).

47 Li, Z. B. et al. (64)Cu-labeled tetrameric and octameric RGD peptides for small-animal PET of tumor alpha(v)beta(3) integrin expression. Journal of nuclear medicine: official publication, Society of Nuclear Medicine 48, 1162-1171, doi:10.2967/jnumed.107.039859 (2007).

48 Yoshimoto, M. et al. In vivo SPECT imaging with 111In-DOTA-c(RGDfK) to detect early pancreatic cancer in a hamster pancreatic carcinogenesis model. Journal of nuclear medicine: official publication, Society of Nuclear Medicine 53, 765-771, doi:10.2967/jnumed.111.099630 (2012).

49 Trajkovic-Arsic, M. et al. Multimodal molecular imaging of integrin alphavbeta3 for in vivo detection of pancreatic cancer. Journal of nuclear medicine: official publication, Society of Nuclear Medicine 55, 446-451, doi:10.2967/jnumed.113.129619 (2014).

50 Lurje, G. & Lenz, H. J. EGFR signaling and drug discovery. Oncology 77, 400-410, doi:10.1159/000279388 (2009).

51 Mendelsohn, J. & Baselga, J. Epidermal growth factor receptor targeting in cancer. Seminars in oncology 33, 369-385, doi:10.1053/j.seminoncol.2006.04.003 (2006).

52 Ciardiello, F. & Tortora, G. EGFR antagonists in cancer treatment. N Engl J Med 358, 1160-1174, doi:10.1056/NEJMra0707704 (2008).

53 Hynes, N. E. & Lane, H. A. ERBB receptors and cancer: the complexity of targeted inhibitors. Nature reviews. Cancer 5, 341-354, doi:10.1038/nrc1609 (2005).

54 Ali, S., El-Rayes, B. F., Sarkar, F. H. & Philip, P. A. Simultaneous targeting of the epidermal growth factor receptor and cyclooxygenase-2 pathways for pancreatic cancer therapy. Molecular cancer therapeutics 4, 1943-1951, doi:10.1158/1535-7163.MCT-05-0065 (2005).

55 Xiong, H. Q. et al. Cetuximab, a monoclonal antibody targeting the epidermal growth factor receptor, in combination with gemcitabine for advanced pancreatic cancer: a multicenter phase II Trial. Journal of clinical oncology: official journal of the American Society of Clinical Oncology 22, 2610-2616, doi:10.1200/JCO.2004.12.040 (2004).

56 Castanon, E. et al. Epidermal Growth Factor Receptor targeting in non-small cell lung cancer: revisiting different strategies against the same target. Current drug targets 15, 1273-1283 (2014).

57 Chang, A. J., De Silva, R. A. & Lapi, S. E. Development and characterization of 89Zr-labeled panitumumab for immuno-positron emission tomographic imaging of the epidermal growth factor receptor. Molecular imaging 12, 17-27 (2013).

58 Zeng, D. et al. Comparison of conjugation strategies of cross-bridged macrocyclic chelators with cetuximab for copper-64 radiolabeling and PET imaging of EGFR in colorectal tumor-bearing mice. Molecular pharmaceutics 11, 3980-3987, doi:10.1021/mp500004m (2014).

59 Cascinu, S. et al. Cetuximab plus gemcitabine and cisplatin compared with gemcitabine and cisplatin alone in patients with advanced pancreatic cancer: a randomised, multicentre, phase II trial. The Lancet. Oncology 9, 39-44, doi:10.1016/S1470-2045(07)70383-2 (2008).

60 Cohen, R. et al. Inert coupling of IRDye800CW to monoclonal antibodies for clinical optical imaging of tumor targets. EJNMMI research 1, 31, doi:10.1186/2191-219X-1-31 (2011).

61 Menke-van der Houven van Oordt, C. W. et al. 89Zr-cetuximab PET imaging in patients with advanced colorectal cancer. Oncotarget 6, 30384-30393, doi:10.18632/oncotarget.4672 (2015).

62 Ping Li, W., Meyer, L. A., Capretto, D. A., Sherman, C. D. & Anderson, C. J. Receptor-binding, biodistribution, and metabolism studies of 64Cu-DOTA-cetuximab, a PET-imaging agent for epidermal growth-factor receptor-positive tumors. Cancer biotherapy & radiopharmaceuticals 23, 158-171, doi:10.1089/cbr.2007.0444 (2008).

Various references are cited in this document, which are hereby incorporated by reference in their entireties herein.

What is claimed is:

1. A composition comprising:
   a. a first targeting probe comprising:
      i) an antibody or fragment thereof targeting a first cancer antigen, and
      ii) a first bioorthogonal ligation moiety; and
   b. a second targeting probe comprising:
      i) a peptide targeting a second cancer antigen,
      ii) a second bioorthogonal ligation moiety, and
      iii) a detectable label;
   wherein the antibody of fragment thereof is selected from the group consisting of cetuximab, pertuzumab, trastuzumab, bevacizumab, mAb 8G7, 1116NS19-9, CP-870,893, atezolizumab, UMB2, etaracizumab, and E398P
   wherein the peptide is selected from the group consisting of LLP2A, AE105, BBN(7-14), tyr(3)-octreotate, DAPTA, T140, CPCR4-2, RGD, cyclo(RGDyK), and PTP;
   wherein the first bioorthogonal ligation moiety is selected from the group consisting of trans-cyclooctene, cyclooctyne, alkyne, alkene, photo-DIBO, cycloproperone, oxa-dibenzocyclooctyne, and dibenzocyclooctyne, and the second bioorthogonal ligation moiety is selected from the group consisting of tetrazine, azide, tetrazole, and photo-tetrazole.

2. The composition of claim 1, wherein the first and second cancer antigens are selected from the group consisting of integrin, uPAR, gastrin-releasing peptide (GRP), SSTR2, folate receptor, CCR5, CXCR4, plectin-1, EGFR, VEGF, MUC4, CA19-9, CD40, PD-L1.

3. The composition of claim 1, wherein the detectable label is $^{110}$In, $^{111}$In, $^{177}$Lu, $^{52}$Fe, $^{62}$Cu, $^{64}$Cu, $^{32}$P, 11C, $^{13}$N, $^{15}$O, $^{67}$Cu, $^{67}$Ga, $^{68}$Ga, $^{86}$Y, $^{90}$Y, $^{18}$F, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, $^{211}$At, $^{212}$Bi or $^{225}$Ac.

4. The composition of claim 1, wherein the first bioorthogonal ligation moiety is cyclooctyene and the second bioorthogonal ligation moiety is azide.

5. The composition of claim 1, wherein the antibody is cetuximab and the peptide is cyclo(RGDyK).

6. A composition comprising:
   a. a first targeting probe comprising:
      i) an antibody or fragment thereof targeting a first cancer antigen, and
      ii) a first bioorthogonal ligation moiety; and
   b. a second targeting probe comprising:
      i) a peptide targeting a second cancer antigen,
      ii) a second bioorthogonal ligation moiety, and
      iii) optionally a detectable label;
   wherein the antibody or fragment thereof is selected from the group consisting of cetuximab, pertuzumab, trastuzumab, bevacizumab, mAb 8G7, 1116NS19-9, CP-870,893, atezolizumab, UMB2, etaracizumab, and E398P;
   wherein the peptide is selected from the group consisting of LLP2A, AE105, BBN(7-14), tyr(3)-octreotate, DAPTA, T140, CPCR4-2, RGD, cyclo(RGDyK), and PTP;
   wherein the first bioorthogonal ligation moiety is selected from the group consisting of trans-cyclooctene, cyclooctyne, alkyne, alkene, photo-DIBO, cycloproperone, oxa-dibenzocyclooctyne, and dibenzocyclooctyne, and the second bioorthogonal ligation moiety is selected from the group consisting of tetrazine, azide, tetrazole, and photo-tetrazole.

7. The composition of claim 6, wherein the second targeting probe further comprises a therapeutic active agent, wherein the therapeutic active agent is selected from the group consisting of lapatinib, afatinib, dacomitinib, KD-019 erlotinib, cisplatin, carboplatin, gemcitabine, pemetrexed, irinotecan, 5-fluoruracil, paclitaxel, docetaxel, and capecitabine.

8. The composition of claim 6, wherein the second targeting probe further comprises a detectable label selected from the group consisting of $^{110}$In, $^{11}$In, $^{177}$Lu, $^{52}$Fe, $^{62}$Cu, $^{64}$Cu, $^{32}$P, 11C, $^{13}$N, $^{15}$O, $^{67}$Cu, $^{67}$Ga, $^{68}$Ga, $^{86}$Y, $^{90}$Y, $^{18}$F, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, $^{211}$At, $^{212}$Bi, and $^{225}$Ac.

9. The composition of claim 7, wherein the second targeting probe further comprises a therapeutic radioisotope selected from the group consisting of $^{110}$In, $^{111}$In, $^{177}$Lu, $^{52}$Fe, $^{62}$Cu, $^{64}$Cu, $^{32}$P, 11C, $^{13}$N, $^{15}$O, $^{67}$Cu, $^{67}$Ga, $^{68}$Ga, $^{86}$Y, $^{90}$Y, $^{18}$F, $^{89}$Zr, $^{94m}$Tc, $^{94}$Tc, $^{99m}$Tc, $^{120}$I, $^{123}$I, $^{124}$I, $^{125}$I, $^{131}$I, $^{154\text{-}158}$Gd, $^{186}$Re, $^{188}$Re, $^{51}$Mn, $^{52}$mMn, $^{55}$Co, $^{72}$As, $^{75}$Br, $^{76}$Br, $^{82}$mRb, $^{83}$Sr, $^{211}$At, $^{212}$Bi, and $^{225}$Ac.

10. The composition of claim 6, wherein the antibody is cetuximab and the peptide is cyclo(RGDyK).

11. The composition of claim 1, wherein the first bioorthogonal ligation moiety is trans-cyclooctene and the second bioorthogonal ligation moiety is tetrazine.

12. The composition of claim 6, wherein the first bioorthogonal ligation moiety is trans-cyclooctene and the second bioorthogonal ligation moiety is tetrazine.

* * * * *